United States Patent
Huang et al.

(10) Patent No.: US 10,426,745 B2
(45) Date of Patent: Oct. 1, 2019

(54) POLYMERIC METFORMIN AND ITS USE AS A THERAPEUTIC AGENT AND AS A DELIVERY VEHICLE

(71) Applicant: The University of North Carolina at Chapel Hill, Chapel Hill, NC (US)

(72) Inventors: Leaf Huang, Durham, NC (US); Yi Zhao, Chapel Hill, NC (US); Shutao Guo, Jamaica Plain, MA (US); Kai Shi, Chapel Hill, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 0 days.

(21) Appl. No.: 15/555,794

(22) PCT Filed: Mar. 4, 2016

(86) PCT No.: PCT/US2016/020921
§ 371 (c)(1),
(2) Date: Sep. 5, 2017

(87) PCT Pub. No.: WO2016/144766
PCT Pub. Date: Sep. 15, 2016

(65) Prior Publication Data
US 2018/0055792 A1    Mar. 1, 2018

Related U.S. Application Data

(60) Provisional application No. 62/129,276, filed on Mar. 6, 2015.

(51) Int. Cl.
| | | |
|---|---|---|
| A61K 48/00 | (2006.01) | |
| A61K 31/155 | (2006.01) | |
| A61K 47/28 | (2006.01) | |
| A61K 47/55 | (2017.01) | |
| A61K 47/61 | (2017.01) | |
| A61K 47/54 | (2017.01) | |
| A61K 47/69 | (2017.01) | |
| A61K 9/51 | (2006.01) | |
| A61K 9/00 | (2006.01) | |
| C08G 73/02 | (2006.01) | |
| C12N 15/85 | (2006.01) | |
| C12N 15/88 | (2006.01) | |
| B82Y 5/00 | (2011.01) | |

(52) U.S. Cl.
CPC .......... *A61K 31/155* (2013.01); *A61K 9/0019* (2013.01); *A61K 9/5123* (2013.01); *A61K 47/28* (2013.01); *A61K 47/55* (2017.08); *A61K 47/554* (2017.08); *A61K 47/61* (2017.08); *A61K 47/6911* (2017.08); *A61K 48/00* (2013.01); *C08G 73/02* (2013.01); *C12N 15/85* (2013.01); *C12N 15/88* (2013.01); *B82Y 5/00* (2013.01)

(58) Field of Classification Search
CPC ...... A61K 48/00; A61K 31/155; A61K 47/28; A61K 47/55; A61K 47/61; A61K 47/54; A61K 47/69; A61K 9/51; A61K 9/00; C08G 73/02; C12N 15/85; C12N 15/88; B82Y 5/00
See application file for complete search history.

(56) References Cited

U.S. PATENT DOCUMENTS

| | | |
|---|---|---|
| 3,174,901 A | 3/1965 | Sterne |
| 4,507,466 A | 3/1985 | Tomalia et al. |
| 4,558,120 A | 12/1985 | Tomalia et al. |
| 4,568,737 A | 2/1986 | Tomalia et al. |
| 4,587,329 A | 5/1986 | Tomalia et al. |
| 4,631,337 A | 12/1986 | Tomalia et al. |
| 4,694,064 A | 9/1987 | Tomalia et al. |
| 4,713,975 A | 12/1987 | Tomalia et al. |
| 4,737,550 A | 4/1988 | Tomalia |
| 4,857,599 A | 8/1989 | Tomalia et al. |
| 4,871,779 A | 10/1989 | Killat et al. |
| 5,418,301 A | 5/1995 | Hult et al. |
| 5,514,378 A | 5/1996 | Mikos et al. |
| 5,820,873 A | 10/1998 | Choi et al. |
| 8,389,768 B2 | 3/2013 | Huang et al. |

(Continued)

FOREIGN PATENT DOCUMENTS

| | | |
|---|---|---|
| EP | 1 996 243 B1 | 3/2008 |
| WO | WO-2011-109151 A1 | 9/2011 |
| WO | WO2011109151 * | 9/2011 |

(Continued)

OTHER PUBLICATIONS

Collin et al., 2004, caplus an 2004:704087.*
Khouri et al., 2005, caplus an 2005:39466.*
Khouri et al.—full reference, 2004, Eur. J. Biochem. 271, 4745-4752.*
Collin et al.—full reference, 2004, Journal of Mass Spectrometry, 39, 890-902.*
Aydar, E., et al., "Sigma Receptors and Cancer: Possible Involvement of Ion Channels," Cancer Research, vol. 64, pp. 5029-5035, Aug. 1, 2004.
Banerjee, R., et al., "Anisamide-Targeted Stealth Liposomes: A Potent Carrier for Targeting Doxorubicin to Human Prostate Cancer Cells," International Journal of Cancer, vol. 112, pp. 693-700, 2004.

(Continued)

*Primary Examiner* — Sun Jae Yoo
(74) *Attorney, Agent, or Firm* — Alston & Bird, LLP

(57) ABSTRACT

Provided herein are polymers comprising Metformin residues ("PolyMet") as useful therapeutic agents, delivery vehicles and transfection agents for nucleotides. Also provided herein are methods for the treatment of a disease or an unwanted condition in a subject, wherein the methods comprise administering PolyMet as a therapeutic agent to combat the disease or condition. Also provided herein are methods for the treatment of a disease or an unwanted condition in a subject, wherein the methods comprise administering a therapeutic agent in a delivery vehicle that comprises PolyMet. Further provided herein are methods for making PolyMet.

3 Claims, 63 Drawing Sheets

(56) References Cited

U.S. PATENT DOCUMENTS

2010/0240883 A1  9/2010  Wu et al.

FOREIGN PATENT DOCUMENTS

| WO | WO 2013-103384 A1 | 7/2013 |
| WO | WO 2013-188452 | 12/2013 |
| WO | WO 2014-041566 | 3/2014 |

OTHER PUBLICATIONS

Bolster, D.R., et al., "AMP-activated Protein Kinase Suppresses Protein Synthesis in Rat Skeletal Muscle through Down-regulated Mammalian Target of Rapamycin (mTOR) Signaling," J. Biol. Chem., vol. 277, No. 27, pp. 23977-23980, 2002.

Chono, S., et al., "An efficient and low immunostimulatory nanoparticle formulation for systemic siRNA delivery to the tumor," Journal of Controlled Release, vol. 131, pp. 64-69, 2008.

Collin, F., et al., "Liquid chromatographic/electrospray ionization mass spectrometric identification of the oxidation end-products of metformin in aqueous solutions," J. Mass. Spectrom., vol. 39, No. 8, pp. 890-902, Aug. 3, 2004.

Dowling, R.J., et al., "Metformin Inhibits Mammalian Target of Rapamycin-Dependent Translation Initiation in Breast Cancer Cells," Cancer Research, vol. 67, pp. 10804-10812, 2007.

Feng, Y., et al., "Metformin promotes autophagy and apoptosis in esophageal squamous cell carcinoma by downregulating Stat3 signaling," Cell Death and Disease, vol. 5, pp. 1-12, 2014.

Gou, S.M., et al., "Low Concentrations of Metformin Selectively Inhibit CD133+Cell Proliferation in Pancreatic Cancer and Have Anticancer Action," PLoS One, vol. 8, No. 5, pp. 1-9, May 2013.

Hu, T., et al., "Reprogramming ovarian and breast cancer cells into non-cancerous cells by low-dose metformin or SN-38 through FOXO3 activation," Scientific reports, vol. 4, pp. 1-13, 2014.

Huang, R., et al., "The use of lactoferrin as a ligand for targeting the polyamidoamine-based gene delivery system to the brain," Biomaterials, vol. 29, No. 2, pp. 238-246, 2008.

Isselbacher et al., Harrison's Principles of Internal Medicine 13th ed., pp. 1814-1882, 1996.

Khouri, H., et al., "Radical-induced oxidation of metformin," Eur. J. Biochem., vol. 271, pp. 4745-4752, 2004.

Kimura, N., et al., "A possible linkage between AMP-activated protein kinase (AMPK) and mammalian target of rapamycin (mTOR) signalling pathway," Genes to Cells, vol. 9, pp. 65-79, 2003.

Kisfalvi, K., et al., "Metformin Inhibits the Growth of Human Pancreatic Cancer Xenografts," Pancreas, 2013, vol. 42, pp. 781-785.

LeRoith, D., "Insulin-like growth factors and cancer: from basic biology to therapeutics," Humana Press, New York; 2012.

Marathe, P.H., et al., "Effect of altered gastric emptying and gastrointestinal motility on metformin absorption," Br. J. Clin. Pharmacol., vol. 50, 325-332, 2000.

Matsubara, S., et al., "mTOR plays critical roles in pancreatic cancer stem cells through specific and stemness-related functions," Scientific Reports, vol. 3, No. 3230, pp. 1-10, 2013.

Miao, L., et al., "Nanoparticles with Precise Ratiometric Co-Loading and Co-Delivery of Gemcitabine Monophosphate and Cisplatin for Treatment of Bladder Cancer," Advanced Functional Materials, vol. 24, pp. 6601-6611, 2014.

Mizushima, N., et al., "Methods in Mammalian Autophagy Research," Cell, vol. 140, pp. 313-326, 2010.

Morales, D.R., et al., "Metformin in Cancer Treatment and Prevention," Annual Review of Medicine 2015, vol. 66, pp. 4.1-4.13, 2014.

Moulton, H.M., et al., "Peptide-Morpholino Conjugate: A Promising Therapeutic for Duchenne Muscular Dystrophy," Ann N.Y. Acad. Sci., vol. 1175, pp. 55-60, 2009.

Nicolaou, K.C., et al., "Calicheamicin $\theta^1$: A Rationally Designed Molecule with Extremely Potent and Selective DNA Cleaving Properties and Apoptosis Inducing Activity," Angew. Chem Intl. Ed. Engl., vol. 33, No. 2, pp. 183-186, 1994.

Nimesh, S., et al., "Guanidinium-grafted polyethylenimine: An efficient transfecting agent for mammalian cells," European journal of Pharmaceutics and Biopharmaceutics, vol. 68, pp. 647-655, 2008.

Shi, W.Y., et al., "Therapeutic metformin/AMPK activation blocked lymphoma cell growth via inhibition of mTOR pathway and induction of autophagy," Cell Death and Disease, vol. 3, pp. 1-9, 2012.

Tabuchi, Y., et al., "Resistance to paclitaxel therapy is related with Bcl-2 expression through an estrogen receptor mediated pathway in breast cancer," International Journal of Oncology, vol. 34, pp. 313-319, 2009.

Tomic, T., et al., "Metformin inhibits melanoma development through autophagy and apoptosis mechanisms," Cell Death and Disease, vol. 2, pp. 1-10, 2011.

Yue, W., et al., "Repurposing of Metformin and Aspirin by Targeting AMPK-mTOR and inflammation for pancreatic cancer prevention and treatment," Cancer Prevention Research, vol. 7, pp. 388-397, 2014.

Zhang, R., et al., "The effect of side-chain functionality and hydrophobicity on the gene delivery capabilities of cationic helical polypeptides," Biomaterials, vol. 35, pp. 3443-3454, 2014.

Zulato, E., et al., "Prognostic significance of AMPK activation in advanced stage colorectal cancer treated with chemotherapy plus bevacizumab," British Journal of Cancer, vol. 111, pp. 25-32, 2014.

PCT International Search Report and Written Opinion of the International Searching Authority for application PCT/US2016/020921 dated Sep. 15, 2016.

Extended European Search Report corresponding to European Application No. 16762220.8 dated Oct. 11, 2018 8 pages.

* cited by examiner

A

B

C

| Polymer | MTD,* mg/kg |
|---------|-------------|
| PEI     | 2.5         |
| PolyMet | 11.5        |

| Nanoparticles | Size(nm) | PDI | ξ-potential |
|---|---|---|---|
| PEI-HA complex | 110.7 ± 0.5 | 0.325 | -25.2 ± 0.3 |
| PolyMet-HA complex | 103.1 ± 0.4 | 0.296 | -24.1 ± 0.2 |
| LPH-PEI | 81.6 ± 0.2 | 0.281 | 21.3 ± 0.5 |
| LPH-PolyMet | 74.2 ± 0.3 | 0.215 | 20.5 ± 0.3 |

FIGURE 4E

|              | PBS         | Metformin  | LPH-PEI    | LPH-PolyMet |
|--------------|-------------|------------|------------|-------------|
| WBC          | 2.2 ± 1.3   | 2.4± 0.8   | 2.4 ± 0.7  | 2.4 ± 0.6   |
| Lymphocytes  | 1.9 ± 0.8   | 1.5 ± 0.3  | 1.2 ± 0.6  | 1.6 ± 0.2   |
| Granulocytes | 2.7 ± 0.6   | 1.4 ± 0.3  | 1.2 ± 0.3  | 1.3 ± 0.3   |
| Monocytes    | 0.6 ± 0.3   | 0.8 ± 0.3  | 0.2 ± 0.1  | 0.4 ± 0.2   |

| Samples | Hydrodynamic diameter ($D_H$, nm) | Polydispersity index (PDI) | Zeta potential ($\zeta$, mV) |
|---|---|---|---|
| PH core | 89.2 ± 3.5 | 0.21 ± 0.03 | -29.3 ± 4.2 |
| Blank LipoMET | 57.3 ± 1.4 | 0.16 ± 0.02 | +49.1 ± 2.5 |
| Blank LipoEDA | 65.6 ± 2.0 | 0.26 ± 0.06 | +15.2 ± 1.9 |
| LipoMET-PH | 102.5 ± 2.6 | 0.18 ± 0.04 | +22.5 ± 3.6 |
| LipoEDA-PH | 115.8 ± 3.9 | 0.32 ± 0.08 | +7.5 ± 2.1 |

FIGURE 24

|  | Size (nm) | PDI | Z-η (mv) |
|---|---|---|---|
| Lipo-DOBP | 130.5±0.3 | 0.16 | 52.9±0.6 |
| Lipo-DOTAP | 123.6±0.5 | 0.17 | 47.0±1.2 |
| Protamine/DNA | 122.3±0.4 | 0.15 | -28.4±1.3 |
| DOBP-LPD | 145.3±0.6 | 0.15 | 36.8±0.2 |
| DOTAP-LPD | 148.8±1.0 | 0.14 | 37.4±0.0 |

FIGURE 35

POLYMERIC METFORMIN AND ITS USE AS A THERAPEUTIC AGENT AND AS A DELIVERY VEHICLE

CROSS-REFERENCE TO RELATED APPLICATIONS

This application is a national stage application filed under 35 U.S.C. § 371 of International Application No. PCT/US2016/020921, filed Mar. 4, 2016, which claims priority to U.S. Provisional Application No. 62/129,276, filed Mar. 6, 2015, the contents of each of which is hereby incorporated herein in its entirety by reference.

STATEMENT OF GOVERNMENT SUPPORT

This invention was made with government support under Grant Nos. CA151652, CA149363, and DK100664 awarded by the National Institutes of Health. The government has certain rights in the invention.

FIELD OF THE INVENTION

The present invention involves polymers and macromolecules comprising covalently bound metformin residues referred to herein as poly-metformin (PolyMet), which itself has therapeutic agent properties and can also be used as a delivery vehicle for other therapeutic agents and as a transfection agent.

BACKGROUND OF THE INVENTION

Metformin is orally effective in the treatment of Type 2 diabetes. Metformin is approved by the U.S. Food & Drug Administration for the therapeutic treatment of diabetes. The chemical name of Metformin is N,N-dimethylimidodicarbonimidic diamide. It is a biguanide, anti-hyperglycemic agent currently marketed in the United States in the form of its hydrochloride salt, 1,1-dimethylbiguanide hydrochloride.

Metformin is known to improve insulin action at the cellular level, but not affect insulin secretion. Metformin does not promote weight gain and has beneficial effects on several cardiovascular risk factors. Accordingly, Metformin is widely regarded as the drug of choice for most patients with Type 2 diabetes.

Despite the effectiveness of Metformin as a diabetes medication, it nonetheless suffers from some drawbacks. While Metformin is the first line therapy for diabetes, its rapid clearance from plasma requires multiple high doses for continued active plasma concentrations. In particular, while Metformin is effectively taken up in the small intestine, it is poorly absorbed in the colon (Marathe, Br. J. Clin., Pharmacol., 50, 325-332 (2000)). As a result, the time window for effective plasma concentrations of Metformin is limited. Because of this narrow absorption window, metformin is typically prescribed to be taken about 2-3 times a day.

For this and other reasons, Metformin has potential uses that are not being fully exploited. The present disclosure addresses many of these shortcomings.

BRIEF SUMMARY OF THE INVENTION

Provided herein are polymers comprising Metformin residues ("PolyMet"). PolyMet is a useful therapeutic agent, delivery vehicle and a transfection agent for genetic material, such as nucleic acids.

Also provided herein are methods for the treatment of a disease or an unwanted condition in a subject, wherein the methods comprise administering PolyMET as a therapeutic agent to combat the disease or condition.

Also provided herein are methods for the treatment of a disease or an unwanted condition in a subject, wherein the methods comprise administering a therapeutic agent in a delivery vehicle, such as a nanoparticle, that comprises PolyMet.

Further provided herein are methods for making PolyMet.

These and other aspects are disclosed in complete detail below.

BRIEF DESCRIPTION OF THE FIGURES

FIG. 1C depicts maximum tolerable dose (MTD) of PEI and PolyMet. CD-1 mice were IV injected with various concentrations of polymer in 0.9% NaCl solution. *The MTD is 0.5 mg/kg below any lethal dose within 24 hours of IV injection. At least three mice were tested at each dose.

FIG. 5A depicts hematology test of whole blood.

In FIG. 6A, tumor volumes were measured every day.

FIG. 7B depicts inducing autophagy and apoptosis mechanisms. Mice bearing H460 tumors were given IV injections every other day and analysis of tumor proteins was prepared 24 h after the second injection. Cells under autophagy were stained by LC3b antibody (red) and apoptosis of cells was indicated by TUNEL assay (green). Nuclei are stained blue. The percentage denotes the average percentage of LC3b positive cells (red) and the percentage of TUNEL positive cells (green), respectively. Five randomly selected microscopic fields were quantitatively analyzed on ImageJ. Data are mean±S.D. (n=5 per group).

FIG. 9 refers to LPH nanoparticles composed of PolyMet systemically delivered anti-apoptotic VEGF siRNA to the tumor site and inhibited tumor growth. H460 tumor-bearing mice were injected intravenously every other day.

FIG. 16 depicts data showing in vivo gene silencing effect of different LPH nanoparticles in H460 xenografts.

FIG. 24 depicts characteristics of various formulations.

FIG. 35 depicts characteristic parameters of different formulations (DLS). Lipo-DOTAP is composed of protamine/Hyaluronic acid core and DOTA/cholesterol lipid coating. Lipo-DOBP is composed of protamine/Hyaluronic acid core and DOBP/cholesterol lipid coating.

DETAILED DESCRIPTION OF THE INVENTION

Figure 1A:
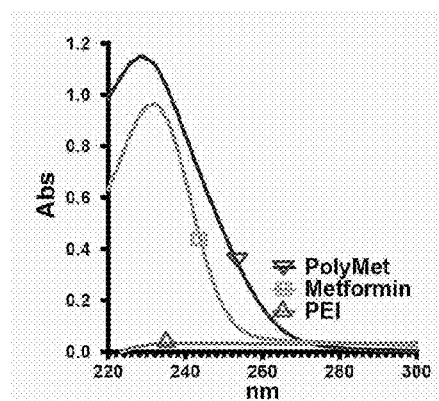
FIG. 1A depicts the UV spectra of Metformin, PEI and PolyMet in the range of 220 to 300 nm. Both PolyMet and Metformin have a maximum absorbance around 230 nm, suggesting that both of them have a similar functional structure, while PEI did not.
Figure 1B:
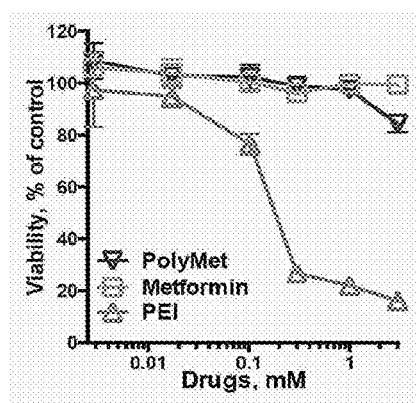
FIG. 1B depicts cytotoxicity of metformin, PEI and PolyMet. H460 cell availability was measured using a MTT assay after 24 h of exposure to metformin, PolyMet and PEI solutions. Data are mean±S.D. (n=8).

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims.

Metformin (N',N'-dimethylbiguanide), one of the most effective drugs used to treat Type 2 diabetes, also has potential as a therapeutic agent for various types of cancers. (Morales, D. R. & Morris, A. D. Metformin in Cancer Treatment and Prevention. *Annual review of medicine* (2014)). The compound and its preparation are disclosed, for example, in U.S. Pat. No. 3,174,901. Metformin hydrochloride can be purchased commercially as well.

Using novel materials with pharmacological activities for drug delivery could synergistically enhance therapeutic efficacy. Disclosed herein is the design and syntheses of polymers Metformin, i.e., polymers comprising residues of Metformin, referred to collectively as PolyMet. Because in embodiments the polymer is conjugated through a nonactive carbon backbone, the bioactive guanidine portion is essentially available as Metformin and PolyMet provides new opportunities for the treatment of cancer. Furthermore, PolyMet can provide enhanced gene delivery. Polymers containing guanidinium groups have higher gene delivery efficiency than their amine-containing counterparts (Zhang, R., Zheng, N., Song, Z., Yin, L. & Cheng, J. The effect of side-chain functionality and hydrophobicity on the gene delivery capabilities of cationic helical polypeptides. *Biomaterials* 35, 3443-3454 (2014). Nimesh, S. & Chandra, R. Guanidinium-grafted polyethylenimine: an efficient transfecting agent for mammalian cells. *European journal of pharmaceutics and biopharmaceutics: official journal of Arbeitsgemeinschaft fur Pharmazeutische Verfahrenstechnik e. V* 68, 647-655 (2008).

PolyMet is a drug delivery vehicle that itself has pharmacological and therapeutic activities. Accordingly, PolyMet can synergistically enhance therapeutic efficacy. PolyMet dramatically decreased the cytotoxicity of PEI in vitro and in vivo. Given its polycationic activity, PolyMet can also be formulated into LPH (liposome-polycation-hyaluronic acid) nanoparticles ("LPH-PolyMet"). As shown herein, both Metformin and LPH-PolyMet nanoparticles significantly suppress cancer development that may be attributable to activating AMP-activated protein kinase (AMPK), inhibiting the mTOR pathways, and/or inducing autophagy and apoptosis. LPH-PolyMet nanoparticles can also be used as a delivery vehicle for siRNA molecules, thus facilitating gene delivery. Accordingly, PolyMet has many uses in cancer therapy. In addition, PolyMet itself can facilitate transfection of genetic material, such as plasmid DNA, into cells. Thus, PolyMet is a drug by itself and a drug carrier for delivering other drugs and a transfection agent.

Figure 1C:
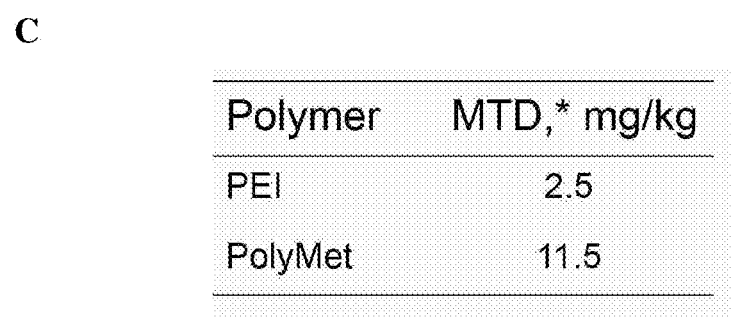

Other advantages are also provided by PolyMet. Notably, PolyMet has a dramatically lower cytotoxicity (FIG. 1C) and higher maximum tolerable dose (MTD, FIG. 1D) compared to PEI, indicating PolyMet, which contains residues of Metformin, is less toxic than its secondary amine-containing counterpart.

As will be fully described herein, PolyMet provides at least:

1. Therapeutic properties as an anti-diabetic and as an anti-tumor agent;

2. Therapeutic agent delivery properties, in particular, anti-cancer drugs and nucleotide compounds such as siRNA; pDNA; mRNA; and 3. Therapeutic agent delivery properties, in particular, anti-cancer drugs and macromolecules such as peptides; protein.

As used herein, the term "PolyMet" refers to a polymer of Metformin, i.e., a polymer or macromolecule comprising residues of Metformin, the structures of which are described elsewhere herein. The polymer can have a wide range of molecular weights. This and other aspects of PolyMet are described fully below. PolyMets can be prepared from carbon chains that have available primary and/or secondary amines, such as:

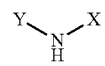

or

where X, Y is the hydrocarbon, either linear or branched, containing n number of carbon, wherein n is an integer from 2 to 50,000; 2 to 40,000; 2 to 30,000; 2 to 20,000; 2 to 10,000; 2 to 5,000; 2 to 4,000; 2 to 3,000; 2 to 2,0002 to 8,000; 2 to 7,000; 2 to 6,000; 2 to 5,000; 2 to 4,000; 2 to 3,000; 2 to 2,000; 2 to 1,000; 2 to 500; 2 to 200; 2 to 100; or 2 to 50. As described herein, Poly-Metformin (PolyMet) can be synthesized by the reaction of linear or branched polyethylenimine (PEI), polypropylenimine (PPI), any known polymers, dendrimers and dicyandiamide to comprise a residue of Metformin.

As used herein, "PEI" refers to polyethylenimine, and "PPI" refers to polypropylenimine. The following formula represents PEI when p is 1, and PPI when p is 2:

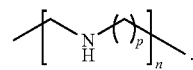

PEI is a useful starting material for the preparation of PolyMet. PEI can be linear or branched. Linear PEI has the following chemical structure:

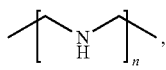

which is also known in the art as:

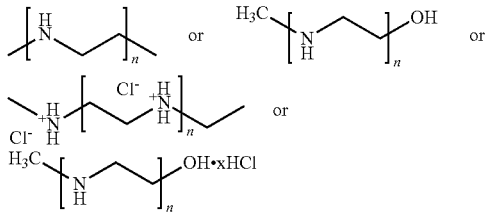

In the above structures, n is an integer from 2 to 10,000 or more.

As used herein, "PPI" refers to polypropylenimine. It is a useful starting material for the preparation of a PolyMet. PPI can be linear or branched. Linear PPI has the following chemical structure:

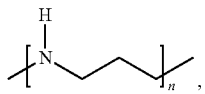

wherein n is an integer from 2 to 10,000.

An example of a PEGylated PEI or PPI derivative has the structure:

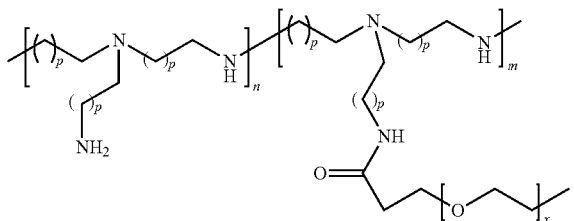

wherein m is from about 0.1 to about 0.9, n is from about 0.1 to about 0.9, and wherein m and n represent the mole fraction of each unit in the polymer and the sum of m and n is 1, p is 1 or 2, and x is an integer from 1 to about 500. In PEI polymers, p is 1. In PPI polymers, p is 2.

An example of a PEGylated PEI or PPI derivative with targeting modifications has the structure:

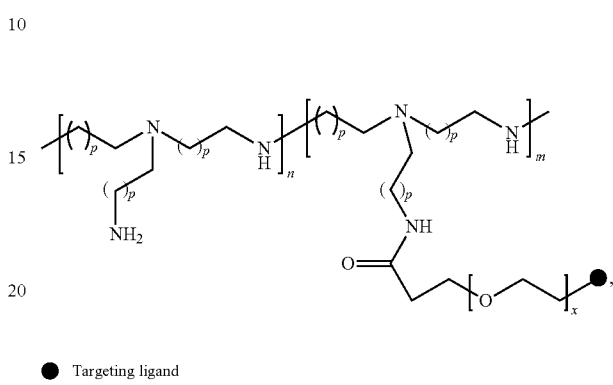

● Targeting ligand wherein, m, n, p and x are as described above.

Branched PEI or PPI refers to PEI or PPI monomer units that further contain pendant ethylamine units or PEI moieties, or pendant propylamine units or PPI moieties to the backbone PEI/PPI. A non-limiting example is:

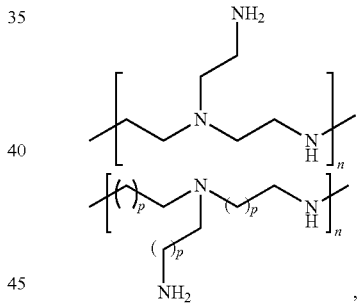

wherein in PEI polymers, p is 1, and in PPI polymers, p is 2; and

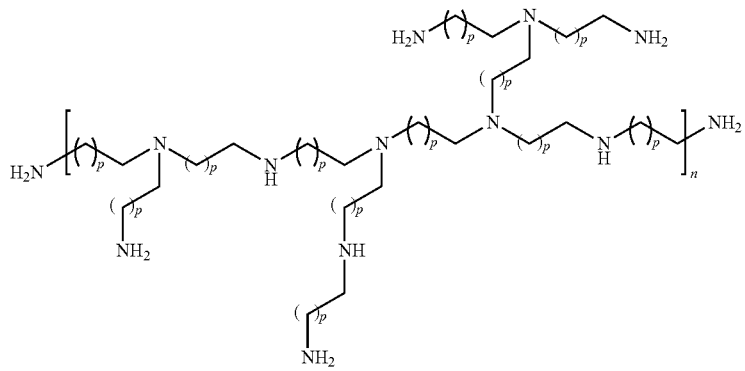

where n is the number of repeating units in the branched PEI structure, where p is 1, or the PPI structure, where p is 2. Useful values of n are from 2 to about 1,000,000; 2 to about 500,000; 2 to about 100,000; 2 to about 50,000; 2 to about 25,000; 2 to about 10,000; 2 to about 5,000; 2 to about 1,000 or less. Branched PEIs or PPIs can contain additional ethylamine units or PEI moieties or additional propylamine units or PPI moieties covalently bound to any available Nitrogen. Such linear or branched PEIs/PPIs are commercially available or easily obtainable using known methods. In each instance, the size or molecular weight (MW) of the PEI can be indicated by the integer "n," which is described elsewhere herein. In the structure above, any Hydrogen can be replaced by a residue of Metformin.

Specific examples of polypropylenimine (PPI) include PPI generation 1:

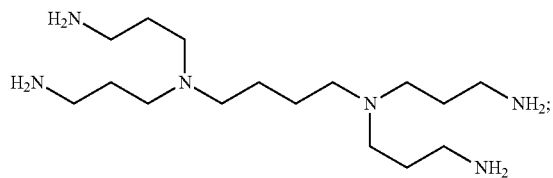 [SMILES: NCCCN(CCCN)CCCCN(CCCN)CCCN]

A polypropylenimine (PPI), generation 2:

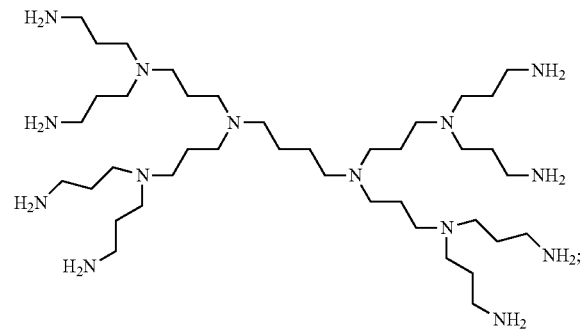 [SMILES: NCCCN(CCCN)CCCN(CCCCN(CCCN(CCCN)CCCN)CCCN(CCCN)CCCN)CCCN(CCCN)CCCN]

and, as is known in this field and discussed elsewhere herein, further generations can be prepared whereby in each successive generation, the outermost primary Nitrogens are further branched to form dendrimers, which are discussed below.

Dendrimers are polymers with densely branched structures having a large number of reactive groups, which, in the present disclosure refers to primary and secondary Nitrogens. A dendritic polymer includes several layers or generations of repeating units which all contain one or more branch points. Dendrimers, including hyperbranched dendritic polymers, are prepared by condensation reactions of monomeric units having at least two reactive groups. Dendrimers generally consist of terminal surface groups, interior branch junctures having branching functionalities greater than or equal to two, and divalent connectors that covalently connect neighboring branching junctures.

Examples of dendrimers and dendrons, and methods of synthesizing the same are set forth in U.S. Pat. Nos. 4,507,466; 4,558,120; 4,568,737; 4,587,329; 4,631,337; 4,694,064; 4,713,975; 4,737,550; 4,871,779 and 4,857,599. Examples of hyperbranched polymers and methods of preparing the same are set forth, for example in U.S. Pat. No. 5,418,301. Non-limiting examples of suitable dendrimers for derivitization to prepare a PolyMet macromolecule are: polypropylenimine dendrimer; polyamidoamine (PAMAM) dendrimer; polyaryl ether dendrimer; polylysine dendrimer; polyester dendrimer; polyimide dendrimer; dendritic polyglycerol; and triazine dendrimers. Dendrimers can be defined by the polymer that makes up the dendrimer, by chemical moieties present on the dendrimer and/or the molecular weight of the dendrimer. As provided herein, the dendrimer size and surface functionality can affect the percent derivitization of the amines.

Dendrimers can be prepared by convergent or divergent synthesis. Divergent synthesis of dendrimers involves a molecular growth process that occurs through a consecutive series of geometrically progressive step-wise additions of branches upon branches in a radially outward direction to produce an ordered arrangement. Thus, each dendritic macromolecule can be said to include a core cell, one or more layers of internal cells, and an outer layer of surface cells, wherein each of the cells includes a single branch juncture. The cells can be the same or different in chemical structure and branching functionality. The surface branch cells may contain either chemically reactive or passive functional groups, chemically reactive surface groups can be used for further extension of dendritic growth or for modification of dendritic molecular surfaces. The chemically passive groups may be used to physically modify dendritic surfaces, such as to adjust the ratio of hydrophobic to hydrophilic terminals and/or improve the solubility of the dendritic polymer for a particular solvent.

The convergent synthesis of dendrimers involves a growth process that begins from what will become the surface of the dendron or dendrimer and progresses radially toward a focal point or core. The dendritic polymers may be ideal or non-ideal, i.e., imperfect or defective. Imperfections are normally a consequence of either incomplete chemical reactions, or unavoidable competing side reactions. In practice, real dendritic polymers are generally non-ideal, i.e., contain certain amounts of structural imperfections.

Hyperbranched dendritic networks refer to a class of dendritic polymers that contain high levels of non-ideal irregular branching. Specifically, hyperbranched polymers contain a relatively high number of irregular branching areas in which not every repeat unit contains a branch juncture. The preparation and characterization of dendrimers, dendrons, random hyperbranched polymers, controlled hyperbranched polymers, and dendrigrafts is well known.

As discussed above, dendrimers are repetitively branched macromolecules. They are generally symmetrical macromolecules. As used herein, a dendrimer comprises exterior or surface primary amino groups. A non-limiting example of a dendrimer is:

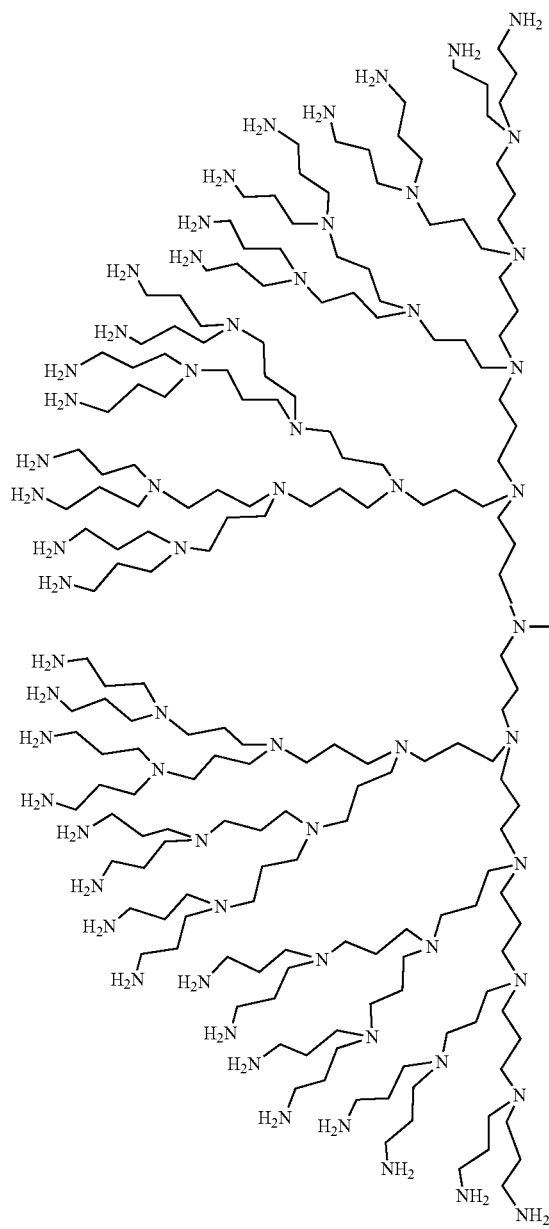
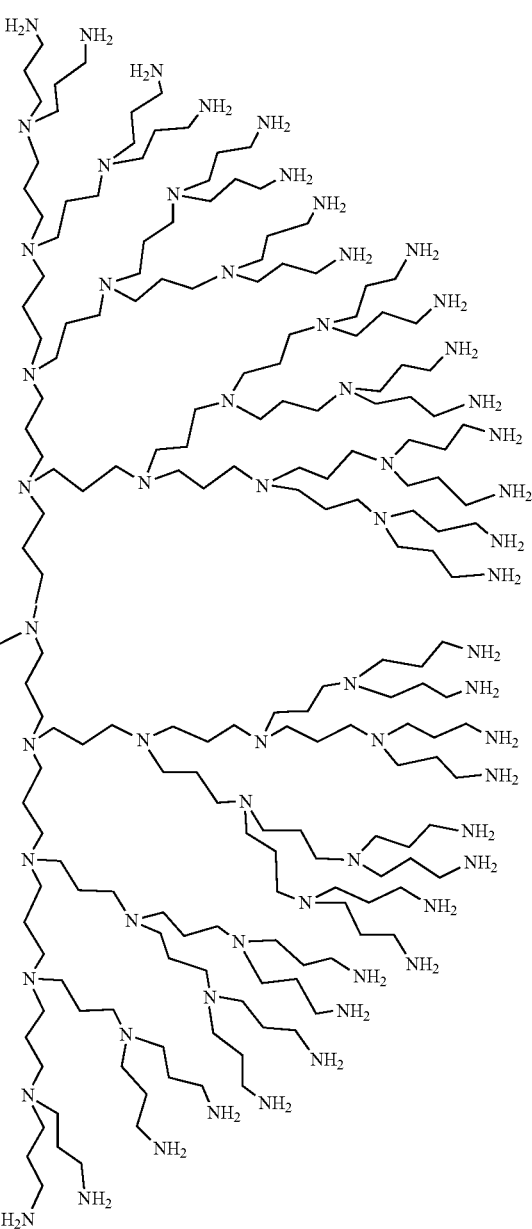

In yet another embodiment, dihexadecylamine (HCl) having the structure (free base):

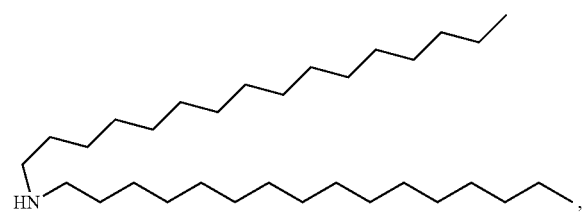 [SMILES: CCCCCCCCCCCCCCCCNCCCCCCCCCCCCCCCC]

that can be derivatized wherein the hydrogen on the Nitrogen is replaced and the Nitrogen is covalently bound to a residue of Metformin resulting in a double chain amphiphile with a biguanide head group.

As used herein, a "residue of Metformin" means that a Nitrogen in the polymer backbone or in the macromolecule scaffold is taken together with the residue of Metformin to form a Metformin molecule covalently linked in a polymer chain as described herein. Each Metformin in the polymer chain can share a carbon with any other adjacent Metformin. The chemical structure of a residue of Metformin is described below.

In light of the unique properties of PolyMet, the present subject matter is directed to the following embodiments that exploit PolyMet's usefulness.

Polymers of Metformin

In an embodiment, the present subject matter is directed to a polymer of Metformin, Poly-MET, having the following chemical formula I:

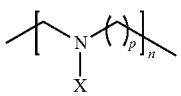

wherein n is an integer from two (2) to 100,000; or in particular 2 to 10,000 or less; p is 1 or 2, wherein, X is hydrogen or a residue of Metformin having the formula:

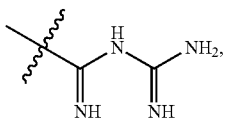 [SMILES: *C(=N)NC(=N)N]

wherein at least 5% of X in the PolyMet is a residue of Metformin. However, useful PolyMets are where X is a residue of Metformin in at least 0.0001, 0.001, 0.01, 0.1, 2, 3, 4, 5, 10, 15, 20, 25, 30, 35, 40, 45, 50, 55, 60, 65, 70, 75, 80, 85, 90, 95 or 100% of the occurrences of X.

When the residue of Metformin is bound to a primary and secondary amine on a polymer or dendrimer, the residue together with a Nitrogen on A can be a monomethyl biguanide and has the following general structure:

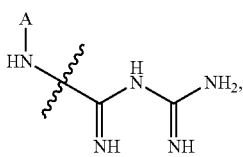

wherein, A represents a polymer, an in particular embodiments, a dendrimer.

The above PolyMets can have a % wt of Metformin residues in the PolyMet from 0.001% wt/wt to above 90% wt/wt.

Useful values of n include from 2 to about 10,000; from 2 to about 5,000; from 2 to about 4,000; from 2 to about 3,000; from 2 to about 2,000; from 2 to about 1,000; from 2 to about 500; from 2 to about 250; from 50 to about 10,000; from 100 to about 9,000; from 500 to about 8,000; from 1,000 to about 7,000; from 1,500 to about 6,000; from 2,000 to about 5,000; and from 2,500 to about 4,500.

In an embodiment, the present subject matter is directed to a polymer of metformin, Poly-MET, having the following chemical formula II

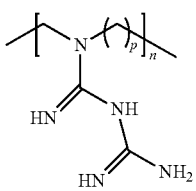

wherein, p is 1 or 2, and n is an integer from 2 to 100,000, in particular 2 to 10,000.

In an embodiment, the present subject matter is directed to a branched polymer of metformin, Poly-MET, having the chemical formula I as shown above, wherein X is a hydrogen, a residue of Metformin, a residue of ethyl amine having the following chemical formula:

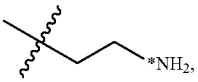

or a residue of propylamine having the following chemical formula:

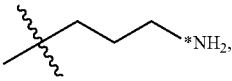

wherein, in each instance, zero, one or both hydrogen(s) on *N is substituted with a) additional residue(s) of ethyl amine or propylamine, which, in each instance, can also be further substituted in the same manner, thereby forming an increasingly branched (which can also be a dendritic) structure, and/or b) a residue of Metformin, wherein at least 5% of the primary *Ns in the branched PEI/PPI are substituted with a residue of Metformin. Particularly useful PolyMets are those having a branched backbone are where *N is covalently bound to a residue of Metformin in at least about 0.0001, 0.001, 0.01, 0.1, 2, 3, 4, 5, 10, 15, 20, 25, 30, 35, 40, 45, 50, 55, 60, 65, 70, 75, 80, 85, 90, 95 or about 100% of the occurrences of *N.

The branched PolyMets can have a % wt of Metformin residues in the branched PolyMet from 0.001% wt/wt to above 90% wt/wt.

Branched PolyMets include those of general formula III:

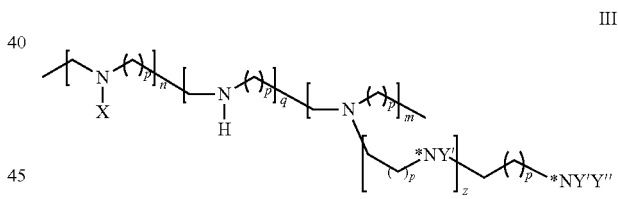

wherein each p is independently 1 or 2, n is from 0.1 to 1.0; q is from 0.1 to 1.0; m is from 0.1 to 1.0, wherein n, q and m represent the mole fraction of each unit in the polymer and the sum of n, q and m is 1; z is an integer from 0 to 1,000; *N is a Nitrogen that can be derivatized with a residue of Metformin, or an ethylamine or propylamine, either of which will themselves contain a *N; X is hydrogen or a residue of Metformin; and Y' and Y" are in dependently hydrogen, a residue of Metformin, or an ethylamine or propylamine, either of which will themselves contain a *N.

Polymers and dendrimers of Formula III can have molecular weights of from about 100 to about 6,000,000; from about 100 to about 500,000; from about 200 to about 250,000; from about 200 to about 200,000; from about 200 to about 100,000; from about 200 to about 50,000; from about 200 to about 10,000; from about 200 to about 5,000; from about 200 to about 1,000; from about 200 to about 800; from about 200 to about 700; from about 200 to about 600; and from about 200 to about 500.

Non-limiting examples of branched PolyMets include:

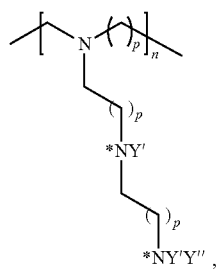

wherein p is 1 or 2;

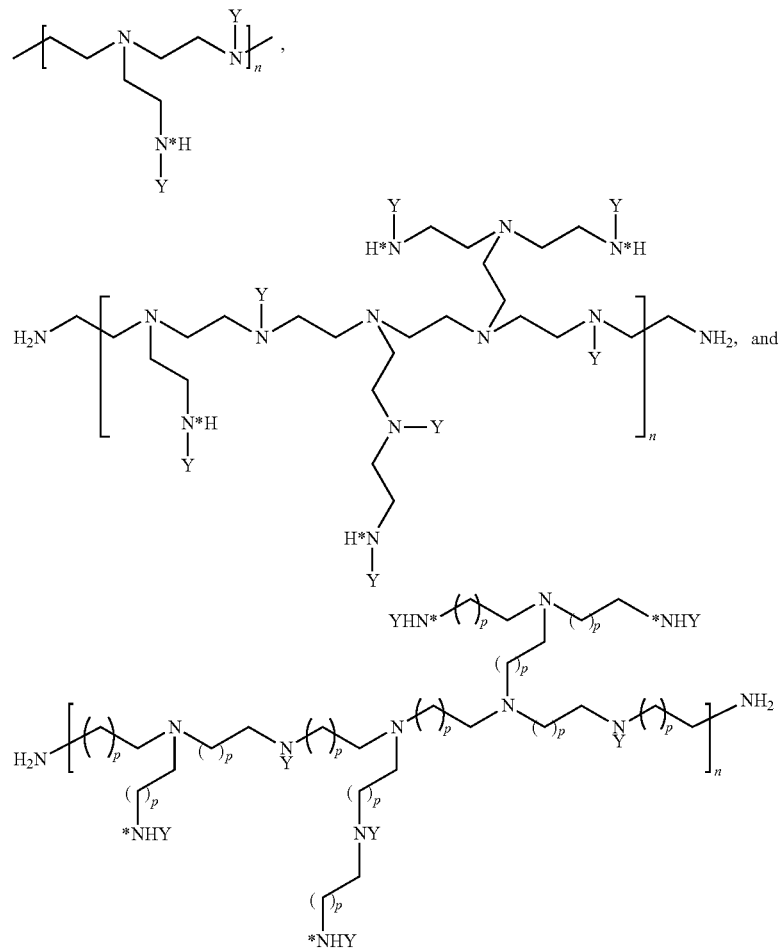

wherein, p is 1 or 2 and in each instance, n can be an integer as described elsewhere herein, and Y is a residue of Metformin having the formula:

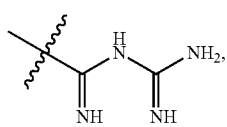

wherein, on one *N, Y" is shown as a residue of ethyl amine or propylamine, which can be further substituted; and,

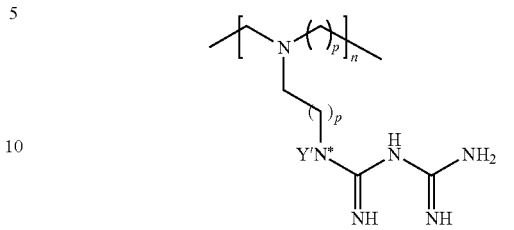

wherein, on one *N, Y" is shown as a residue of Metformin.

Each occurrence of *N is independent of any other occurrence of *N.

Mostly it is the primary *Ns initially present in the branched PEI that will be derivatized to Metformin moieties, which is meant to include monomethyl biguanides. Also because branch-chain PEIs contain mostly surface primary amines and the secondary and tertiary amines are internal, PolyMet may contain mostly surface monomethyl biguanide groups. As such, the physical and chemical properties of linear and branch-chain PolyMet can be adjusted utilizing the chemistries available on the PEI, PPI, polymer or dendrimer.

Accordingly, the amount of Metformin residues present in the polymer may also be described as the % wt of Metformin, excluding the backbone carbons, relative to the weight of the entire polymer. The % wt of Metformin in the PolyMet can be from 0.0001% wt/wt to above 90% wt/wt; at least 0.1% wt/wt; at least 0.5% wt/wt; at least 1% wt/wt; at least 2% wt/wt; at least 3% wt/wt; at least 4% wt/wt; at least 5% wt/wt; at least 10% wt/wt; at least 15% wt/wt; at least 20% wt/wt; at least 25% wt/wt; at least 30% wt/wt; at least 35% wt/wt; at least 40% wt/wt; at least 45% wt/wt; at least 50% wt/wt; at least 55% wt/wt; at least 60% wt/wt; at least 65% wt/wt; at least 70% wt/wt; at least 75% wt/wt; at least 80% wt/wt; and at least 85% wt/wt.

In embodiments, the PolyMet comprises a block copolymer, for example, PEI-PPI, and PEGylated block copolymers.

In embodiments, the block copolymers have the general formula:

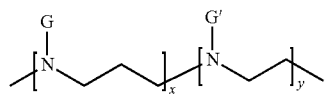

wherein x is from about 0.1 to about 0.9, y is from about 0.1 to about 0.9, and wherein x and y represent the mole fraction of each unit in the polymer and the sum of x and y is 1; both G and G' can be the same or different and in each instance is selected from the group consisting of:

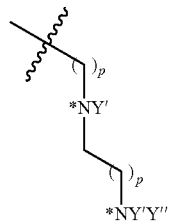

wherein p, *N, Y' and Y" are as shown above; hydrogen; a residue or Metformin; a residue of ethyl amine or propylamine, each of which can be further substituted with ethyl or propylamine, which can be further substituted and can contain a residue of Metformin, wherein the block copolymer has a % wt of covalently bound residues of Metformin from 0.001% wt/wt to above 90% wt/wt; from 0.01% wt/wt to about 80% wt/wt; from 1.0% wt/wt to about 70% wt/wt; from 2.0% wt/wt to about 60% wt/wt; from 3.0% wt/wt to about 50% wt/wt; from 4.0% wt/wt to about 40% wt/wt; from 5.0% wt/wt to about 30% wt/wt; or an amount above 0.001% but below about 60%, 50%, 40%; 30%, 20%, 10% or 5% wt/wt.

In embodiments, the PolyMet is a derivatized dendrimer. On the surface of dendrimer are primary amino groups. These primary amino groups, and potentially secondary amino groups as well, are the sites of derivitization of the dendrimer with the residues of metformin as described above to prepare a type of PolyMet. In embodiments, the subject matter described herein is directed to PolyMets comprising a Nitrogen on the dendrimer covalently bound to a residue of metformin. The derivatized dendrimer has the following structure:

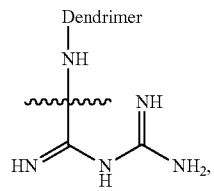

wherein at least 0.0001, 0.001, 0.01, 0.1, 2, 3, 4, 5, 10, 15, 20, 25, 30, 35, 40, 45, 50, 55, 60, 65, 70, 75, 80, 85, 90, 95 or about 100% of the occurrences of the primary Nitrogens of the dendrimer are derivatized by covalent bond to at least one residue of Metformin. In the structure above, in embodiments, some or all of the available secondary Nitrogen(s) on the dendrimer can also be derivatized with a residue of Metformin.

In some embodiments, the presently disclosed subject matter provides polypropylenimine (PPI) dendrimers, which comprise exterior or surface primary amines. These surface primary amines, and to an extent any exterior secondary amines and any interior or sub-surface primary and secondary amines can be derivatized to a metformin residue.

Any of the PolyMets described herein can be PEGylated and can also contain a targeting ligand. The percent PEGylation can be from about 0.001% to about 50% wt/wt of the PolyMet.

To test the characteristics of the PolyMet, three formulations can be performed. The first is to prepare (Lipid-Polycation-DNA) LPD using a negatively charged lipid such as dioleoyl phosphatidylserine (DOPS). The LPD will be prepared from a polyelectrolyte core complex with excess positive charges, i.e., the charge from PolyMet is in excess of DNA or hyaluronic acid. DOPS liposomes will then be added to wrap around the cores. However, branch-chain PolyMet can provide a different chemistry. The second formulation is to prepare (Liposome-Polycation-Hyaluronic acid) LPH, using a positive charged lipid such as 1,2-dipalmitoyl 3-trimethyl-ammonium propane (DPTAP). The LPH will be prepared by first forming a polyelectrolyte core complex with excess negative charges, i.e., the charge from DNA/siRNA or hyaluronic acid is in excess of PolyMet. DOTAP liposome will then be added to wrap around the core. The third formulation, the branched-chain PolyMet/pDNA complex without any lipid coating, can be prepared and tested to determine the transfection capability of the polyplex. This can determine if the proton sponge activity of the branched-chain PolyMet is sufficient to lyse the endosome and deliver DNA to the cytoplasm.

Useful molecular weights for PolyMet include from about 200 to about 6,000,000. The size of the PolyMet can be identified by the molecular weight of the polymer, PEI, PPI, etc. used to prepare the polymer. For example, a PEI having a MW of 4 k or repeat unit n=93 is used to prepare "PolyMet$_{93}$," which has MW of 12K. Useful PolyMets have MWs between about 100 (0.1 k) to about 6,000,000 (1000 k). These also include particular MWs from about 0.1 k to about 500 k; from about 0.1 k to about 300 k; from about 1 k to about 250 k; from about 1 k to about 200 k; from about 50 k to about 150 k; from about 1 k to about 120 k; from about 1 k to about 100 k; from about 1 k to about 80 k; from about 1 k to about 60 k; from about 1 k to about 50 k; from about 1 k to about 40 k; from about 1 k to about 30 k; from about 1 k to about 20 k from about 1 k to about 10 k; or from about 1 k to about 5 k. The length of the polymer can be readily adjusted using the methods described herein by manipulating the size of the polymer, PEI, PPI, etc. starting material. PolyMets of different MWs were systematically synthesized by using PEI of different MWs (from 4 k to 100 k) as the starting material.

The lengths of the PolyMet can be determinant on whether the PolyMet has the desired properties of a drug, a drug carrier (e.g., a cargo delivery vehicle) or both. The length of the PolyMet can be tuned to any particular type of cargo if the desired use is as a cargo delivery vehicle. For example, if the cargo is pDNA, the size of the PolyMet can be tailored accordingly. The ability of different PolyMet for pDNA transfection is assayed using a luciferase plasmid.

In embodiments, the subject matter disclosed herein is directed to cholesterol analogues having a covalently linked residue of Metformin.

Nanoparticles

As mentioned above, Metformin is the first line therapy for diabetes. However, its strong hydrophilic cationic properties cause rapid clearance from plasma, requiring multiple high doses for continued active plasma concentrations. Moreover, the PolyMet nanoparticles described herein can circulate in the body for a relatively extended time period as compared to Metformin, thereby decreasing the inconvenience of administering multiple doses over a period of time.

However, it is known that polycation complexes are not stable in the blood circulation (Chono, S., Li, S. D., Conwell, C. C. & Huang, L. An efficient and low immunostimulatory nanoparticle formulation for systemic siRNA delivery to the tumor. *Journal of Controlled Release* 131, 64-69 (2008)). As described elsewhere herein, LPH nanoparticles were prepared that contain a liposomal outer-layer to enhance the stability of polycomplex.

Nanoparticles, through both passive and active targeting, can enhance the intracellular concentration of drugs in cancer cells while avoiding toxicity in normal cells. Surface PEGylated nanoparticles can efficiently deliver nucleic acid, chemo-drugs and proteins to the solid tumors and metastatic sites. In embodiments where the surface of the nanoparticles is PEGylated, this can increase colloidal stability in circulation and reduce nonspecific uptake by the mononuclear phagocyte system (MPS). In some embodiments, these nanoparticles are also functionalized with anisamide (AA), to target the sigma receptor over expressed on tumor cells to facilitate cellular uptake. The in vitro and in vivo performance of these nanoparticles can be characterized in terms of tumor-targeted delivery of the bioactive compounds. Additionally, systemic toxicity can be examined to establish the safety of these nanoparticles.

In an embodiment, PolyMet is formed as an aggregate nanoparticle. The size of the aggregate nanoparticle is less than 1,000 nm, less than 500 nm, from about 50 nm to about 200 nm, or about 100 nm. The PolyMet aggregate nanoparticle can be complexed with a cargo, such as a therapeutic agent or biologic agent. Particularly useful PolyMet nanoparticles comprise PolyMet/nucleotide complexes, for example, PolyMet/pDNA complexes.

In an embodiment, PolyMet is part of a liposome-polycation-hyaluronic acid (LPH) nanoparticle. These nanoparticles are referred to herein as "LPH-PolyMets." In this embodiment, the subject matter described herein is directed to a nanoparticle comprising:

i. a lipid outer membrane; and
ii. PolyMet encapsulated by the lipid outer membrane.

The PolyMet can be complexed or associated with a cargo, such as a therapeutic agent or biologic agent. As used herein, the term "complexed" or "associated" means that the cargo and the PolyMet are in intimate contact with each other.

Particular cargos for complexing or associating with PolyMet include therapeutic agents, bioactive compounds and the like, such as anti-cancer drugs and biologics. Therapeutic agents include bioactive compounds, such as polynucleotides, polypeptides, polysaccharides, organic and inorganic small molecules. The term "bioactive compound" encompasses both naturally occurring and synthetic bioactive compounds. The term "bioactive compound" can refer to a detection or diagnostic agent that interacts with a biological molecule to provide a detectable readout that reflects a particular physiological or pathological event. Therapeutic agents include chemotherapeutic drugs. In other embodiments, the therapeutic agent is a polynucleotide of interest or a polypeptide of interest, such as a silencing element (e.g., siRNA).

When the therapeutic agent is a drug, it includes but is not limited to, antimicrobials, antibiotics, antimycobacterials, antifungals, antivirals, neoplastic agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholinergics, anticholinergics, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenics, non-steroidal anti-inflammatory agents, steroidal anti-inflammatory agents, antioxidants, vaso-active agents, bone-active agents, antiarthritics, and diagnostic agents. Preferred antiviral drugs include tenofovir, adefovir, acyclovir monophosphate and L-thymidine monophosphate. In a preferred embodiment, the bioactive compound is an anticancer drug.

An anticancer drug or "chemotherapeutic agent" is a chemical compound useful in the treatment of cancer. Examples of chemotherapeutic agents include alkylating agents such as thiotepa and cyclophosphamide (CYTOXAN®); alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; pemetrexed; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; TLK-286; CDP323, an oral alpha-4 integrin inhibitor; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gamma1I and calicheamicin omega1I (see, e.g., Nicolaou et al., *Angew. Chem Intl. Ed. Engl.,* 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, and floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Additional examples of chemotherapeutic agents include anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); antisense oligonucleotides, particularly those that inhibit expression of genes in signaling pathways implicated in abherrant cell proliferation, such as, for example, PKC-alpha, Raf, H-Ras, and epidermal growth factor receptor (EGFR); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); an anti-estrogen such as fulvestrant; EGFR inhibitor such as erlotinib or cetuximab; an anti-VEGF inhibitor such as bevacizumab; arinotecan; rmRH (e.g., ABARELIX®); 17AAG (geldanamycin derivative that is a heat shock protein (Hsp) 90 poison), and pharmaceutically acceptable salts, acids or derivatives of any of the above.

Particular anticancer drugs include rapamycin, cisplatin and its analogues, etoposide monophosphate, alendronate, pamidronate, and gemcitabine monophosphate and salts, esters, conformers and produgs thereof.

The nanoparticle can further comprise hyaluronic acid and/or nucleic acids encapsulated in the liposome and optionally complexed with the PolyMet therein.

The "lipid outer membrane" is a largely contiguous layer that comprises a lipid, in particular, a cationic lipid. The lipid outer membrane may further comprise a targeting ligand and/or polyethylene glycol (PEG).

As used herein, the term "lipid" refers to a member of a group of organic compounds that has lipophilic or amphipathic properties, including, but not limited to, fats, fatty oils, essential oils, waxes, steroids, sterols, phospholipids, glycolipids, sulpholipids, aminolipids, chromolipids (lipochromes), and fatty acids. The term "lipid" encompasses both naturally occurring and synthetically produced lipids. Particular lipids include DOTAP, DOPS and cholesterol.

Lipids can include cationic lipids. As used herein, the term "cationic lipid" encompasses any of a number of lipid species that carry a net positive charge at physiological pH, which can be determined using any method known to one of skill in the art. Such lipids include, but are not limited to, the cationic lipids of formula (I) disclosed in International Application No. PCT/US2009/042476, entitled "Methods and Compositions Comprising Novel Cationic Lipids," which was filed on May 1, 2009, and is herein incorporated by reference in its entirety. These include, but are not limited to, N-methyl-N-(2-(arginoylamino)ethyl)-N, N-Di octadecyl aminium chloride or di stearoyl arginyl ammonium chloride] (DSAA), N,N-di-myristoyl-N-methyl-N-2[N'-(N$^6$-guanidino-L-lysinyl)] aminoethyl ammonium chloride (DMGLA), N,N-dimyristoyl-N-methyl-N-2[N$^2$-guanidino-L-lysinyl] aminoethyl ammonium chloride, N,N-dimyristoyl-N-methyl-N-2[N'-(N2,N6-di-guanidino-L-lysinyl)] aminoethyl ammonium chloride, and N,N-di-stearoyl-N-methyl-N-2[N'-(N6-guanidino-L-lysinyl)] aminoethyl ammonium chloride (DSGLA). Other non-limiting examples of cationic lipids that can be present include N,N-dioleyl-N,N-dimethylammonium chloride ("DODAC"); N-(2,3-dioleoyloxy)propyl)-N,N,N-trimethylammonium chloride ("DOTAP"); N-(2,3-dioleyloxy) propyl)-N,N,N-trimethylammonium chloride ("DOTMA") or other N-(N,N-1-dialkoxy)-alkyl-N,N,N-trisubstituted ammonium surfactants; N,N-distearyl-N,N-dimethylammonium bromide ("DDAB"); 3-(N-(N',N'-dimethylaminoethane)-carbamoyl) cholesterol ("DC-Chol") and N-(1,2-dimyristyloxyprop-3-yl)-N,N-dimethyl-N-hydroxyethyl ammonium bromide ("DMRIE"); 1,3-dioleoyl-3-trimethylammonium-propane, N-(1-(2,3-dioleyloxy)propyl)-N-(2-(sperminecarboxamido)ethyl)-N,N-dimethy-1 ammonium trifluoro-acetate (DOSPA); GAP-DLRIE; DMDHP; 3-β[$^4$N-($^1$N,$^8$N-diguanidinospermidine)-carbamoyl] cholesterol (BGSC); 3-β[N,N-diguanidinoethyl-aminoethane)-carbamoyl] cholesterol (BGTC); N,N$^1$,N$^2$,N$^3$ Tetra-methyltetrapalmityl-spermine (cellfectin); N-t-butyl-N'-tetradecyl-3-tetradecyl-aminopropion-amidine (CLONfectin); dimethyldioctadecyl ammonium bromide (DDAB); 1,3-dioleoyloxy-2-(6-carboxyspermyl)-propyl amide (DOSPER); 4-(2,3-bis-palmitoyloxy-propyl)-1-methyl-1H-imidazole (DPIM) N,N,N',N'-tetramethyl-N,N'-bis(2-hydroxyethyl)-2,3 dioleoyloxy-1,4-butanediammonium iodide) (Tfx-50); 1,2 dioleoyl-3-(4'-trimethylammonio) butanol-sn-glycerol (DOBT) or cholesteryl (4'trimethylammonia) butanoate (ChOTB) where the trimethylammonium group is connected via a butanol spacer arm to either the double chain (for DOTB) or cholesteryl group (for ChOTB); DL-1,2-dioleoyl-3-dimethylaminopropyl-β-hydroxyethylammonium (DORI) or DL-1,2-O-dioleoyl-3-dimethylaminopropyl-β-hydroxyethylammonium (DORIE) or analogs thereof as disclosed in International Application Publication No. WO 93/03709, which is herein incorporated by reference in its entirety; 1,2-dioleoyl-3-succinyl-sn-glycerol choline ester (DOSC); cholesteryl hemisuccinate ester (ChOSC); lipopolyamines such as dioctadecylamidoglycylspermine (DOGS) and dipalmitoyl phosphatidylethanolamylspermine (DPPES) or the cationic lipids disclosed in U.S. Pat. No. 5,283,185, which is herein incorporated by reference in its entirety; cholesteryl-3β-carboxyl-amido-ethylenetrimethylammonium iodide; 1-dimethylamino-3-trimethylammonio-DL-2-propyl-cholesteryl carboxylate iodide; cholesteryl-3-β-carboxyamidoethyleneamine; cholesteryl-3-β-oxysuccinamido-ethylenetrimethylammonium iodide; 1-dimethylamino-3-trimethylammonio-DL-2-propyl-cholesteryl-3-β-oxysuccinate iodide; 2-(2-trimethylammonio)-ethylmethylamino ethyl-cholesteryl-3-β-oxysuccinate iodide; and 3-β-N-(polyethyleneimine)-carbamoylcholesterol.

The lipids can contain co-lipids that are negatively charged or neutral. As used herein, a "co-lipid" refers to a non-cationic lipid, which includes neutral (uncharged) or anionic lipids. The term "neutral lipid" refers to any of a number of lipid species that exist either in an uncharged or neutral zwitterionic form at physiological pH. The term "anionic lipid" encompasses any of a number of lipid species that carry a net negative charge at physiological pH.

Co-lipids can include, but are not limited to, diacylphosphatidylcholine, diacylphosphatidylethanolamine, ceramide, sphingomyelin, cephalin, cholesterol, cerebrosides and diacylglycerols, phospholipid-related materials, such as lecithin, phosphatidylethanolamine, lysolecithin, lysophosphatidylethanolamine, phosphatidylserine, phosphatidylinositol, cardiolipin, phosphatidic acid, dicetylphosphate, distearoylphosphatidylcholine (DSPC), dioleoyl-phosphatidylcholine (DOPC), dipalmitoylphosphatidylcholine (DPPC), dioleoylphosphatidylglycerol (DOPG), palmitoyloleyolphosphatidylglycerol (POPG), dipalmitoyl-phosphatidylglycerol (DPPG), dioleoyl-phosphatidylethanolamine (DOPE), palmitoyloleoylphosphatidylchol-ine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dioleoyl phosphatidic acid (DOPA), stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, lysophosphatidylcholine, and dioctadecyldimethyl ammonium bromide and the like. Co-lipids also include polyethylene glycol-based polymers such as PEG 2000, PEG 5000 and polyethylene glycol conjugated to phospholipids or to ceramides, as described in U.S. Pat. No. 5,820,873, herein incorporated by reference in its entirety.

Preferably, the amphiphilic lipid having a free phosphate group is dioleoyl phosphatidic acid (DOPA).

The surface of the nanoparticles can be PEGylated. The term "polymer-PEG conjugate" also refers to these polymer-PEG-targeting ligand conjugates and nanoparticles comprising a polymer-PEG targeting ligand conjugate. PEGylation enhances the circulatory half-life by reducing clearance of the nanoparticles by the reticuloendothelial (RES) system.

In some of those embodiments, the surface comprises a polymer-PEG conjugate at a concentration of about 4 mol % to about 15 mol % of the surface, including, but not limited to, about 4 mol %, about 5 mol %, about 6 mol %, about 7 mol %, 8 mol %, about 9 mol %, about 10 mol %, about 11 mol %, about 12 mol %, about 13 mol %, about 14 mol %, and about 15 mol % PEG. Higher percentage values (expressed in mol %) of PEG have also been found to be useful. Useful mol % values include those from about 12 mol % to about 50 mol %. Preferably, the values are from about 15 mol % to about 40 mol %. Also preferred are values from about 15 mol % to about 35 mol %. Most preferred values are from about 20 mol % to about 25 mol %, for example 23 mol %.

The polyethylene glycol moiety of the lipid-PEG conjugate can have a molecular weight ranging from about 100 to about 20,000 g/mol, including but not limited to about 100 g/mol, about 200 g/mol, about 300 g/mol, about 400 g/mol, about 500 g/mol, about 600 g/mol, about 700 g/mol, about 800 g/mol, about 900 g/mol, about 1000 g/mol, about 5000 g/mol, about 10,000 g/mol, about 15,000 g/mol, and about 20,000 g/mol. In some embodiments, the lipid-PEG conjugate comprises a PEG molecule having a molecular weight of about 2000 g/mol. In certain embodiments, the lipid-PEG conjugate comprises DSPE-PEG$_{2000}$.

In some embodiments, the surface comprises a targeting ligand, thereby forming a targeting nanoparticle. By "targeting ligand" is intended a molecule that targets a physically associated molecule or complex to a targeted cell or tissue. As used herein, the term "physically associated" refers to either a covalent or non-covalent interaction between two molecules.

Targeting ligands can include, but are not limited to, small molecules, peptides, lipids, sugars, oligonucleotides, hormones, vitamins, antigens, antibodies or fragments thereof, specific membrane-receptor ligands, ligands capable of reacting with an anti-ligand, fusogenic peptides, nuclear localization peptides, or a combination of such compounds. Non-limiting examples of targeting ligands include asialoglycoprotein, insulin, low density lipoprotein (LDL), folate, benzamide derivatives, peptides comprising the arginine-glycine-aspartate (RGD) sequence, and monoclonal and polyclonal antibodies directed against cell surface molecules. In some embodiments, the small molecule comprises a benzamide derivative. In some of these embodiments, the benzamide derivative comprises anisamide.

Some targeting ligands comprise an intervening molecule in between the surface and the targeting ligand, which is covalently bound to both the surface and the targeting ligand. In some of these embodiments, the intervening molecule is polyethylene glycol (PEG).

By "targeted cell" is intended the cell to which a targeting ligand recruits a physically associated molecule or complex. The targeting ligand can interact with one or more constituents of a target cell. The targeted cell can be any cell type or at any developmental stage, exhibiting various phenotypes, and can be in various pathological states (i.e., abnormal and normal states). For example, the targeting ligand can associate with normal, abnormal, and/or unique constituents on a microbe (i.e., a prokaryotic cell (bacteria), viruses, fungi, protozoa or parasites) or on a eukaryotic cell (e.g., epithelial cells, muscle cells, nerve cells, sensory cells, cancerous cells, secretory cells, malignant cells, erythroid and lymphoid cells, stem cells). Thus, the targeting ligand can associate with a constituent on a target cell which is a disease-associated antigen including, for example, tumor-associated antigens and autoimmune disease-associated antigens. Such disease-associated antigens include, for example, growth factor receptors, cell cycle regulators, angiogenic factors, and signaling factors.

In some embodiments, the targeting ligand interacts with a cell surface protein on the targeted cell. In some of these embodiments, the expression level of the cell surface protein that is capable of binding to the targeting ligand is higher in the targeted cell relative to other cells. For example, cancer cells overexpress certain cell surface molecules, such as the HER2 receptor (breast cancer) or the sigma receptor. In certain embodiments wherein the targeting ligand comprises a benzamide derivative, such as anisamide, the targeting ligand targets the associated nanoparticles to sigma-receptor overexpressing cells, which can include, but are not limited to, cancer cells such as small- and non-small-cell lung carcinoma, renal carcinoma, colon carcinoma, sarcoma, breast cancer, melanoma, glioblastoma, neuroblastoma, and prostate cancer (Aydar, Palmer, and Djamgoz (2004) *Cancer Res.* 64:5029-5035).

The LPH-PolyMet nanoparticles can be of any size, so long as they are capable of delivering the cargo to a cell (e.g., in vitro, in vivo), physiological site, or tissue. As used herein, the term "nanoparticle" refers to particles of any shape having at least one dimension that is less than about 1000 nm. In some embodiments, nanoparticles have at least one dimension in the range of about 1 nm to about 1000 nm, including any integer value between 1 nm and 1000 nm (including about 1, 2, 5, 10, 20, 30, 40, 50, 60, 70, 80, 90, 100, 200, 500, and 1000). In certain embodiments, the nanoparticles have at least one dimension that is about 150 nm. Spherical nanoparticles can have a diameter of less than about 100 nm, including but not limited to about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, and 100 nm. In particular embodiments, the nanoparticles have a diameter of less than about 50 nm. In particular embodiments, the nanoparticles have a diameter of between about 40 nm and about 50 nm.

In some embodiments, particularly those in which the diameter of the nanoparticles is less than 100 nm, the nanoparticles can be used to deliver bioactive compounds across the blood-brain barrier (BBB) into the central nervous system or across the placental barrier. Non-limiting examples of targeting ligands that can be used to target the BBB include transferring and lactoferrin (Huang et al. (2008) *Biomaterials* 29(2):238-246, which is herein incorporated by reference in its entirety). Further, the nanoparticles can be transcytosed across the endothelium into both skeletal and cardiac muscle cells. For example, exon-skipping oligonucleotides can be delivered to treat Duchene muscular dystrophy (Moulton et al. (2009) *Ann N Y Acad Sci* 1175:55-60, which is herein incorporated by reference in its entirety).

Particle size can be determined using any method known in the art, including, but not limited to, sedimentation field flow fractionation, photon correlation spectroscopy, disk centrifugation, and dynamic light scattering (using, for example, a submicron particle sizer such as the NICOMP particle sizing system from AutodilutePAT Model 370; Santa Barbara, Calif.).

In particular embodiments, the nanoparticles described herein can have a zeta potential of from about −20 mV to +20 mV. In some embodiments, the nanoparticles have a zeta potential of less than −10 mV and in certain embodiments, the zeta potential is from about +10 mV to about +20 mV, including but not limited to about +14 mV, about +15 mV, about +16 mV, about +17 mV, about +18 mV, about +19 mV, and about +20 mV.

The nanoparticles described herein can be self-assembling, substantially spherical vesicles. The nanoparticle can further comprise one or more different polymers in addition to PolyMet. Useful polymers include known polymers that are biocompatible. The term "biocompatible" is used herein as it is used in the art to describe polymers that are appropriate for pharmaceutical use. Biocompatible polymers may be bioresorptive polymers that degrade and are absorbed by the body over time.

Polymer refers to a chemical compound or mixture of compounds formed by polymerization and consisting essentially of repeating structural units. Useful polymers can be synthetic materials used in vivo or in vitro that are capable of forming the nanoparticles and are intended to interact with a biological system. These include, but are not limited to those taught in U.S. Pat. No. 5,514,378 (incorporated herein by reference). Biodegradable copolymers have also been described, including aliphatic polyester, polyorthoester, polyanhydride, poly alpha-amino acid, polyphosphagen, and polyalkylcyanoacrylate. Among aliphatic polyesters, polylactide (PLA), polyglycolide (PGA) and polylactideglycolide (PLGA). Biodegradable polymers include lactic acid polymers such as poly(L-lactic acid) (PLLA), poly(DL-lactic acid) (PLA), and poly(DL-lactic-co-glycolic acid) (PLGA). The co-monomer (lactide:glycolide) ratios of the poly(DL-lactic-co-glycolic acid) are preferably between 100:0 and 50:50. Most preferably, the co-monomer ratios are between 85:15 (PLGA 85:15) and 50:50 (PLGA 50:50). Blends of PLLA with PLGA, preferably PLGA 85:15 and PLGA 50:50, can be used. A particularly useful polymer is poly(lactic-co-glycolic acid) (PLGA).

Metformin has anti-tumor efficacy (Morales; Kisfalvi, K., Moro, A., Sinnett-Smith, J., Eibl, G. & Rozengurt, E. Metformin inhibits the growth of human pancreatic cancer xenografts. *Pancreas* 42, 781-785 (2013)). LPH nanoparticles containing PolyMet (LPH-PolyMet) can synergistically inhibit tumor growth. Presented herein are studies of the effect of LPH-PolyMet and different nanoparticles on H460 xenograft.

Figure 6A:
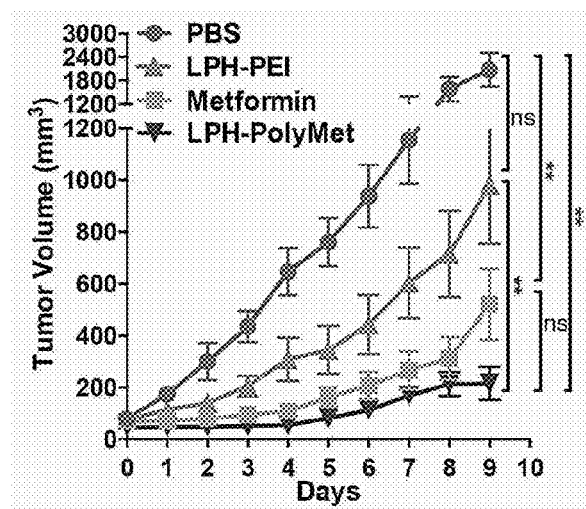
FIG. 6A depicts Metformin and PolyMet inhibit H460 tumor growth. PBS, metformin, LPH-PEI and LPH-PolyMet were administered intravenously every other day, and mice were sacrificed 24 hours after the final injection.
Figure 6B:
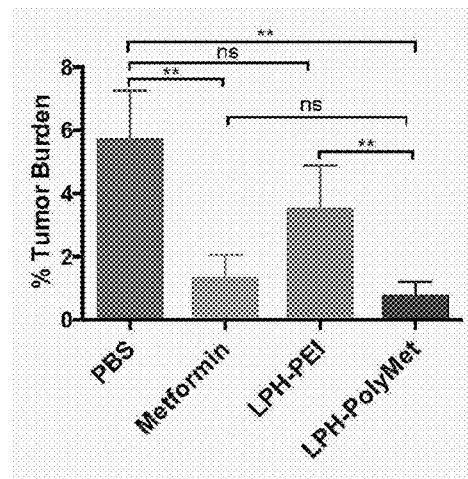
FIG. 6B depicts tumor weights were measured on day after final injection and compared with body weights to determine percentage of tumor burden.
Figure 6C:
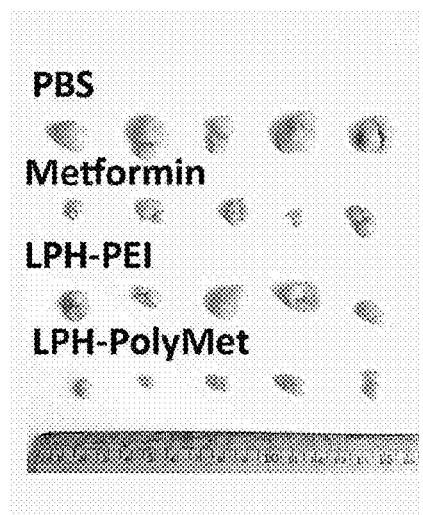
FIG. 6C depicts visual observations of the H460 tumor sizes in each treatment group at the end time point; (n=5 per group).

As shown in FIG. 6, treatment with metformin or LPH-PolyMet led to significant inhibition of cancer progression in comparison with PBS and LPH-PEI groups, which primarily resulted from the anti-tumor efficacy of metformin in either free or polymer form. Importantly, the dose of metformin and PolyMet for IV injections was 0.4 mg/kg body weight, which is substantially less than the previous studies used through IV administration routes (Shi, W. Y. et al. Therapeutic metformin/AMPK activation blocked lymphoma cell growth via inhibition of mTOR pathway and induction of autophagy. *Cell Death Dis* 3 (2012)). However, previous reports indicated that low-dose metformin was able to sufficiently inhibit tumor growth (Hu, T. et al. Reprogramming ovarian and breast cancer cells into non-cancerous cells by low-dose metformin or SN-38 through FOXO3 activation. *Scientific reports* 4 (2014); Gou, S. M. et al. Low Concentrations of Metformin Selectively Inhibit CD133(+) Cell Proliferation in Pancreatic Cancer and Have Anticancer Action. *PloS one* 8 (2013)). A noticeable difference in tumor growth inhibition was observed between the LPH-PEI and LPH-PolyMet (FIG. 6), suggesting that the PolyMet plays an important role in enhancing antitumor activity. After the last treatment, the tumor sizes of the xenografts treated with LPH-PolyMet were less than 1% of the total body weight, which was significantly smaller than LPH-PEI (4%) and PBS (6%) groups (FIG. 6B).

Figure 5B:
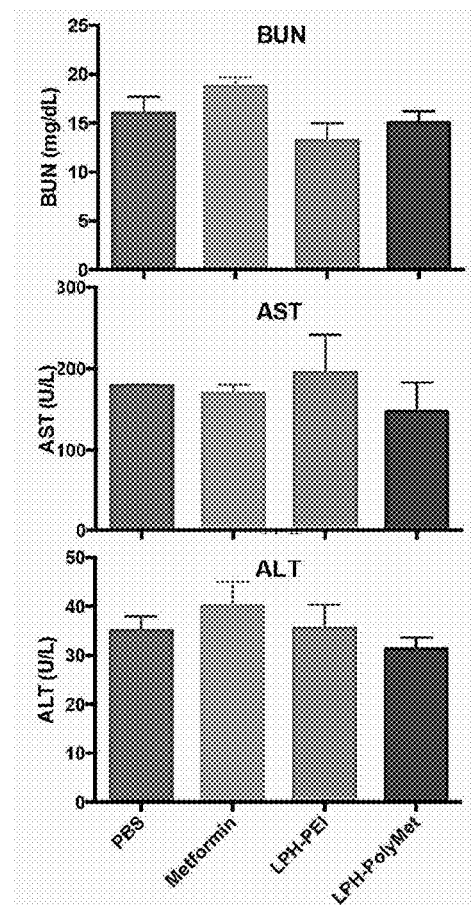
FIG. 5B depicts blood biochemistry test of serum.
Figure 5C:
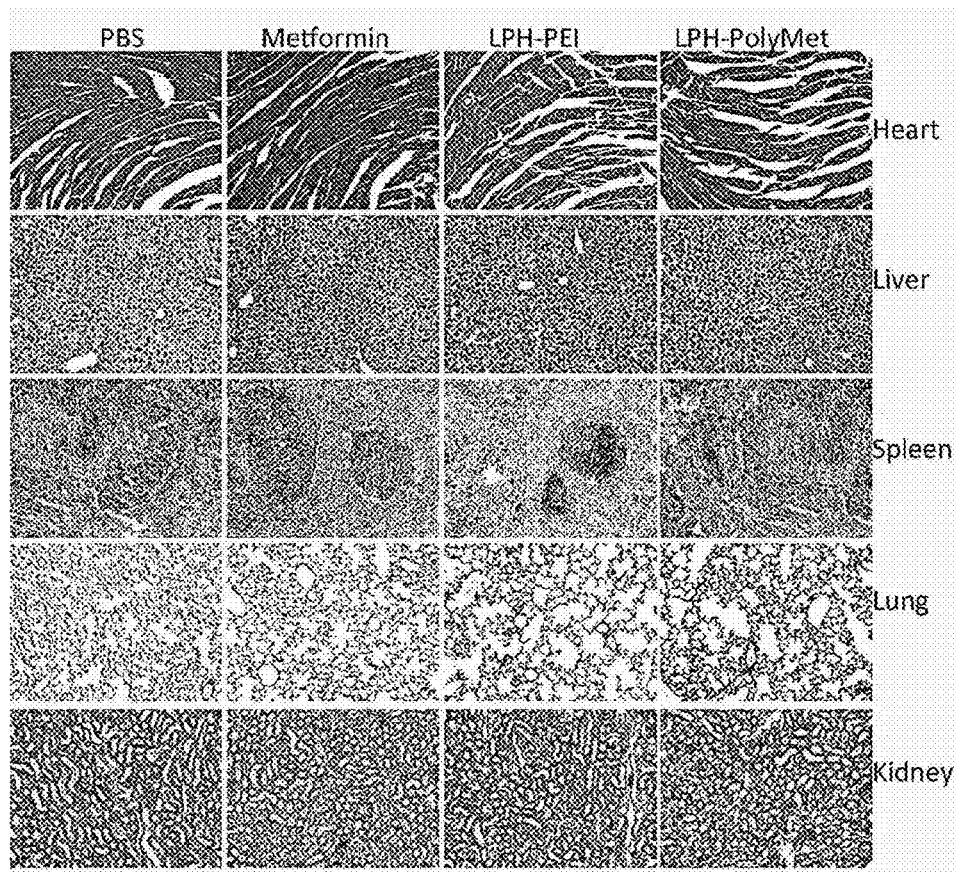
FIG. 5C depicts H&E staining of major organs collected from after injections of PBS, Metformin, LPH-PEI and LPH-PolyMet. Data are mean±S.D. (n=5 per group).

No toxicity in blood hematology, serum chemistry or major tissues (FIG. 5) was observed. It has been previously reported that metformin inhibition effects cancer viability by activating the AMP-activated protein kinase (AMPK) and inhibiting the mammalian target of rapamycin (mTOR) pathways (Dowling, R. J., Zakikhani, M., Fantus, I. G., Pollak, M. & Sonenberg, N. Metformin inhibits mammalian target of rapamycin-dependent translation initiation in breast cancer cells. *Cancer research* 67, 10804-10812 (2007); Yue, W., Yang, C. S., DiPaola, R. S. & Tan, X. L. Repurposing of metformin and aspirin by targeting AMPK-mTOR and inflammation for pancreatic cancer prevention and treatment. *Cancer prevention research* 7, 388-397 (2014)). PolyMet can have the same mechanism for cancer inhibition. AMPK acts as a metabolic tumor suppressor that governs glucose and lipid metabolism (LeRoith, D. Insulin-like growth factors and cancer: from basic biology to therapeutics. Humana Press, New York; 2012). In many cases, a low level of phosphorylation of AMPK is correlated with poor prognosis after treatments (Zulato, E. et al. Prognostic significance of AMPK activation in advanced stage colorectal cancer treated with chemotherapy plus bevacizumab. *British journal of cancer* 111, 25-32 (2014).

Figure 7A:
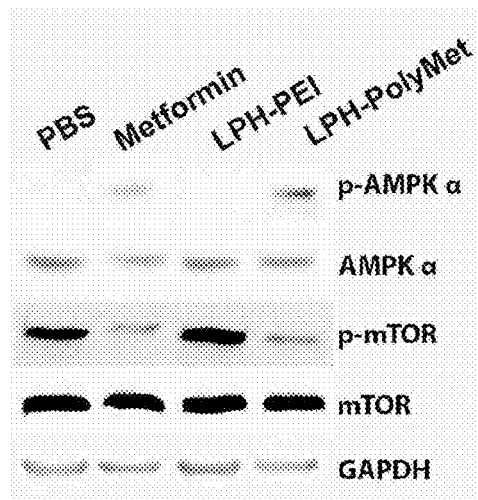
FIG. 7A depicts Metformin and PolyMet inhibition of tumor growth by activation of AMPK, inhibiting the mTOR pathway.

It was observed that following treatments with metformin and LPH-PolyMet, phosphorylation levels of AMPKα were sustainably enhanced about 9 and 12 fold than PBS group respectively, indicating the stimulation of AMPK activity (FIG. 7A); however, the activation of AMPKα did not occur in LPH-PEI group. This suggests that PolyMet is the key factor in the nanoparticle that can activate the AMPKα pathway. mTOR is a downstream effector of AMPK (Kimura, N. et al. A possible linkage between AMP-activated protein kinase (AMPK) and mammalian target of rapamycin (mTOR) signalling pathway. *Genes Cells* 8, 65-79 (2003). AMPK activation inhibits mTOR and its downstream effector kinases (Bolster, D. R., Crozier, S. J., Kimball, S. R. & Jefferson, L. S. AMP-activated protein kinase suppresses protein synthesis in rat skeletal muscle through down-regulated mammalian target of rapamycin (mTOR) signaling. *J Biol Chem* 277, 23977-23980 (2002)).

Phosphorylation of mTOR plays a pivotal role in the proliferation and survival of cancer cells (Matsubara, S. et al. mTOR plays critical roles in pancreatic cancer stem cells through specific and sternness-related functions. *Scientific reports* 3, 3230 (2013)). Therefore, the effects of metformin and LPH-PolyMet on the activity of mTOR (FIG. 7A) was evaluated. Metformin and LPH-PolyMet treatments led to a significant inhibition of mTOR activity indicated by a 2.3-fold and 2.9-fold reduction in p-mTOR/mTOR levels compared to the PBS and LPH-PEI respectively.

Figure 7B:
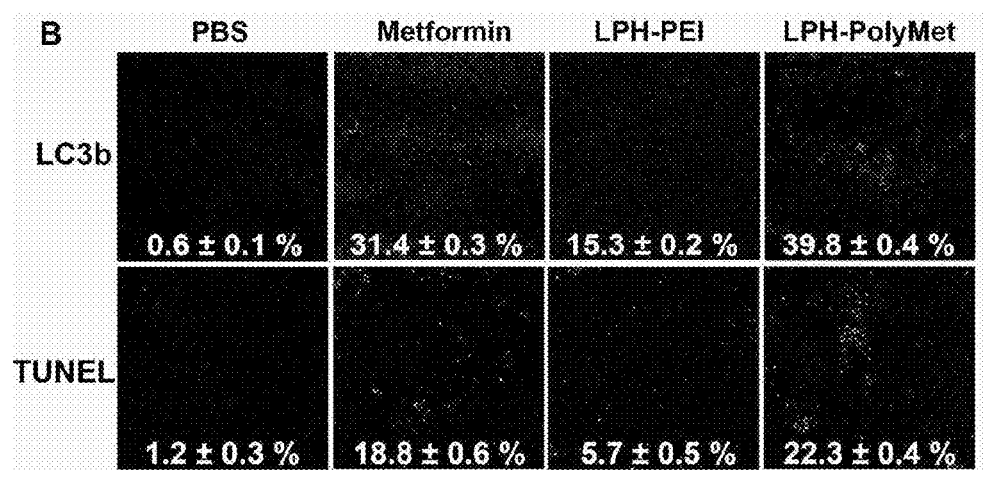

Autophagy is recognized as a potentially toxic mechanism for metformin that results in the inhibition of cancer growth (Tomic, T. et al. Metformin inhibits melanoma development through autophagy and apoptosis mechanisms. *Cell Death Dis* 2 (2011); Feng, Y. et al. Metformin promotes autophagy and apoptosis in esophageal squamous cell carcinoma by downregulating Stat3 signaling. *Cell Death Dis* 5 (2014)). We therefore evaluated whether autophagy can also be observed after treatment of PolyMet. Microtubule-associated protein light chain 3 b (LC3b) is a specific marker for autophagy initiation (Mizushima, N., Yoshimori, T. & Levine, B. Methods in mammalian autophagy research. *Cell* 140, 313-326 (2010)). As shown in FIG. 7B, metformin and LPH-PolyMet treated tumors showed a higher LC3b-associated red fluorescence than other groups, indicating that metformin and LPH-PolyMet can induce autophagy in lung xenograft.

Next, the mechanism of the anti-tumor effect after treatments was assayed by the TUNEL assay (FIG. 7B). The percent of apoptotic cells after metformin and LPH-PolyMet treatments was 18.8% and 32.3% respectively, while no significant apoptosis induction was observed in other groups. This suggests that metformin in the free form or polymer form can induce cell apoptosis and play a critical role in regulating the cancer cell survivals. In summary, both metformin and PolyMet inhibition of H460 lung cancer development was mediated by both autophagy and apoptosis mechanisms.

Methods of Treatment

In an embodiment, the present subject matter is directed to methods of treating a disease by administering PolyMet or LPH-PolyMet to a subject. In these embodiments, the methods can comprise administering to a subject in need of treatment an effective amount of PolyMet or LPH-PolyMet to achieve the desired treatment effect.

The disease or unwanted condition to be treated can encompass any type of condition or disease that can be treated therapeutically. In particular, in these embodiments, the disease to be treated can be a metabolic disorder, a genetic disorder and/or cancer. In some embodiments, the disease or unwanted condition that is to be treated is diabetes. In some embodiments, the disease or unwanted condition that is to be treated is a cancer.

As described elsewhere herein, the term "cancer" encompasses any type of unregulated cellular growth and includes all forms of cancer. In some embodiments, the cancer to be treated is a metastatic cancer. In particular, the cancer may be resistant to known therapies. Methods to detect the inhibition of cancer growth or progression are known in the art and include, but are not limited to, measuring the size of the primary tumor to detect a reduction in its size, delayed appearance of secondary tumors, slowed development of secondary tumors, decreased occurrence of secondary tumors, and slowed or decreased severity of secondary effects of disease.

Thus, in some embodiments, the PolyMet or LPH-PolyMet is targeting is a cancer cell. The terms "cancer" or "cancerous" refer to or describe the physiological condition in mammals that is typically characterized by unregulated cell growth. The cancerous cells can be capable of local invasion and/or metastasis to noncontiguous sites. The term "cancer" encompasses all types of cancers, including, but not limited to, all forms of carcinomas, melanomas, sarcomas, lymphomas and leukemias, including without limitation, bladder carcinoma, brain tumors, breast cancer, cervical cancer, colorectal cancer, esophageal cancer, endometrial cancer, hepatocellular carcinoma, laryngeal cancer, lung cancer, osteosarcoma, ovarian cancer, pancreatic cancer, prostate cancer, renal carcinoma, thyroid cancer, acute lymphocytic leukemia, acute myeloid leukemia, ependymoma, Ewing's sarcoma, glioblastoma, medulloblastoma, neuroblastoma, osteosarcoma, rhabdomyosarcoma, rhabdoid cancer, and nephroblastoma (Wilm's tumor).

The PolyMet or LPH-PolyMet optionally containing an additional therapeutic agent can be used for the treatment of a disease or unwanted condition in a subject, wherein the bioactive compound has therapeutic activity against the disease or unwanted condition when expressed or introduced into a cell. The bioactive compound is administered to the subject in a therapeutically effective amount. In those embodiments wherein the bioactive compound comprises a polynucleotide, when the polynucleotide of interest is administered to a subject in therapeutically effective amounts, the polynucleotide of interest or the polypeptide encoded thereby is capable of treating the disease or unwanted condition.

It will be understood by one of skill in the art that the PolyMet or LPH-PolyMet can be used alone or in conjunction with other therapeutic modalities, including, but not limited to, surgical therapy, radiotherapy, or treatment with any type of therapeutic agent, such as a drug. In those embodiments in which the subject is afflicted with cancer, the PolyMet or LPH-PolyMet can be delivered in combination with any chemotherapeutic agent well known in the art.

By "therapeutic activity" when referring to a bioactive compound is intended that the molecule is able to elicit a desired pharmacological or physiological effect when administered to a subject in need thereof.

As used herein, the terms "treatment" or "prevention" refer to obtaining a desired pharmacologic and/or physiologic effect. The effect may be prophylactic in terms of completely or partially preventing a particular infection or disease or sign or symptom thereof and/or may be therapeutic in terms of a partial or complete cure of an infection or disease and/or adverse effect attributable to the infection or the disease. Accordingly, the method "prevents" (i.e., delays or inhibits) and/or "reduces" (i.e., decreases, slows, or ameliorates) the detrimental effects of a disease or disorder in the subject receiving the compositions of the invention.

As used herein, the "subject" may be any animal, including a mammal, such as a human, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use. The subject in need of treatment for a disease or unwanted condition may be a person demonstrating symptoms of such disease or condition, a subject that has been diagnosed, a subject that is in remission, or a subject having an increased risk for developing the disease or condition (e.g., a genetic predisposition, certain dietary or environmental exposures).

An "effective amount" is at least the minimum concentration required to effect a measurable improvement or prevention of a particular disorder. An effective amount herein may vary according to factors such as the disease state, age, sex, and weight of the patient, and the ability of the antibody to elicit a desired response in the subject. Thus, the dosage administered to a subject will depend on a number of other factors including the method and site of administration, patient age, weight and condition. Those of ordinary skill in the art can readily adjust dosages for a given type of administration, a given patient and for a given therapeutic application.

An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. An effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

In some embodiments, the PolyMet or LPH-PolyMet are administered to the subject at a dose of between about 0.001 µg/kg and about 1000 mg/kg, including but not limited to about 0.001 µg/kg, 0.01 µg/kg, 0.05 µg/kg, 0.1 µg/kg, 0.5 µg/kg, 1 µg/kg, 10 µg/kg, 25 µg/kg, 50 µg/kg, 100 µg/kg, 250 µg/kg, 500 µg/kg; 5 mg/kg, 10 mg/kg, 25 mg/kg, 50 mg/kg, 100 mg/kg, and 200 mg/kg; or from about 0.01 mg/kg to 10 mg/kg; 0.05 mg/kg to 5 mg/kg; 0.07 mg/kg to 2 mg/kg; 0.1 mg/kg to 0.9 mg/kg; 0.2 mg/kg to 0.7 mg/kg; 0.3 mg/kg to 0.5 mg/kg.

In some of the embodiments wherein the PolyMet or LPH-PolyMet has a biologic cargo, they may be administered to the subject at a dose of between about 0.01 mg/kg and about 1000 mg/kg, including but not limited to about 0.01 mg/kg, 0.05 mg/kg, 0.1 mg/kg, 0.5 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 25 mg/kg, 50 mg/kg, 100 mg/kg, and 250 mg/kg; or from about 0.01 mg/kg to 10 mg/kg; 0.05 mg/kg to 5 mg/kg; 0.07 mg/kg to 2 mg/kg; 0.1 mg/kg to 0.9 mg/kg; 0.2 mg/kg to 0.7 mg/kg; and 0.3 mg/kg to 0.5 mg/kg.

In an embodiment, the subject matter described herein is directed to a method of delivering a cargo to a target within the body of a subject. The method comprises administering a cargo associated with PolyMet or LPH-PolyMet to a subject, wherein the cargo is delivered by the PolyMet or LPH-PolyMet to a target within the body of the subject. The cargo can be a therapeutic agent as described elsewhere herein. In this embodiment, the methods comprise administering PolyMet or LPH-PolyMet complexed or associated with a cargo to a subject, wherein the PolyMet or LPH-PolyMet provides the cargo to a target within the body of the subject.

Methods and Kits for Transfection

The PolyMet and LPH-PolyMet described herein can be used as a transfection agent for modifying the genetic material of a cell. Any exogenous genetic material can be complexed or associated with the PolyMet and LPH-PolyMet such that the genetic material can be delivered to the cell, thereby modifying the genetic material of the cell. Accordingly, the PolyMet and LPH-PolyMet described herein are useful for transfecting a cell.

In an embodiment, the subject matter described herein is directed to methods of modifying the genetic material of a cell, comprising: contacting the cell with a PolyMet or LPH-PolyMet complexed or associated with exogenous genetic material, wherein the genetic material of the cell is modified. The term "exogenous genetic material" refers to any genetic material that is delivered from outside the cell.

In this embodiment, the cell can be a eukaryotic cell, mammalian cell, plant cell or prokaryotic cell. Particular cells include a primary cell culture, a passaged cell culture or cell line, a human cell line, an animal cell line, and a fibroblast.

The genetic material can be a nucleic acid. The present invention provides compositions and methods for transfecting eukaryotic cells, particularly higher eukaryotic cells, with nucleic acids. Nucleic acids, both DNA and RNA, are introduced into cells such that they retain their biological function. Nucleic acids that can be transfected by the methods of this invention include DNA and RNA of any size from any source comprising natural bases or non-natural bases, and include those encoding and capable of expressing therapeutic or otherwise useful proteins in cells, those which inhibit undesired expression of nucleic acids in cells, those which inhibit undesired enzymatic activity or activate desired enzymes, those which catalyze reactions (ribozymes), and those which function in diagnostic assays (e.g., diagnostic nucleic acids). Therapeutic nucleic acids include those nucleic acids that encode or can express therapeutically useful proteins, peptides or polypeptides in cells, those which inhibit undesired expression of nucleic acids in cells, and those which inhibit undesired enzymatic activity or activate desired enzymes in cells.

The gene silencing effect of siRNA in LPH formulations was determined. H460/Luc cells are the cells that were stably transfected with the firefly luciferase gene. The siRNA formulated in the LPH-PEI-siLuc and LPH-PolyMet-siLuc formulations had a similar particle size (approximately 80 nm) and zeta potential (approximately +20 mV). As shown in FIG. 8, similar to Lipofectamine, LPH-PolyMet-siLuc reached 50% silenced gene expression with as low as 60 nM siRNA, while LPH-PEI-siLuc can only reached about 10% silence. Such efficient siRNA silencing with PolyMet nanoparticles in vitro, is highly desirable.

Figure 8A:
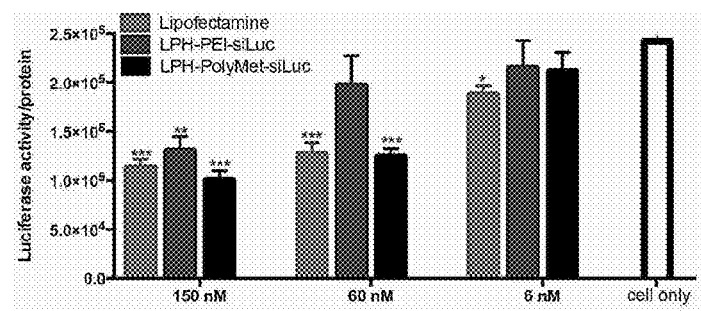
FIG. 8 depicts in vitro and in vivo gene silencing effect of different LPH nanoparticles. For the in vitro study, as shown in FIG. 8A, H460/Luc cells were incubated with different LPH formulations with different doses of siRNA at 37° C. for 4 hrs. At the end of incubation, cells were washed with PBS and cultured in siRNA free media for another 24 hrs. Luciferase activities of cells were analyzed and normalized by protein. *p<0.05, p<0.01, *p<0.001. Data are mean±S.D. (n=8 per group). For the in vivo study, LPH nanoparticles composed of PolyMet can systemically deliver anti-apoptotic BCL2 siRNA to the tumor site and inhibit tumor growth. H460 tumor-bearing mice were injected intravenously every other day.
FIG. 8B depicts tumor BCL2 protein levels after 2 injections were measured by western blot analysis.
FIG. 8C depicts tumor volumes were measured every day.
FIG. 8D depicts TUNEL staining in H460 tumor cells after treatment with siRNA in different formulations in vivo. The percentage denotes the average percentage of TUNEL positive cells (green). Five randomly selected microscopic fields were quantitatively analyzed on ImageJ. Data are mean±S.D. (n=5 per group). *P<0.05, **P<0.01 versus control.
Figure 8B:
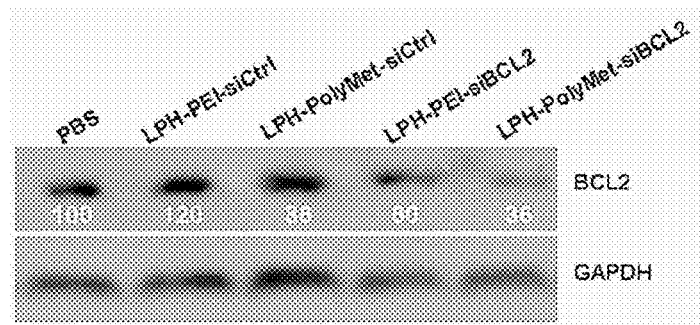
Figure 8C:
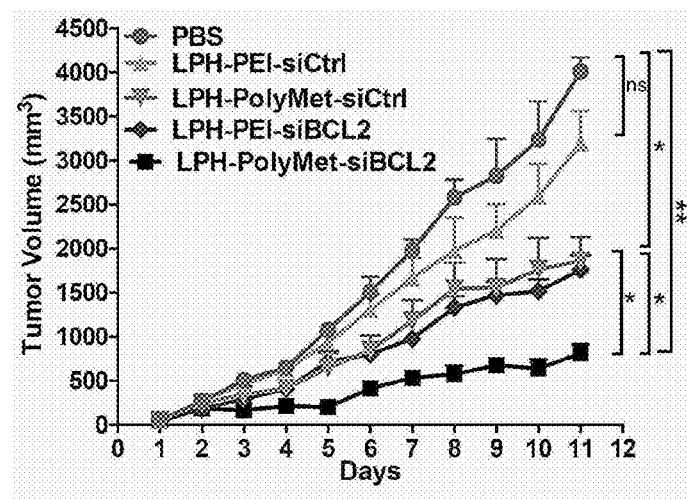
Figure 8D:
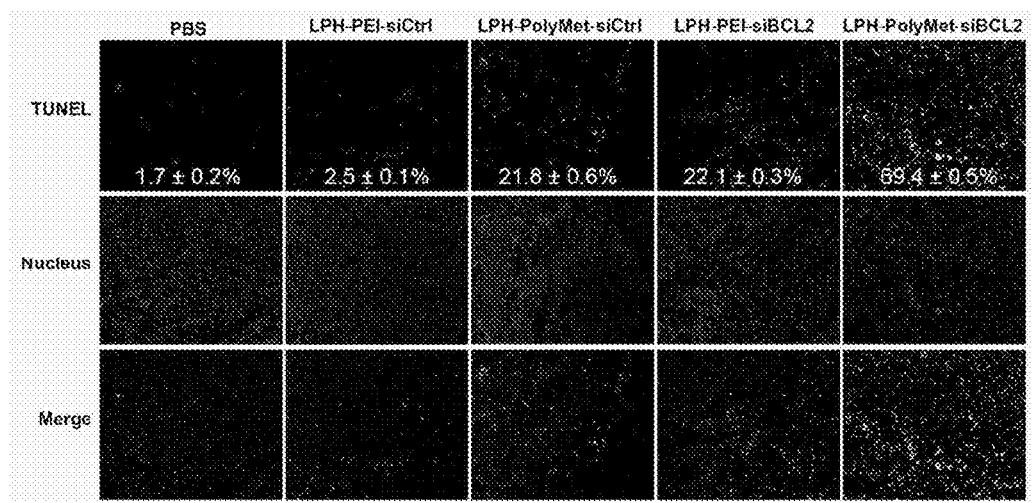
Figure 9A:
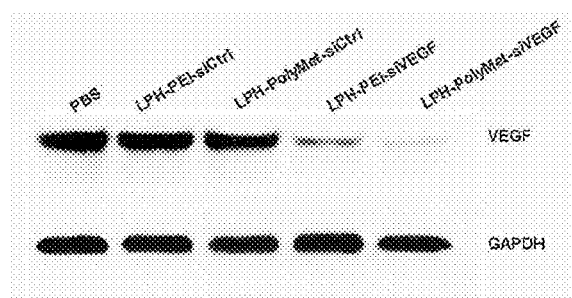
FIG. 9A depicts Tumor VEGF protein levels after 2 injections were measured by western blot analysis.
Figure 9B:
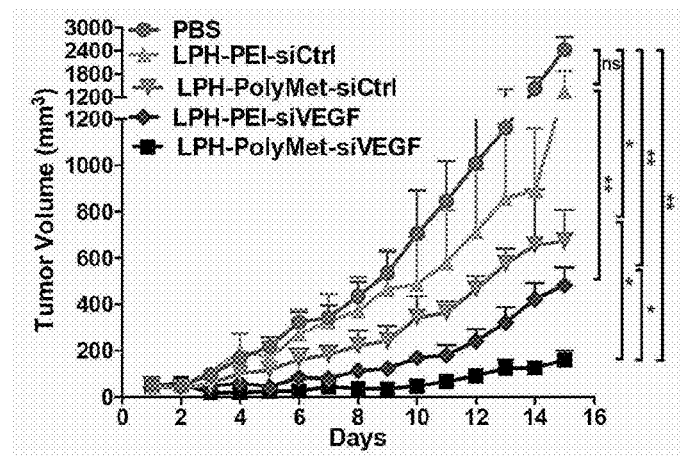
FIG. 9B depicts Tumor volumes were measured every day.
Figure 9C:
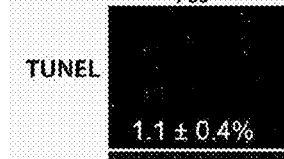
FIG. 9C depicts TUNEL staining in H460 tumor cells after treatment with siRNA in different formulations in vivo. The percentage denotes the average percentage of TUNEL positive cells (green). Five randomly selected microscopic fields were quantitatively analyzed on ImageJ. Data are mean±S.D. (n=5 per group). *P<0.05, **P<0.01 versus control.
Figure 9D:
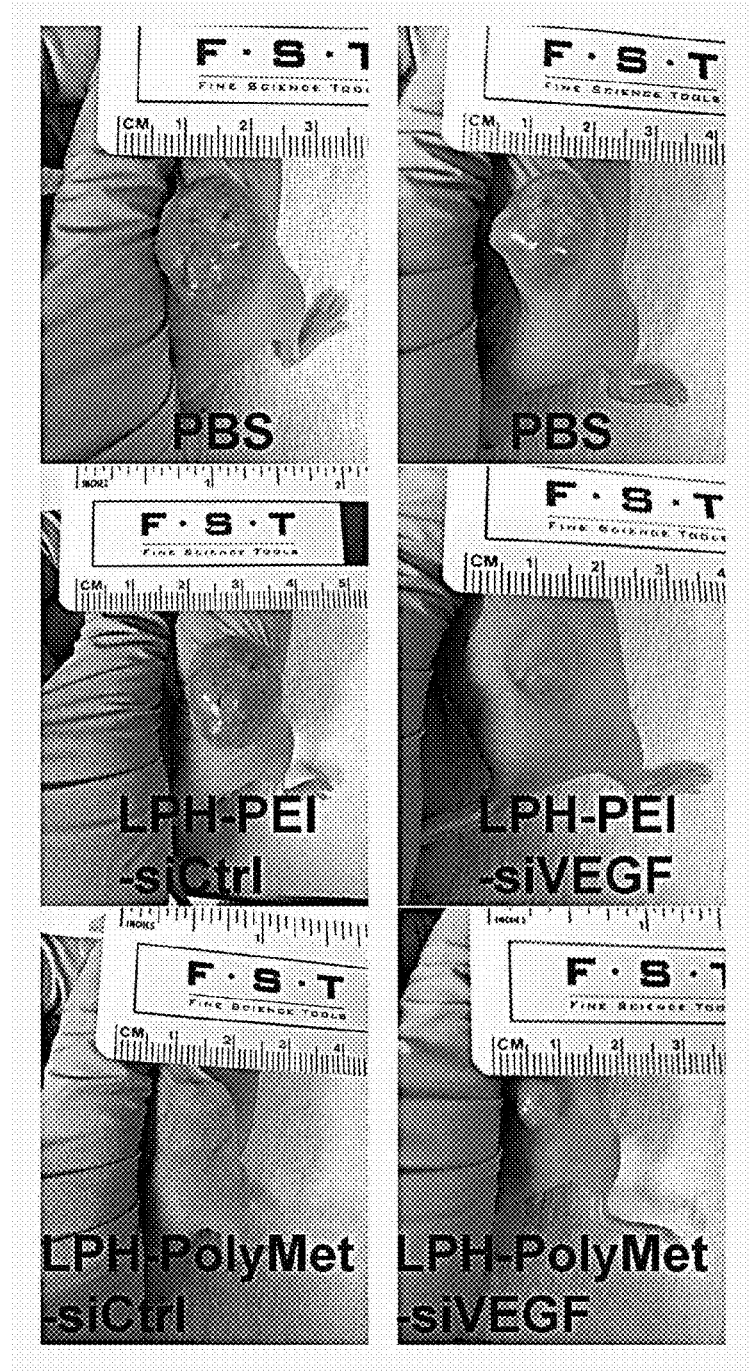
FIG. 9D depicts LPH-PolyMet-siVEGF silencing in mice.

The capability of PolyMet to delivery gene materials in vivo was determined. Although PolyMet can potentially deliver a number of siRNAs, BCL-2 siRNA was chosen as one of the example genes in the study. As an antiapoptotic protein, BCL-2 promotes cell survival, and inhibition of BCL-2 enhances the sensitivity of cancer cells to standard therapies (Tabuchi, Y. et al. Resistance to paclitaxel therapy is related with Bcl-2 expression through an estrogen receptor mediated pathway in breast cancer. *Int J Oncol* 34, 313-319 (2009)). The level of biological activity of BCL-2 after treatment was detected by western blot (FIG. 8B). LPH-PolyEMT-siBCL2 experienced an enhanced down-regulation of BCL-2 level in comparison with all other groups and provided robust and persistent suppression of tumor growth (FIG. 8C). TUNEL assay further confirmed the induction of apoptotic cells in tumors. The number of TUNEL-positive apoptotic cells after LPH-PolyMet-siBCL2 treatment was about 70%, which was significantly higher than all other groups (FIG. 8D). This indicates that elevated apoptosis occurs after down regulation of BCL2 expression.

Importantly, it was also observed that LPH-PolyMet-siCtrl exhibited significantly higher tumor inhibition compared with PBS or LPH-PEI-siCtrl, which confirmed findings observed in the LPH-PolyMet nanoparticles (FIG. 6).

The siRNA designed to suppress production of vascular endothelial growth factor (VEGF), which helps trigger angiogenesis, were also studied. Tumor growth was significantly depressed and the level of VEGF was dramatically lowered upon LPH-PolyMet-siVEGF treatment (FIG. 9).

Figure 10A:
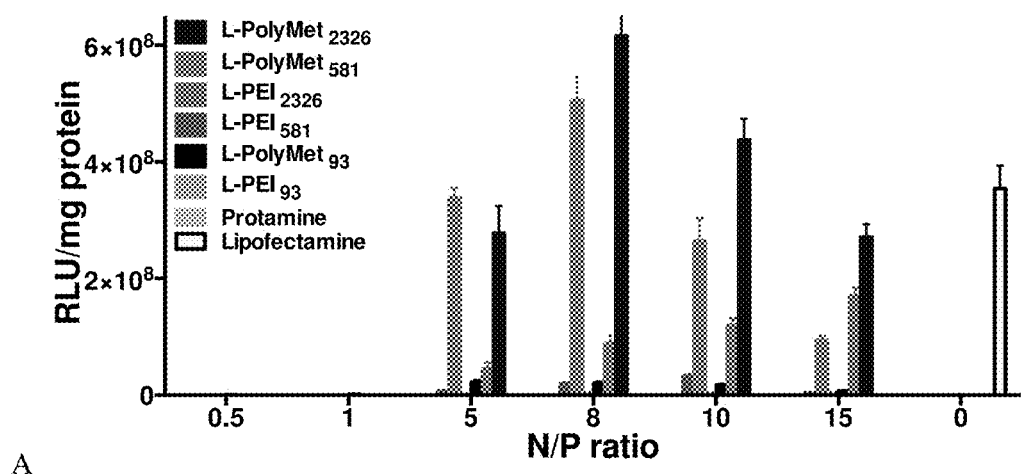
FIG. 10 depicts transfection efficiency of (A) L-PEI and L-PolyMet and (B) B-PEI and B-PolyMet at the indicated N/P ratios. Luciferase pDNA concentration was 0.5 µg/well in 96-well plate. Data are mean±S.D. (n=6 per group).
Figure 10B:
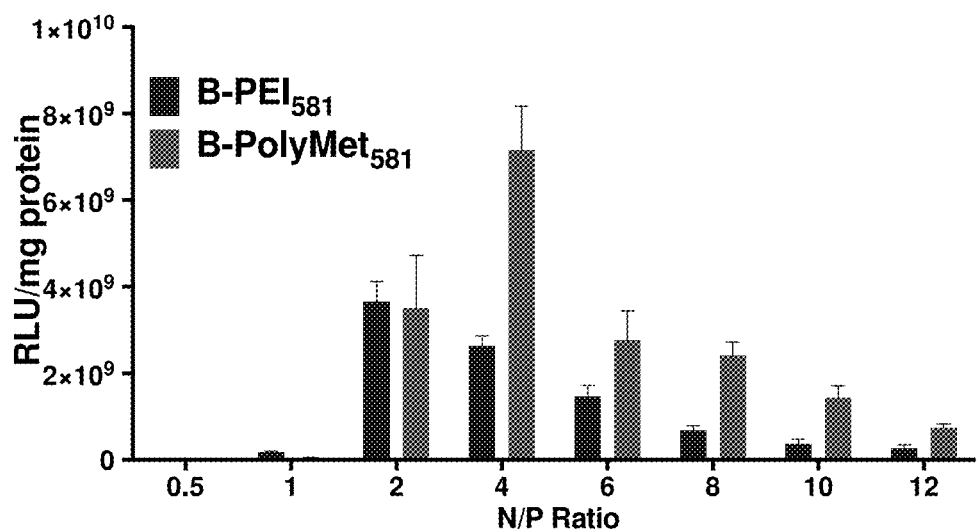
Figure 11:
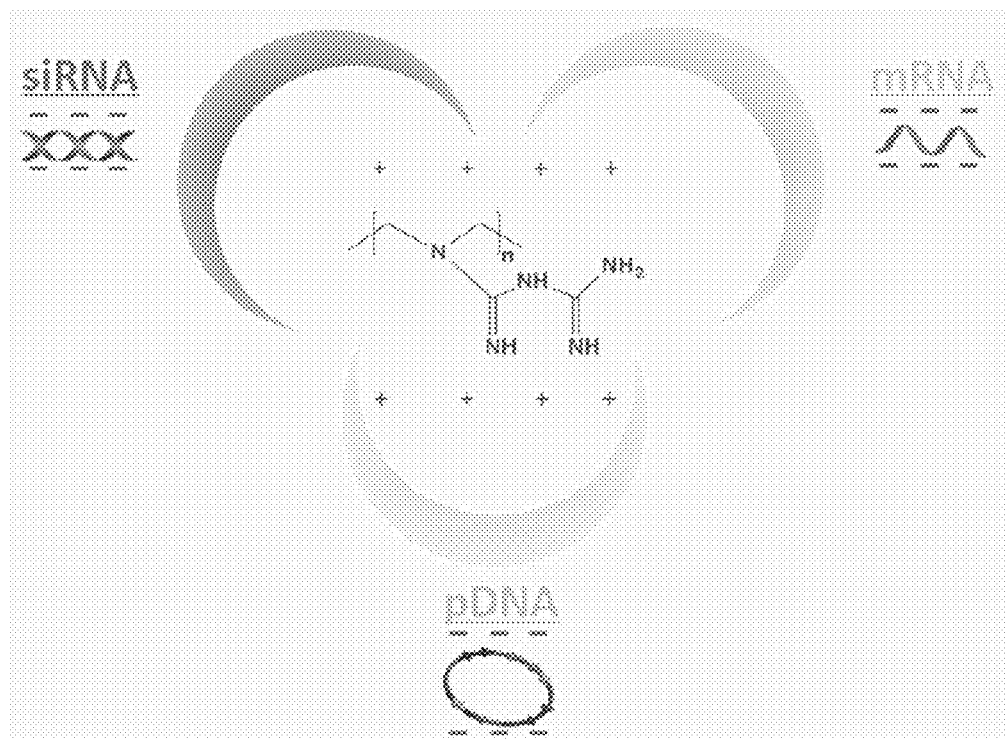
FIG. 11 is an illustration of a gene delivery property.
Figure 12:
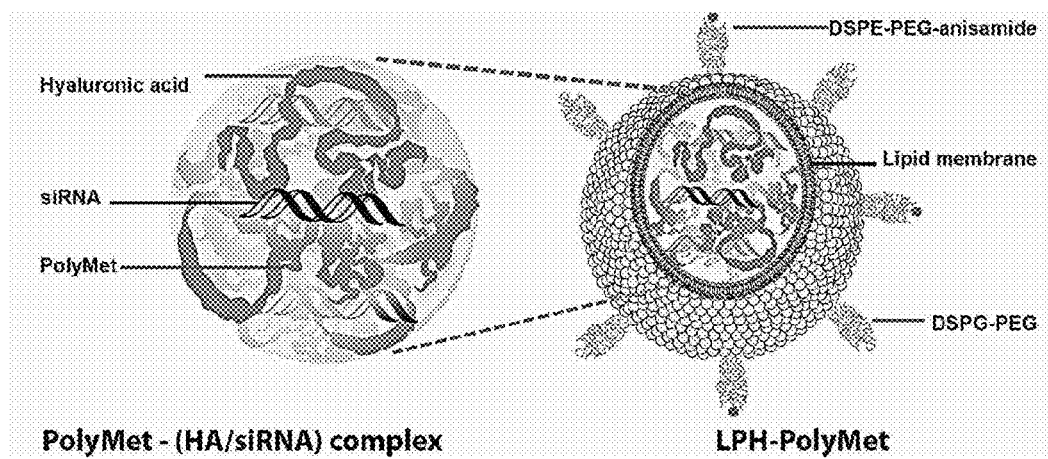
FIG. 12 is an illustration of siRNA delivery using LPH-PolyMet.
Figure 13:
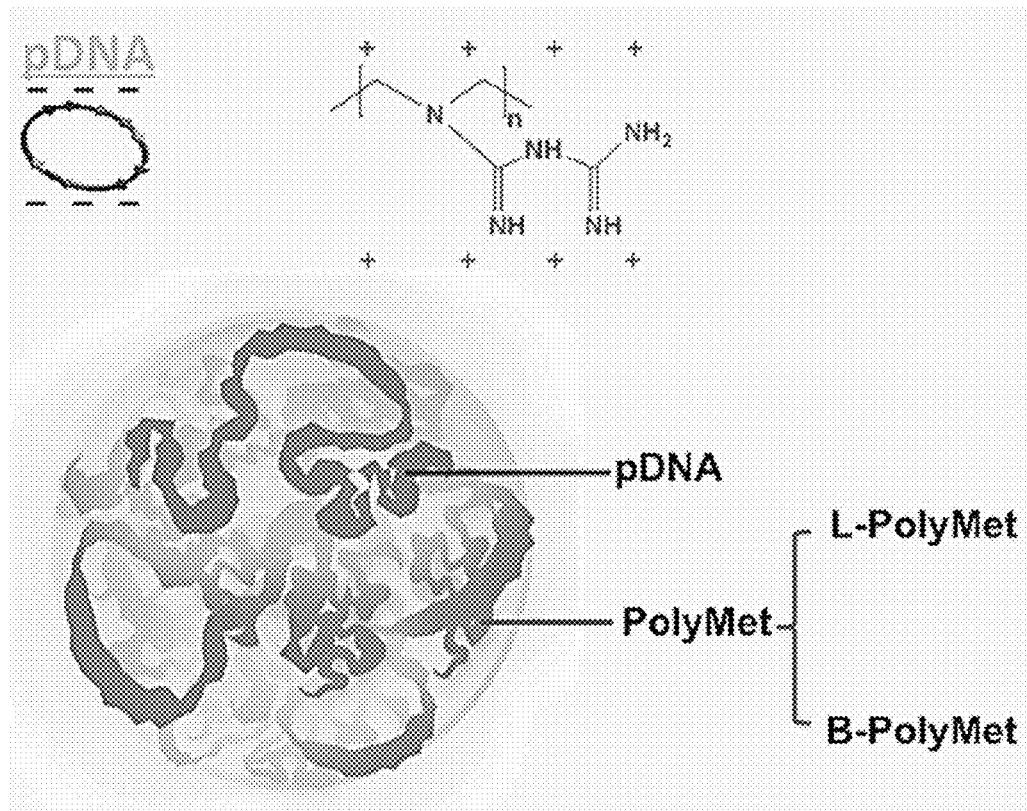
FIG. 13 is an illustration of pDNA delivery using LPH-PolyMet.
Figure 14:
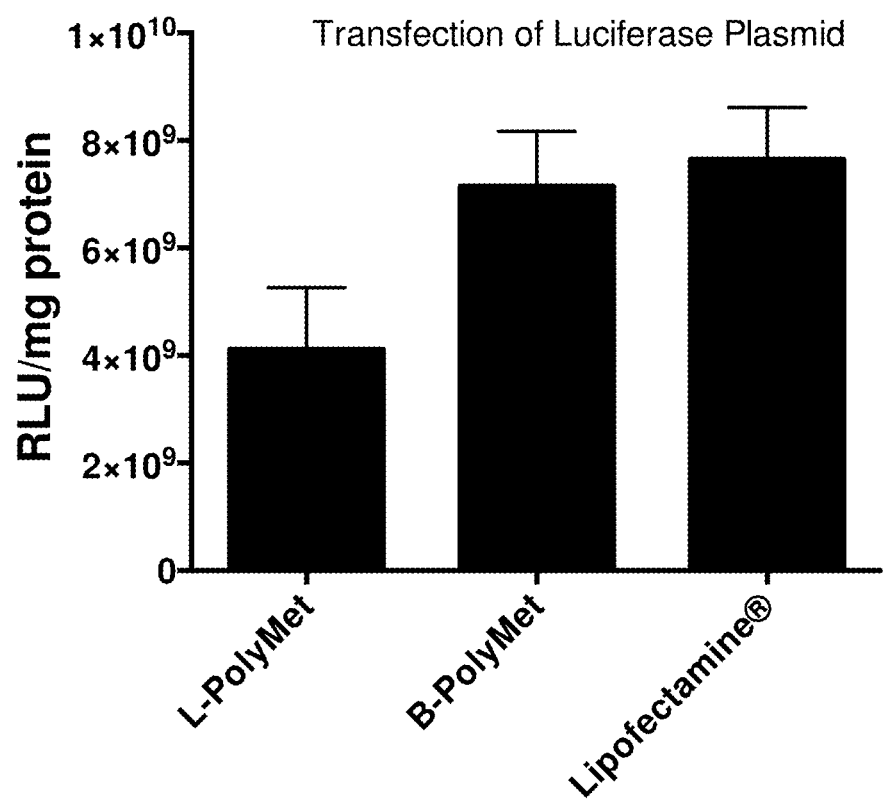
FIG. 14 depicts data showing Luciferase plasmid activity in H460 cells.
Figure 15:
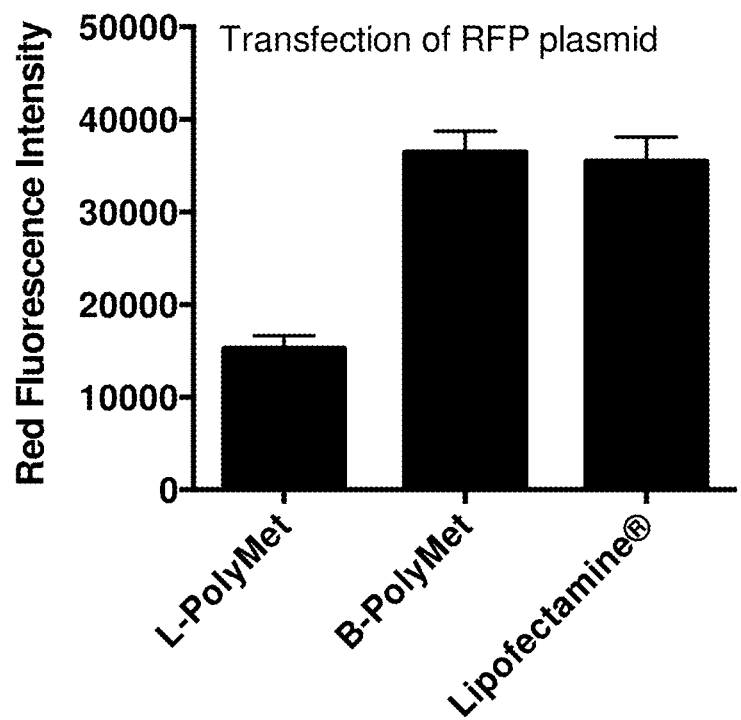
FIG. 15 depicts data showing RFP plasmid activity in H460 cells.
Figure 16A:
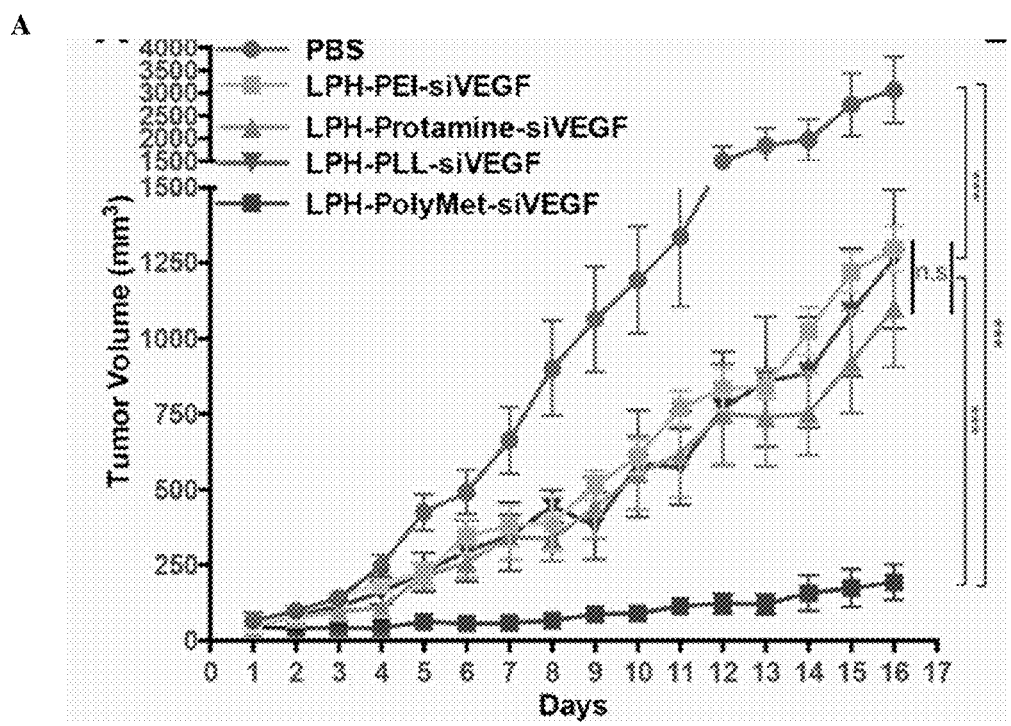
In FIG. 16A, H460 tumor-bearing mice were injected intravenously every other day and tumor volumes were measured every day.
Figure 16B:
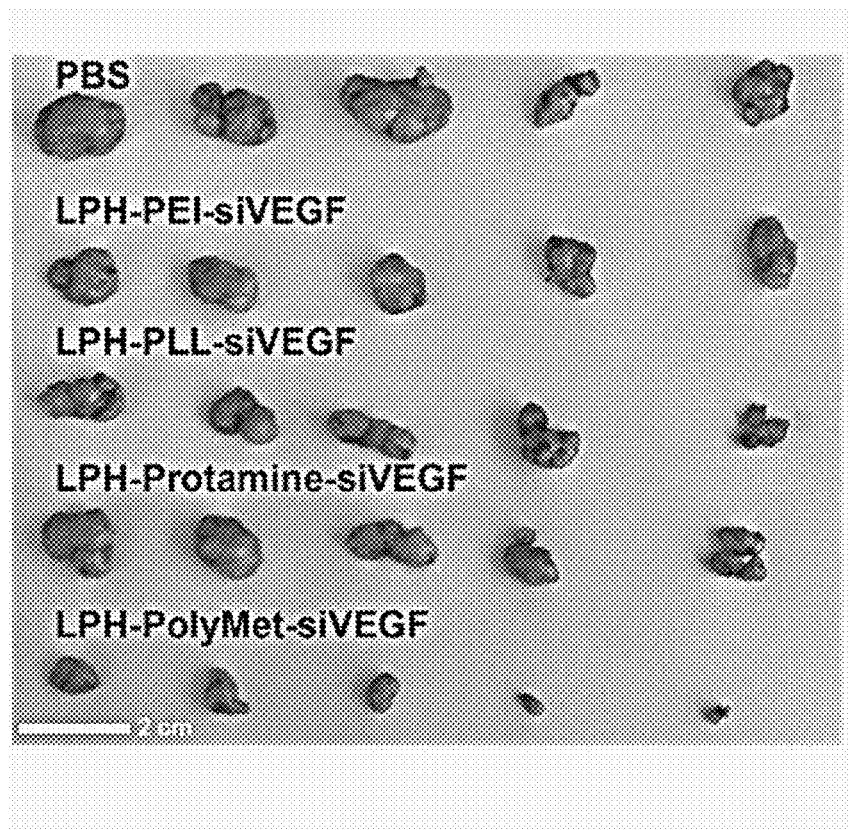
FIG. 16B shows H460 tumors in each treatment group at the end time point.
Figure 16C:
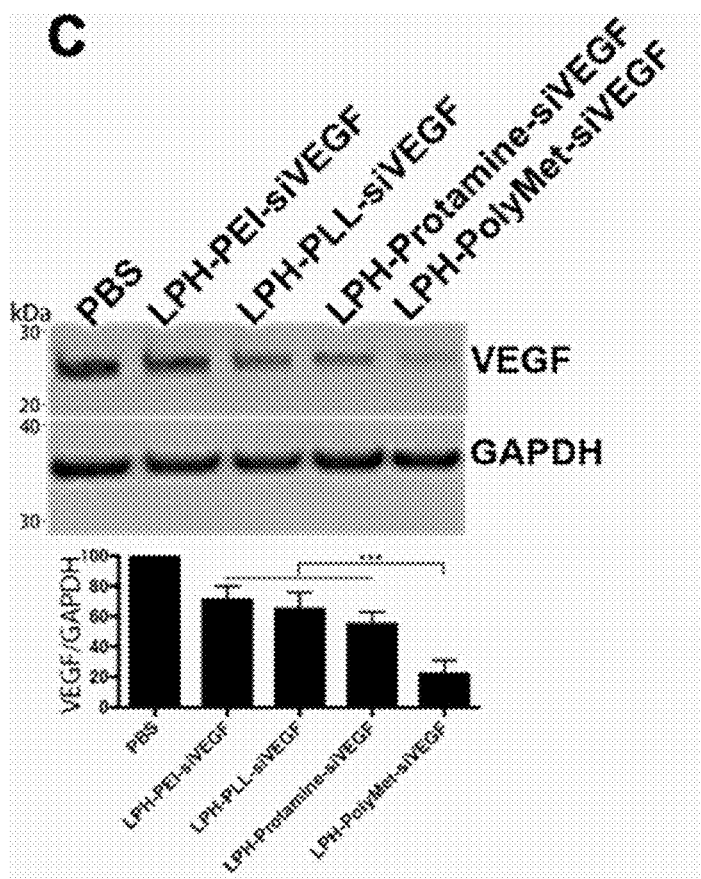
In FIG. 16C, H460 tumor VEGF protein levels after eight injections were measured by Western blot analysis. The bar chart in FIG. 16C represents quantitative analysis of normalized VEGF band intensity using Image J. Data are mean±SEM (n=5 per group) analyzed by two-way ANOVA with Tukey's correction. Data are combined from (A) or representative of (B and C) three independent experiments n.s.=not significant, *P<0.05, P<0.01, *P<0.005.
Figure 17:
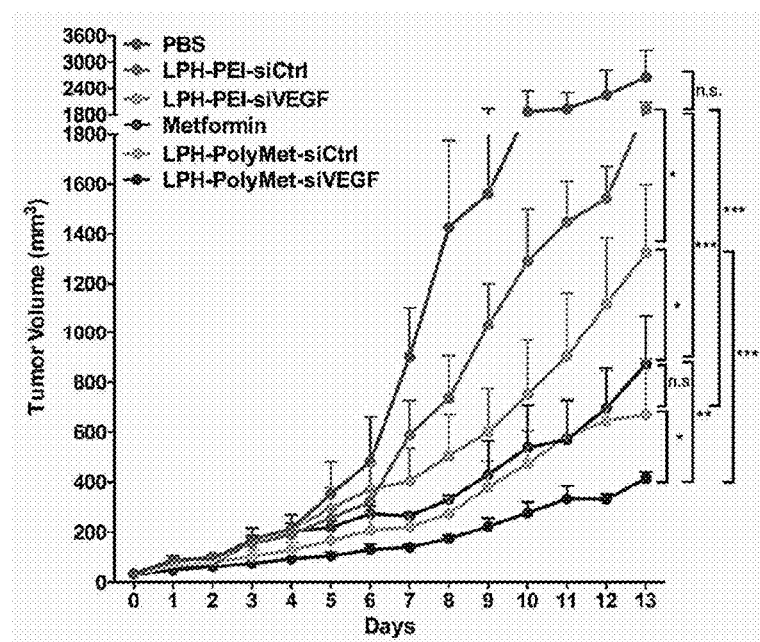
FIG. 17 depicts H460 tumor-bearing mice were injected intravenously with Metformin and LPH nanoparticles composed of PolyMet or PEI every other day. Tumor volumes were measured every day. Data are mean±SEM analyzed by two-way ANOVA with Tukey's correction; Data is combined from three independent experiments; 5 mice per group per experiment, n.s.=not significant, *P<0.05, P<0.01, *P<0.005.
Figure 18:
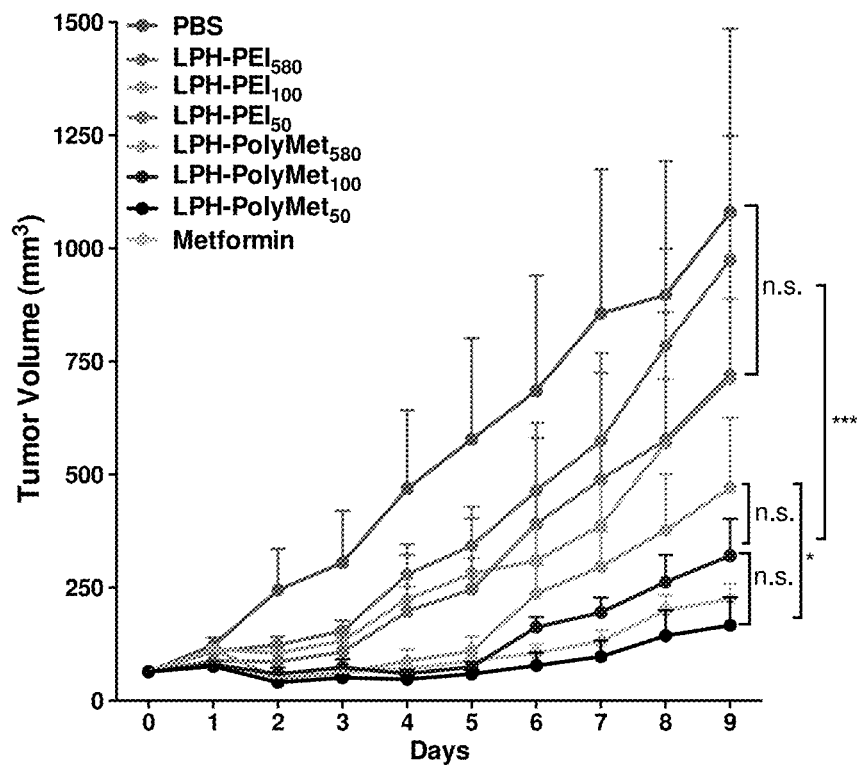
FIG. 18 depicts effects of different molecular weight of PEI and PolyMet LPH nanoparticles on the tumor growth. H460 tumor-bearing mice were injected intravenously every other day and tumor volumes were measured every day. 5 mice per group per experiment, n.s.=not significant, *P<0.05, P<0.01, *P<0.005.
Figure 19:
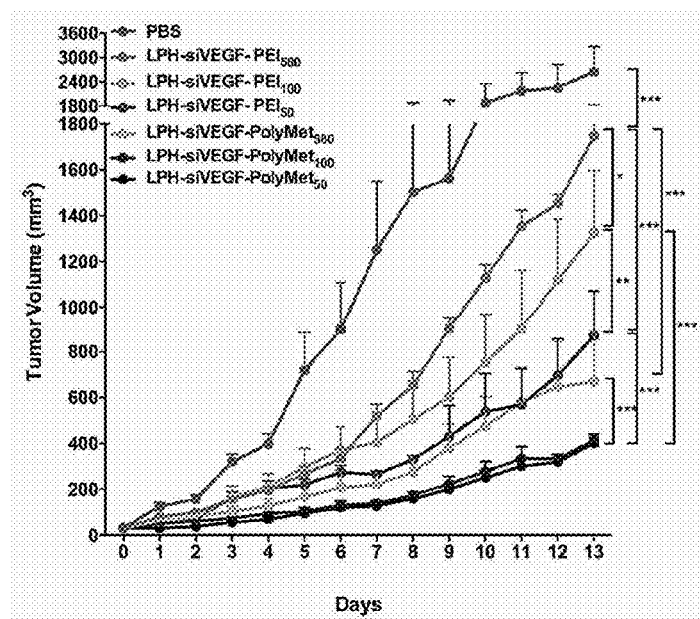
FIG. 19 depicts in vivo gene silencing effect of different molecular weight of PEI and PolyMet LPH in H460 xenografts. H460 tumor-bearing mice were injected intravenously every other day and tumor volumes were measured every day. 5 mice per group per experiment, n.s.=not significant, *P<0.05, P<0.01, *P<0.005.
Figure 20A:
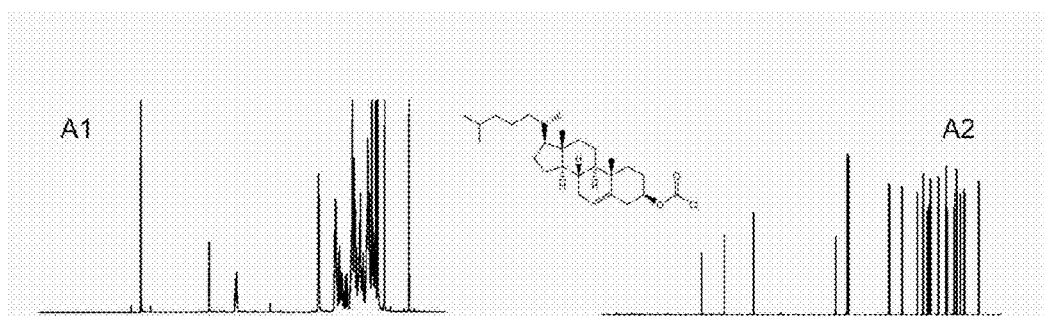
FIG. 20 depicts $^1$H NMR (1) and 13C NMR (2) spectra of the cholesteryl chloroformate (FIG. 20A), cholesteryl ethylenediamine (FIG. 20B) and cholesteryl biguanide (cholesteryl metformin) (FIG. 20C).
Figure 20B:
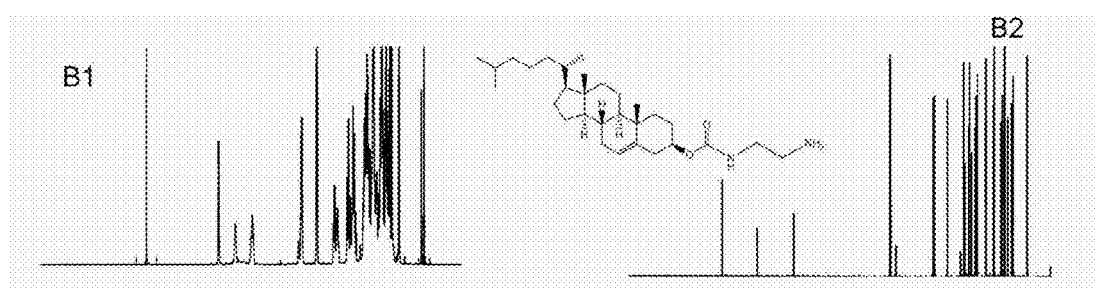
Figure 20C:
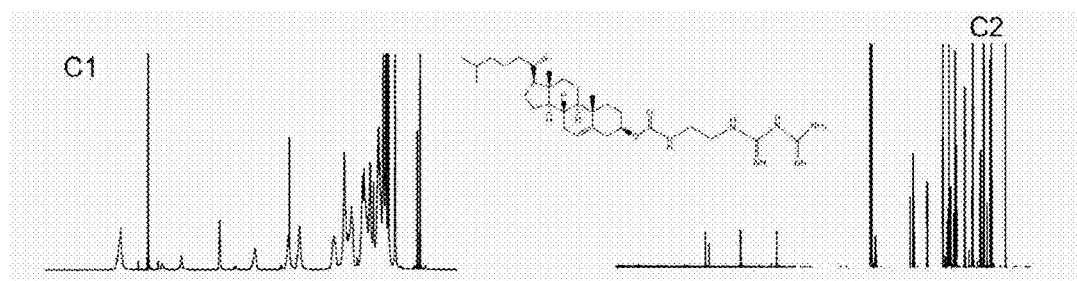
Figure 21A:
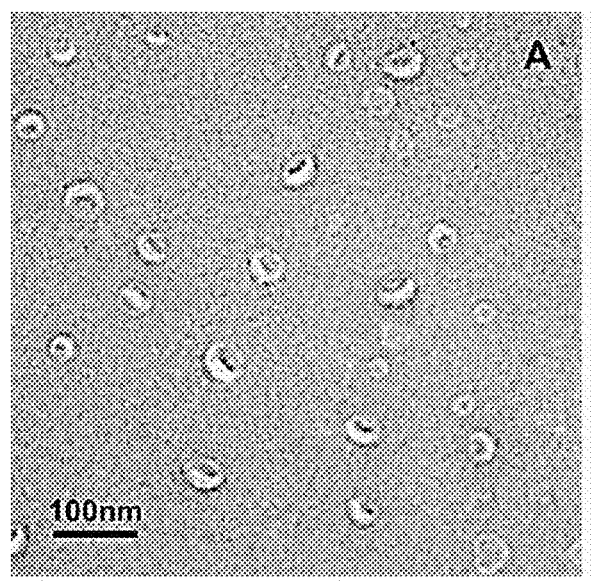
FIG. 21 depicts TEM morphology of liposomes from MET-Chol/DOPE (FIG. 21A) and EDA-Chol/DOPE (FIG. 21B).
Figure 21B:
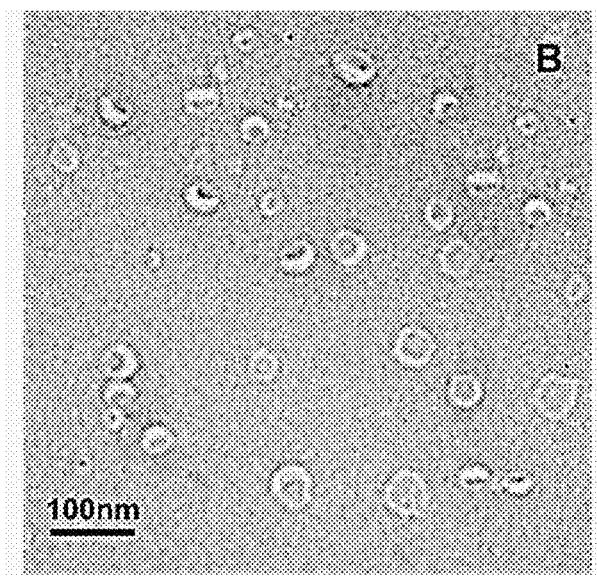
Figure 22:
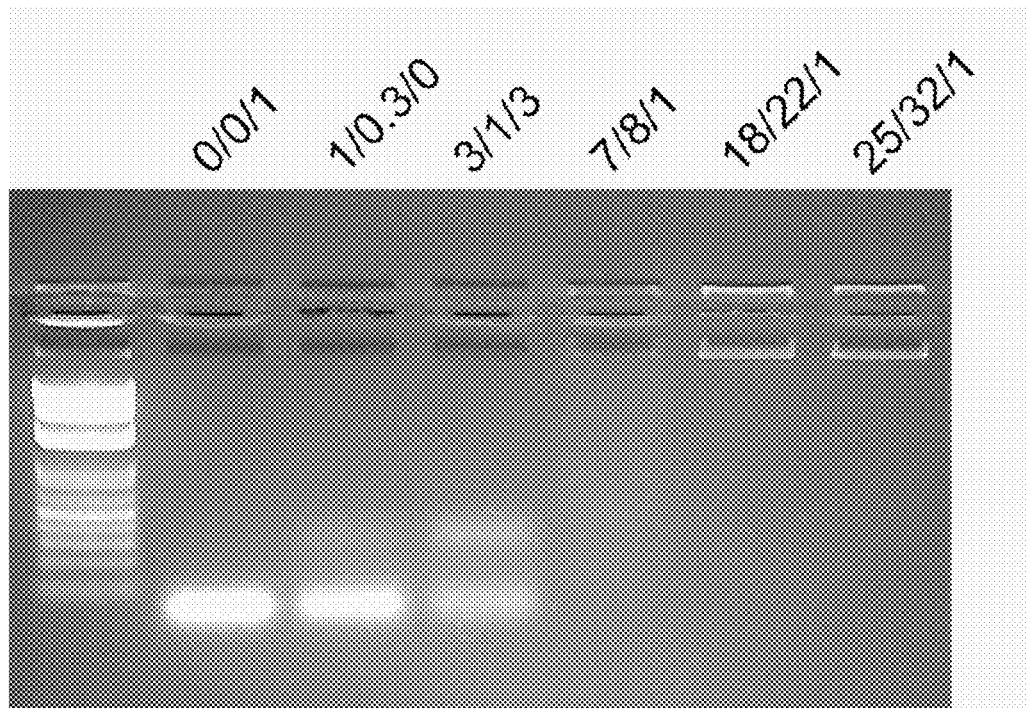
FIG. 22 depicts gel retardation assay of binding ability of PH to siRNA at different protamine/HA/siRNA N/P molar ratios.
Figure 23A:
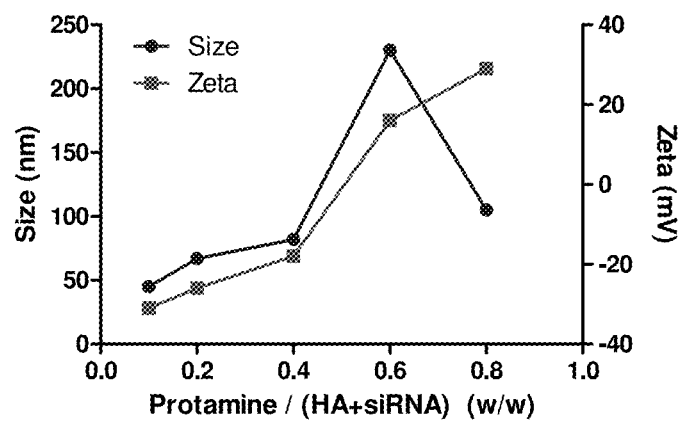
FIG. 23 depicts effects of protamine/(HA+siRNA) ratios on size and encapsulation efficiency of PH core.
Figure 23B:
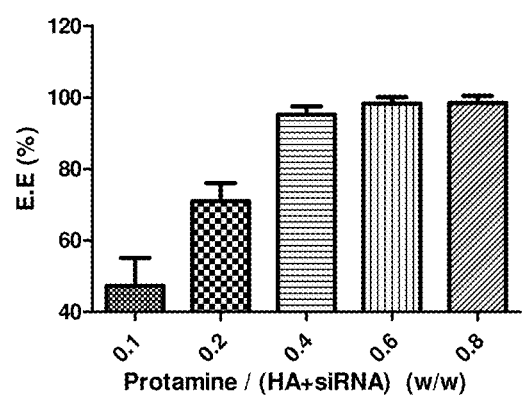
Figure 25A:
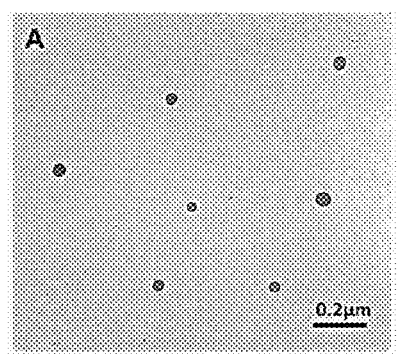
FIG. 25 depicts TEM morphology of (FIG. 25A) PH core and targeted LPH-NP from EDA-Chol/DOPE (FIG. 25B) and MET-Chol/DOPE (FIG. 25C). As used herein, PH refers to the protamine+hyaluronic acid complex. LPH-NP refers to lipid-polycation-hyaluronic acid nanoparticles. EDA-Chol refers to ethylenediamine cholesterol. MET-Chol refers to metformin modified cholesterol. DOPE refers to dioleoylphosphatidylethanolamine.
Figure 25B:
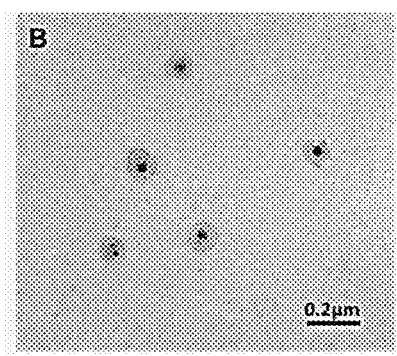
Figure 25C:
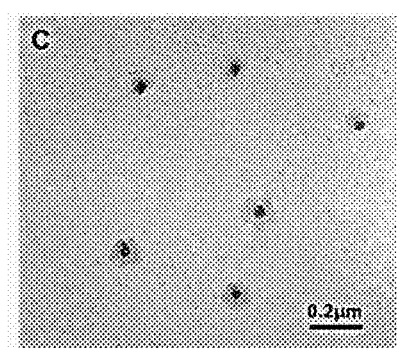
Figure 26A:
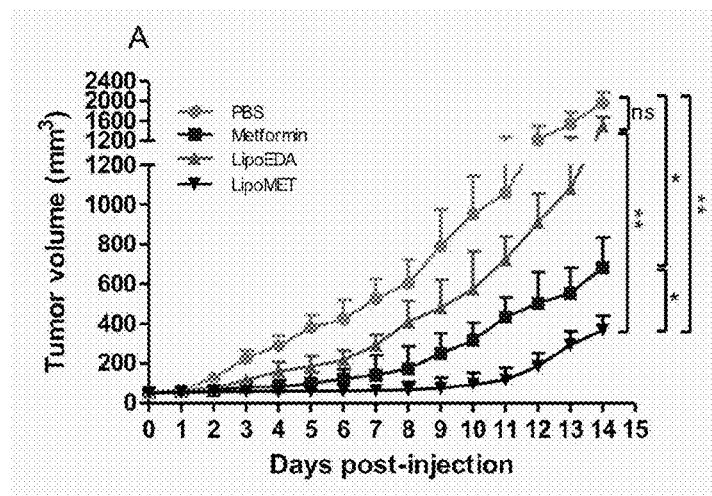
FIG. 26 depicts inhibition of tumor growth in a murine model with H460 xenografts after treatment with various formulations in FIG. 26A. Shown in FIG. 26B, tumor weights were measured on day after final injection and compared with body weights to determine percentage of tumor burden.
Figure 26B:
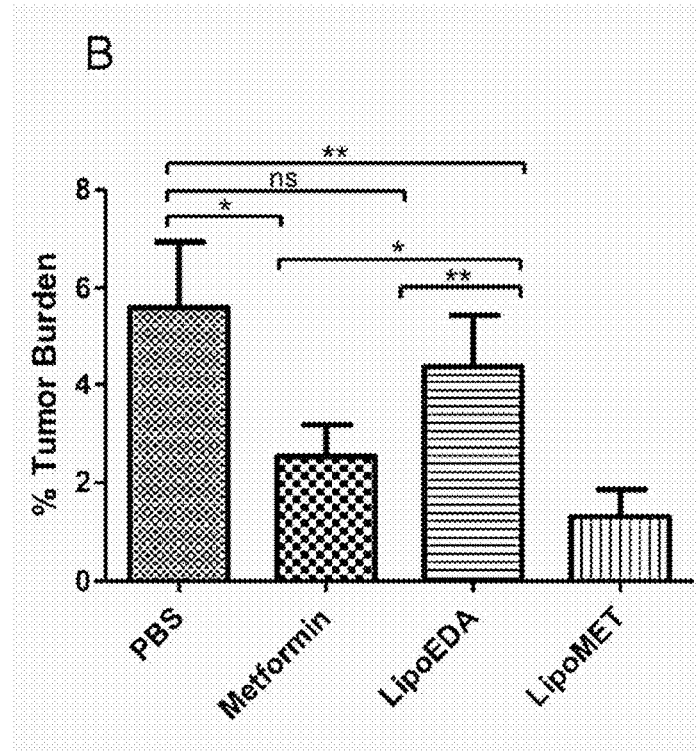
Figure 27A:
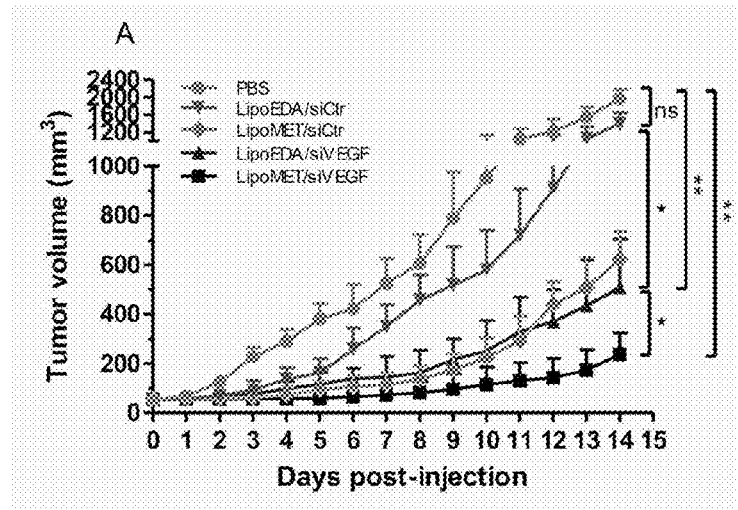
FIG. 27 depicts inhibition of tumor growth in a murine model with H460 xenografts after treatment with various siRNA formulations in FIG. 27A. Shown in FIG. 27B, tumor weights were measured on day after final injection and compared with body weights to determine percentage of tumor burden.
Figure 27B:
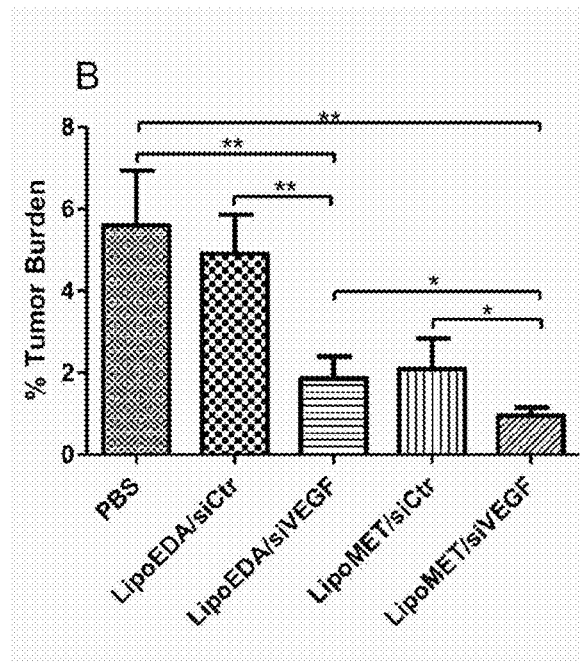
Figure 28A:
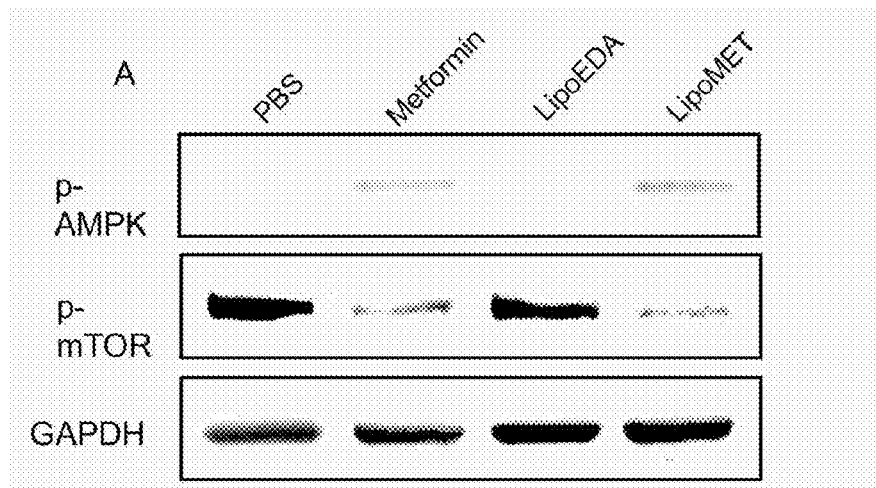
FIG. 28 depicts the expression of p-AMPK, p-mTOR protein (FIG. 28A) and VEGF protein (FIG. 28B) in tumors analyzed 24 h after the final injection.
Figure 28B:
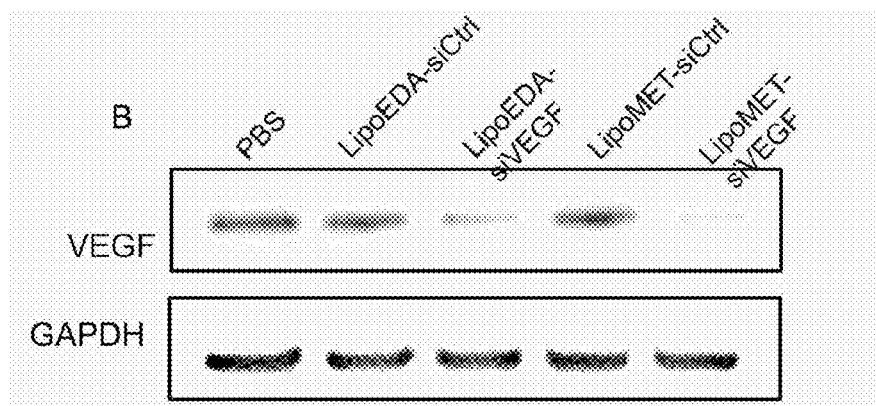
Figure 29:
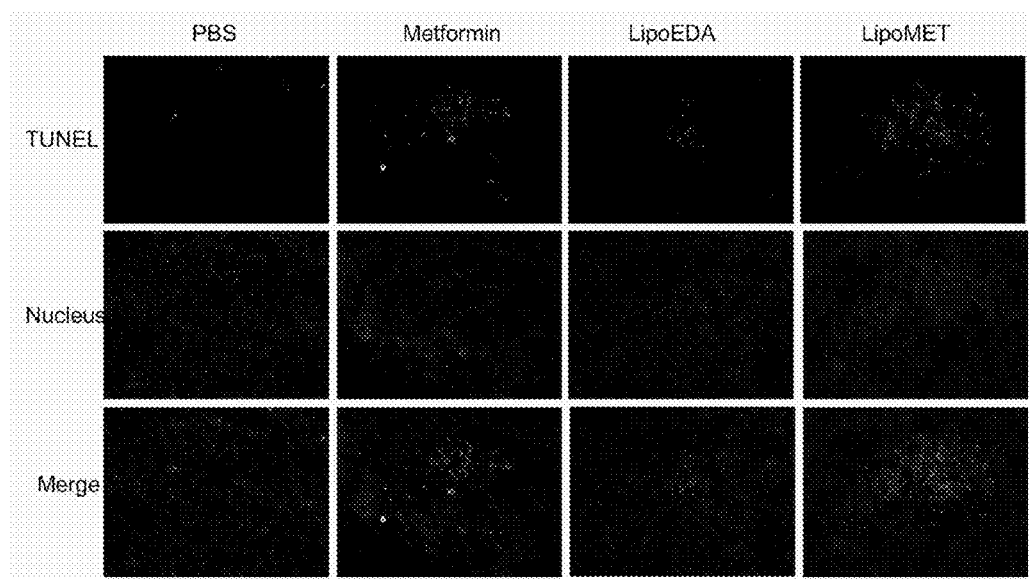
FIG. 29 depicts TUNEL assay of apoptosis induced by various formulations.
Figure 30:
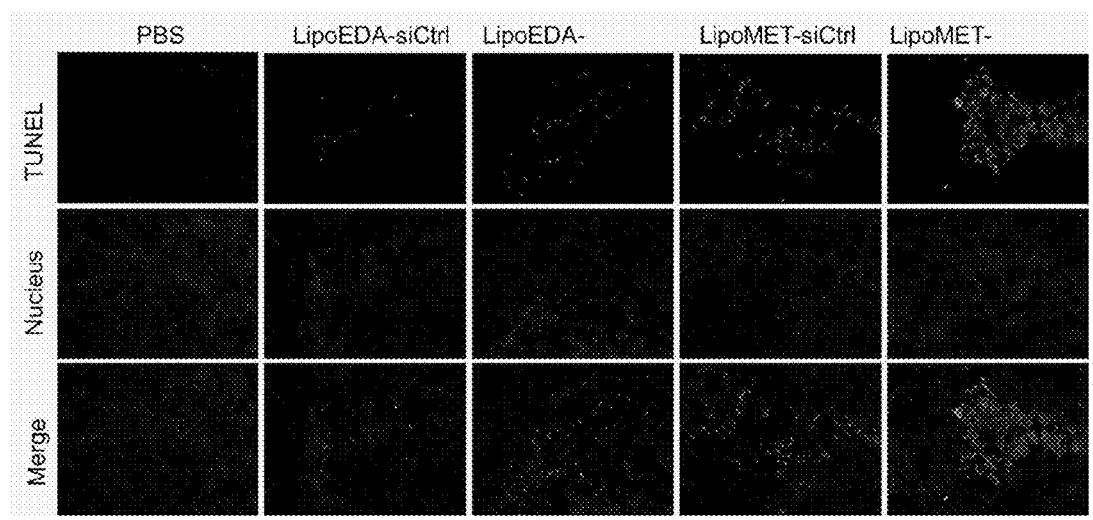
FIG. 30 depicts TUNEL assay of apoptosis induced by various siRNA formulations.
Figure 31:
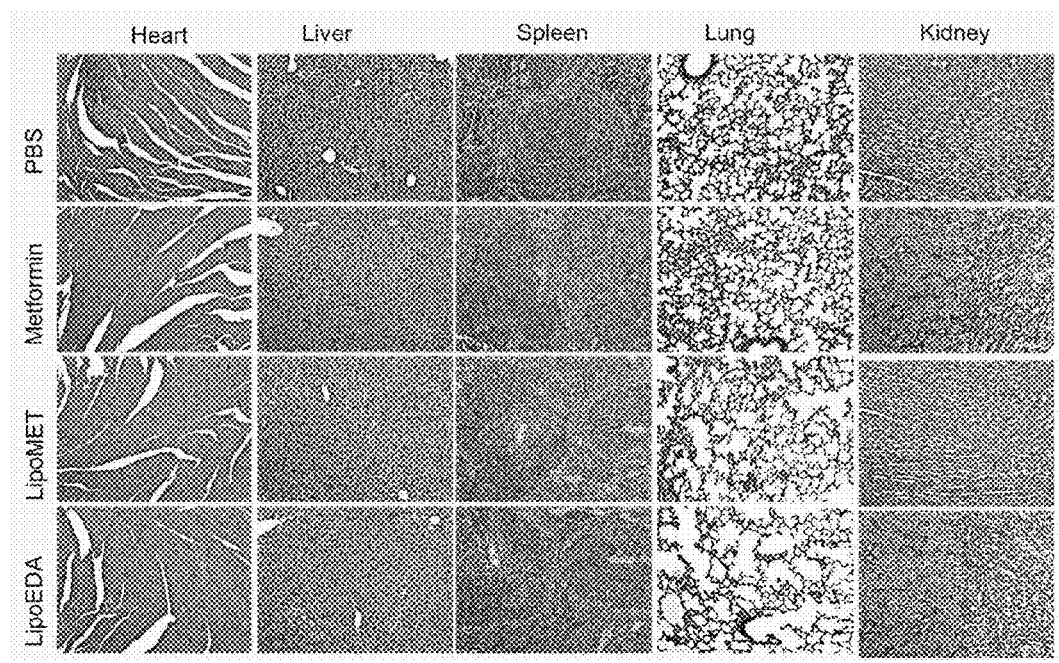
FIG. 31 depicts H&E staining of major organs after treatment of various formulations.
Figure 32:
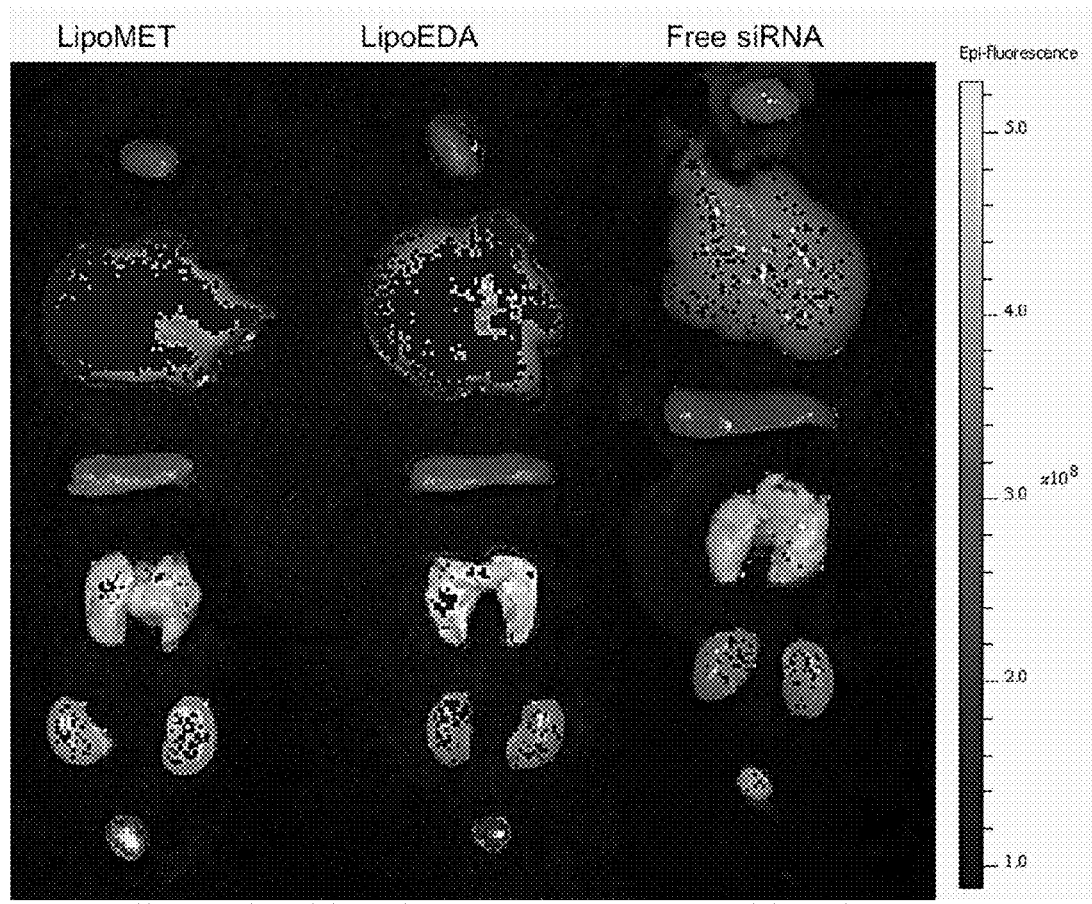
FIG. 32 depicts biodistributions of various formulations containing Cy-3 labeled siRNA in the mice.
Figure 33:
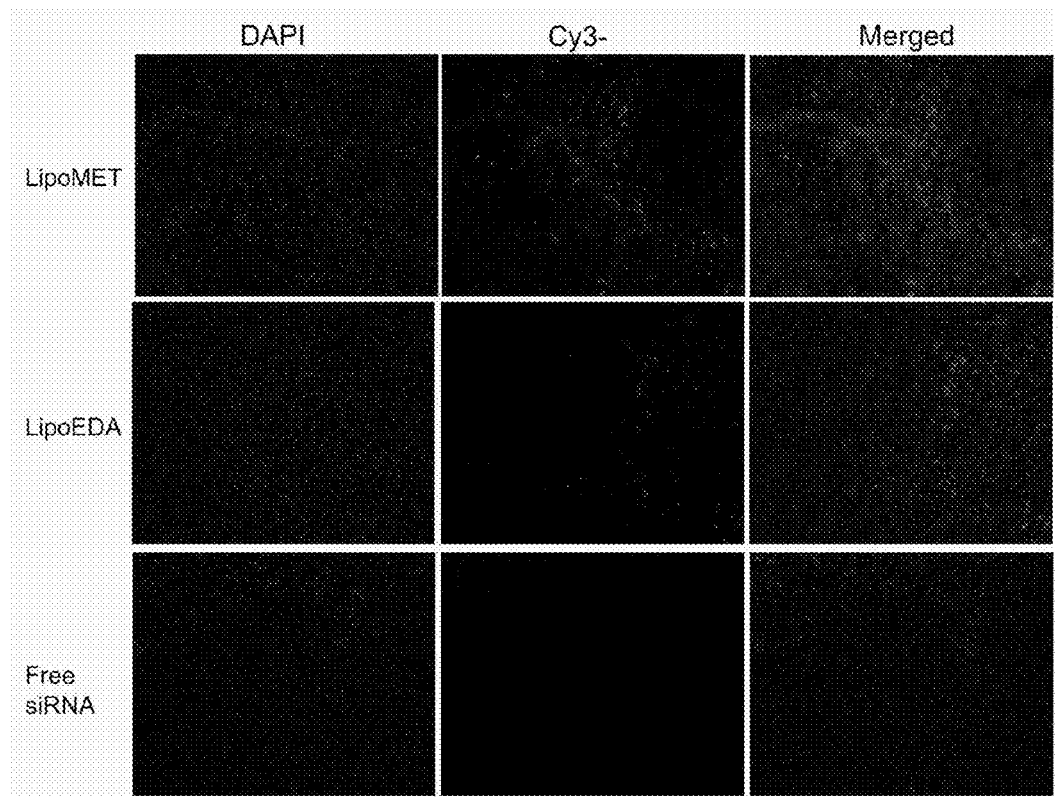
FIG. 33 depicts distributions of various formulations containing Cy-3 labeled siRNA in the tumor of H460 xenograft model.
Figure 34:
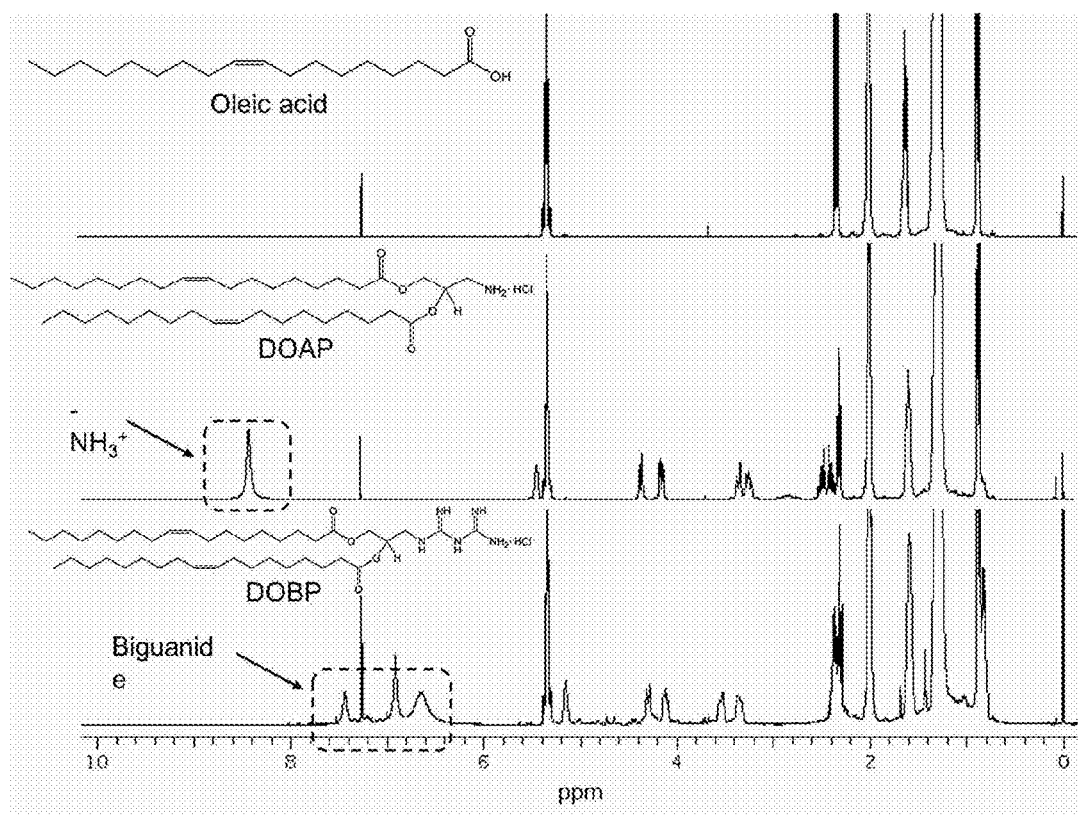
FIG. 34 depicts NMR spectra for DOBP, for which the synthesis was described in Scheme 3.
Figure 36:
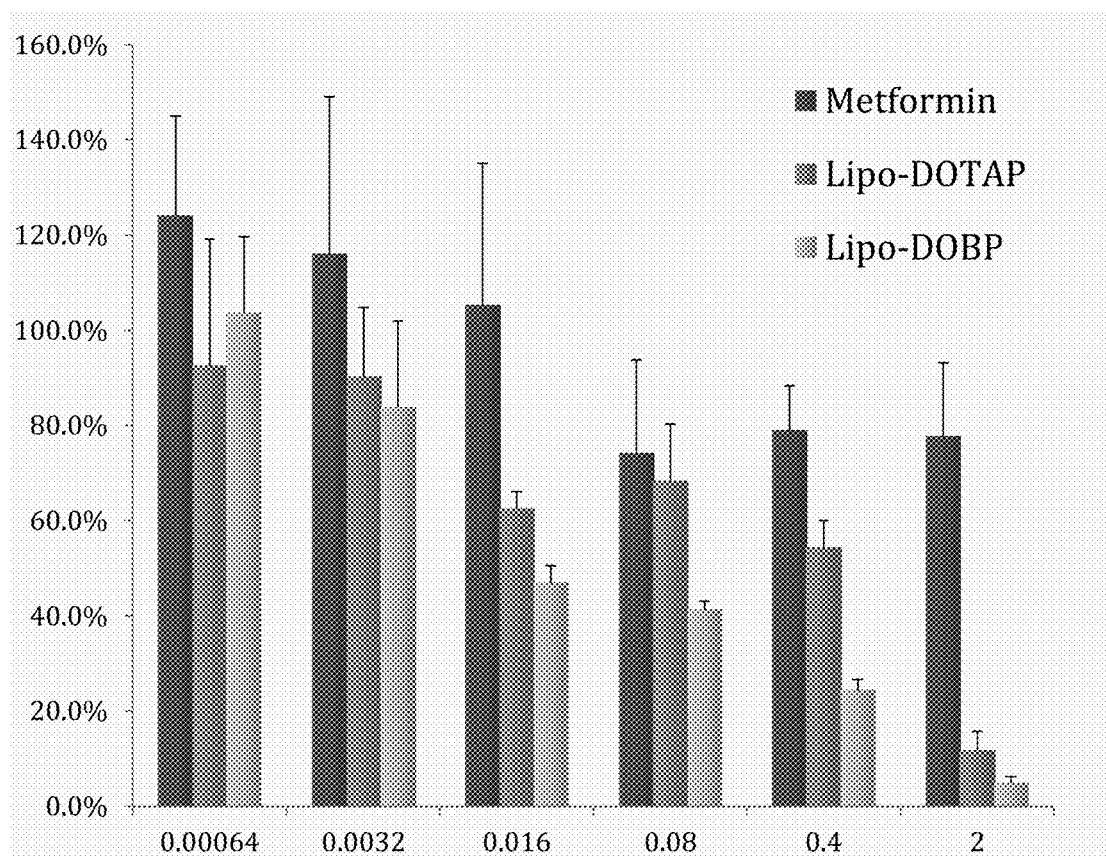
FIG. 36 depicts in vitro antitumor activity of blank liposomes (MTT). Blank liposomes refer to LPH-DOTAP and LPH-DOBP without loading DNA.
Figure 37:
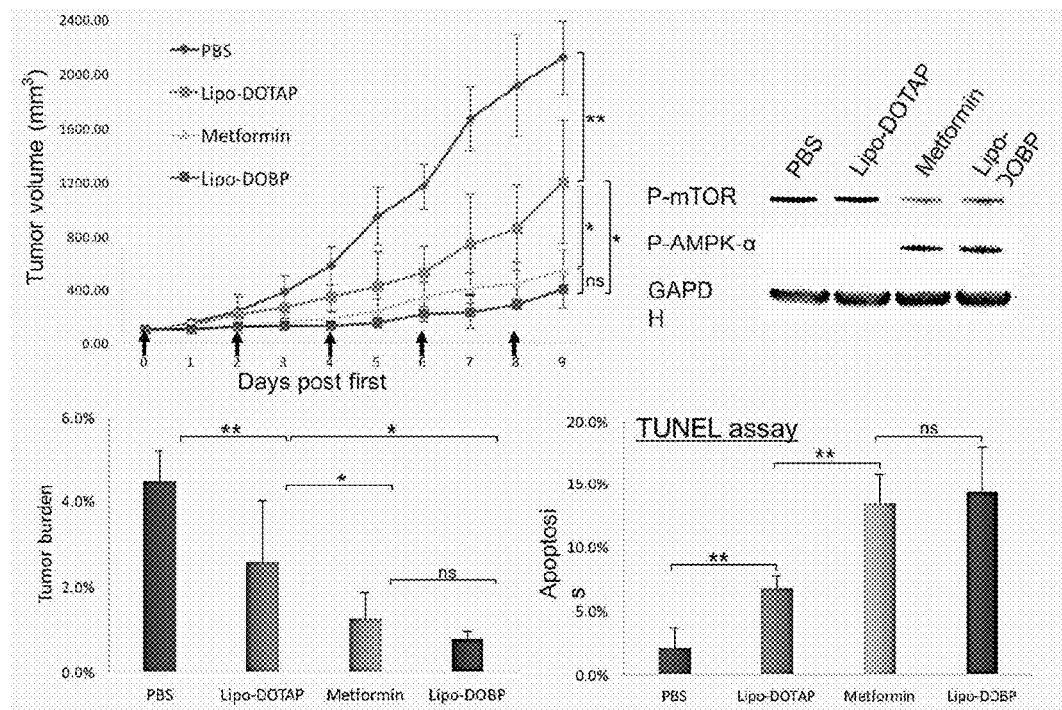
FIG. 37 depicts in vivo antitumor activity of blank liposomes (5 mg/kg of metformin).
Figure 38:
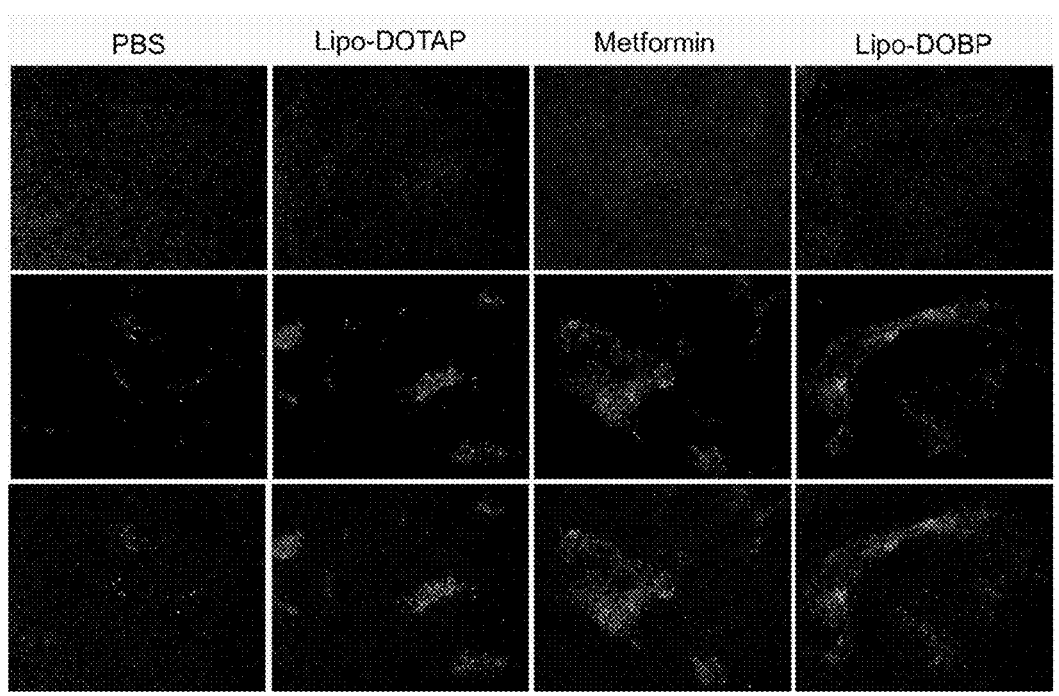
FIG. 38 depicts apoptosis (TUNEL assay) of different LPH nanoparticles.
Figure 39:
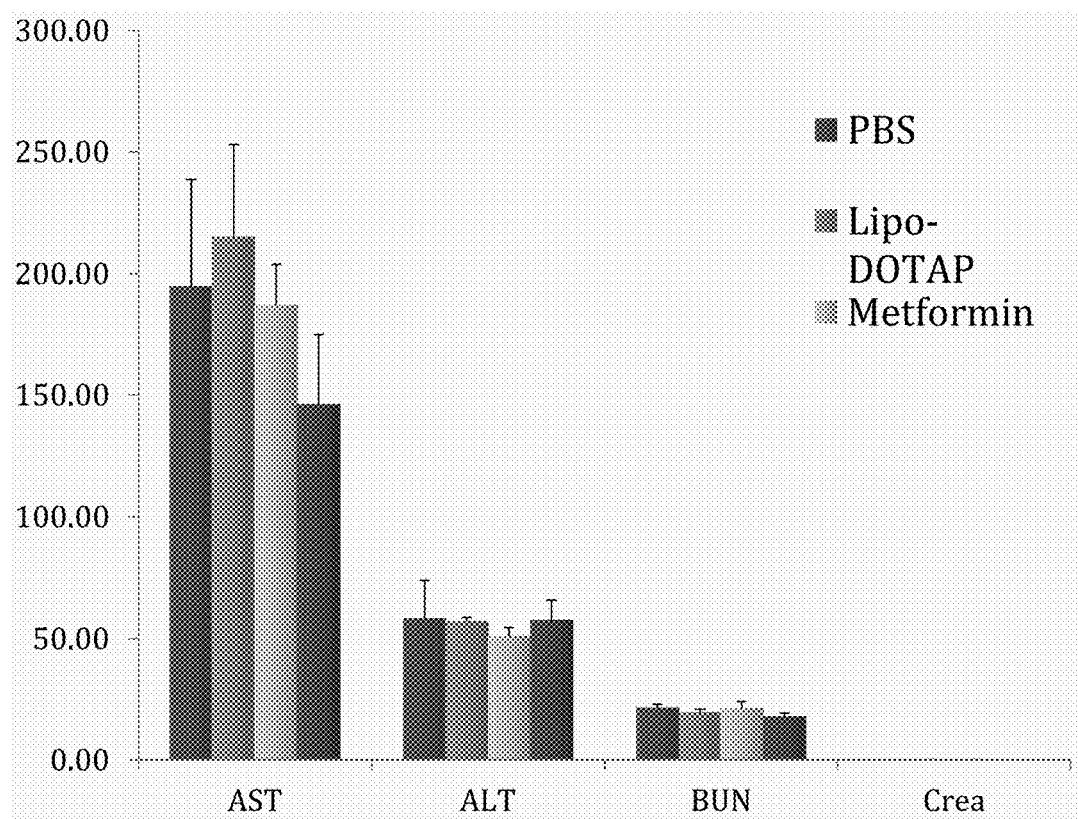
FIG. 39 depicts blood biochemistry test of serum of different LPH nanoparticles.
Figure 40:
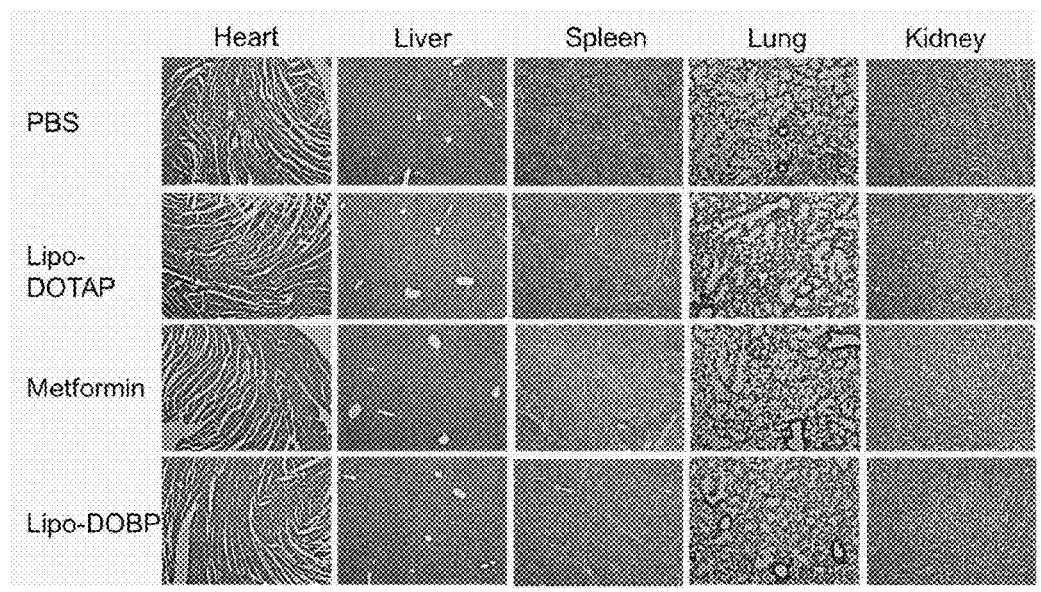
FIG. 40 depicts H&E stained organ slices after treatment of different LPH nanoparticles.

The ability of different PolyMet for pDNA transfection is assayed using a luciferase plasmid, and FIG. 10 shows the transfection efficiency and the cytotoxicity of polyplexes of different N/P ratios. In the N/P range from 0.5 to 15, the relative luminescence units (RLU) values of PolyMets showed a typical bell-shaped profile with the optimum N/P ratio of 8. At this ratio, PolyMetlook/pDNA complex had the highest transfection ability compared to all other agents, even 1.5 fold higher than the conventional transfection agent, Lipofectamine. Protamine is used as the drug carrier for siRNA and pDNA in our previous study; however, as shown in FIG. 10, protamine did not help the transfection efficacy.

Transfection agents and transfection-enhancing agents can be provided in a variety of pharmaceutical compositions and dosage forms for therapeutic applications as described elsewhere herein. In general the pharmaceutical compositions should contain sufficient transfection agent and any enhancing agents to provide for introduction of a sufficiently high enough level of nucleic acid into the target cell or target tissue such that the nucleic acid has the desired therapeutic effect therein. The level of nucleic acid in the target cell or tissue that will be therapeutically effective will depend on the efficiency of inhibition or other biological function and on the number of sites the nucleic acid must affect.

The dosage of transfection agent contacted with a cell in vitro or administered to a subject in vivo will depend on a number of other factors including the method and site of administration, patient age, weight and condition. Those of ordinary skill in the art can readily adjust dosages for a given type of administration, a given patient and for a given therapeutic application.

Components of the transfection compositions can be provided in a reagent kit. In general, the kit comprises PolyMet or LPH-PolyMet as a transfection reagent. The genetic material may be supplied with the kit or the end-user can add the genetic material to the PolyMet or LPH-PolyMet. Kit components can include appropriate medium or solvents.

A novel cationic derivative of cholesterol, cholesterol-metformin has also been synthesized and used to prepare liposome for gene therapy (Scheme 2). The biguanine group can facilitate efficient nucleic acids transfection in vitro and in vivo, while displayed low toxicity to the treated cells and organs.

It is to be noted that the term "sterol" refers to a group of chemical entities that are a subgroup of steroids where the hydroxyl group is on the 3-position of the A-ring. They have a specific, four ringed skeleton which is varied in stereochemistry and substituents depending on the specific sterol. In general, sterols contain from about 27 to about 30 carbon atoms and sometimes one double bond. Examples of sterols include, but are not limited to cholesterol, campesterol, sitosterol, stigmasterol, ergosterol, nicasterol, lanosterol, oxysterol, desmosterol, gorgosterol, and dinosterol.

Synthetic Methods

In an embodiment, the subject matter described herein is directed to a method of preparing PolyMet comprising contacting PEI with dicyandiamide in the presence of an acid. The acid can be any mineral or organic acid. Particularly useful acids include HCl.

Figure 2A:
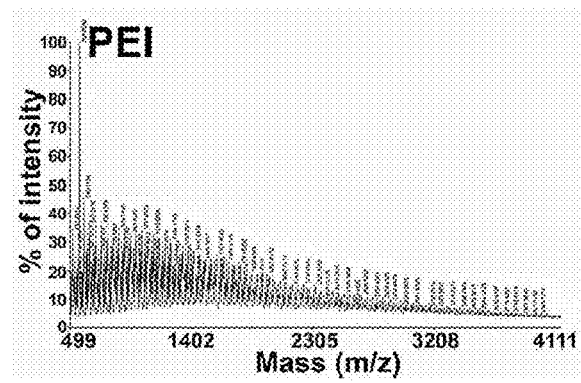
FIG. 2 depicts MALDI-TOF mass spectra of PEI and PolyMet. Dithranol (20 mg/ml in THF, NaTFA 1 mg/ml) was mixed with the samples, and a-Cyano-4-hydroxycinnamic acid was used for sample preparation. Intensity signals above 30% for PEI were extensively found in a range between 515.4 and 1244.1 (m/z). The intensity signals above 30% in the spectrum of PolyMet appeared from 670.5 to 3820.2 (m/z). In comparison to the position of the peaks in the PEI spectrum, peaks in the spectrum of PolyMet spectrum solution were shifted towards the higher mass range. Such a shift indicated that the molecular mass of PolyMet is higher than PEI, suggesting successful modification of PEI by dicyandiamide.
Figure 2B:
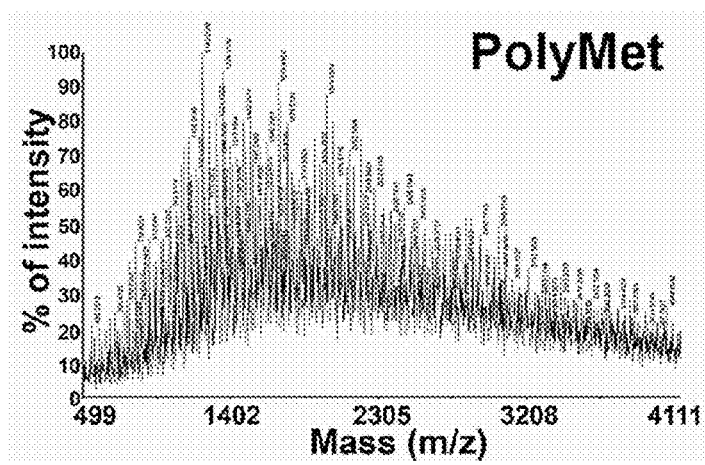

PolyMet is synthesized upon dicyandiamide protonation with an acid, such as HCl in the presence of straight or branched PEI. See Scheme 1. While not being bound to any theory, it is believed that intramolecular hydrogen bonds are interrupted, allowing nucleophilic attack of the lone pair located on the central nitrogen of PEI. PolyMet was characterized using MALDI-TOF, which indicated the modification of PEI by dicyandiamide (FIG. 2) was achieved.

Scheme 1. A synthetic route for preparing poly-metformin (PolyMet).

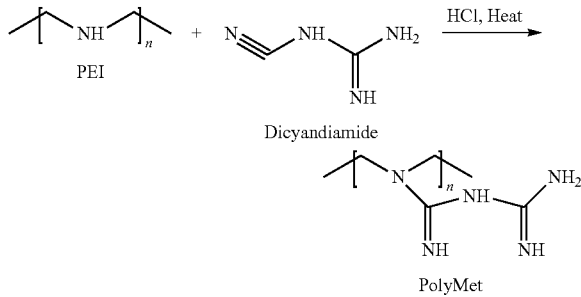

In this embodiment, the subject matter described herein is directed to a method of preparing a polymer of metformin, comprising:

a. contacting a linear or branched polyethylenimine with dicyandiamide in a solvent to prepare a first mixture;

b. contacting the first mixture with acid to prepare a second mixture; and c. heating the second mixture for a period of time, wherein a polymer of metformin is prepared.

Useful solvents include aqueous solvents, including water, methanol, ethanol, DMF, chloroform, THF, DMSO, etc.

Useful acids include organic and mineral acids, including HCl, sulfuric acid, nitric acid, boric acid.

Useful catalysts include metal ion catalysis, or electrostatic catalysis, including, $Fe^{3+}$, $Cu^{2+}$, $Zn^{2+}$, $Ca^{2+}$, $Al^{3+}$, $Si^{4+}$, $Ti^{4+}$, etc.

Useful periods of time include from minutes to hours to days, e.g., 5 minutes or more to 2-6 hours or even 1-6 days or a week.

The step of heating the second mixture comprises applying heat until the reaction reaches a desired temperature or range of temperatures, which may depend on the particular solvent chosen. Useful temperatures include from about 30° C. to about 200° C., from about 50° C. to about 150° C., from about 75° C. to about 125° C.

The order in which the steps are performed may not be particularly critical and in such cases, the order of steps can be modified.

The method may further comprise a purification step. Such purification can be based on size or other properties. Methods for purifying polymers are known in the art.

In another embodiment, the subject matter described herein is directed to methods of preparing LPH-PolyMet having a cargo. In this embodiment, the methods include loading the cargo into a LPH nanoparticle comprising PolyMet ("LPH-PolyMet").

Figures 3A, 3B:
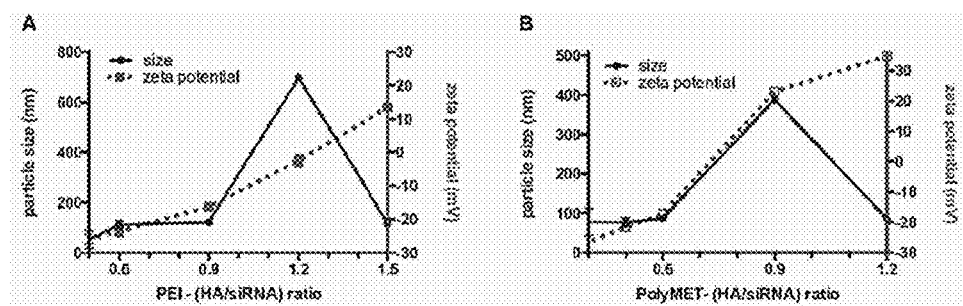
FIG. 3 depicts formulation optimization of the complexes. Effect of N/P ratio of PEI-HA (A) and PolyMet-HA (B) on particle size (blue) and zeta potential (red) of complexes.

To prepare the LPH-PolyMet nanoparticle, first the N/P ratios (the ratios of moles of the amine groups of cationic polymers to those of the phosphate groups of nucleic acids or hyaluronic acids) of PolyMet/HA complex were modulated and the size, polydispersity and ξ-potential of the nanoparticles were compared. Large aggregates were observed at an N/P ratio around 0.9, where a neutral complex was formed. To form smaller particles, a ratio of about 0.6 was employed, as the complex stayed negatively charged (~−20 mV) with a relatively small size (~100 nm), at this ratio the PEI-HA complex had a similar charge and size with PolyMet-HA complex (FIG. 3).

Figure 4A:
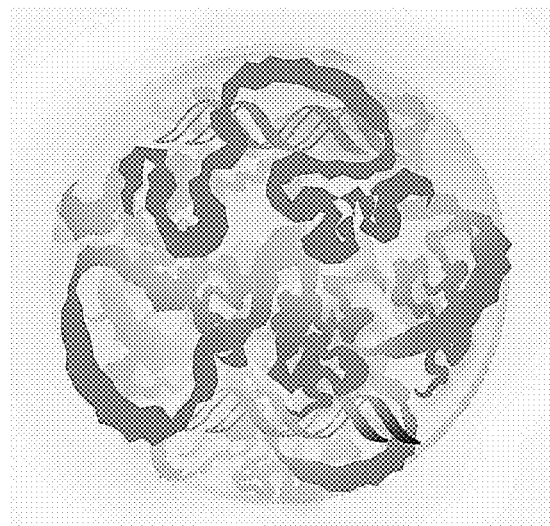
FIG. 4A&B Schematic illustration and (C, D) representative transmission electron microscopy (TEM) images of PolyMet/HA complex (A, C) LPH-PolyMet (B, D).
Figure 4B:
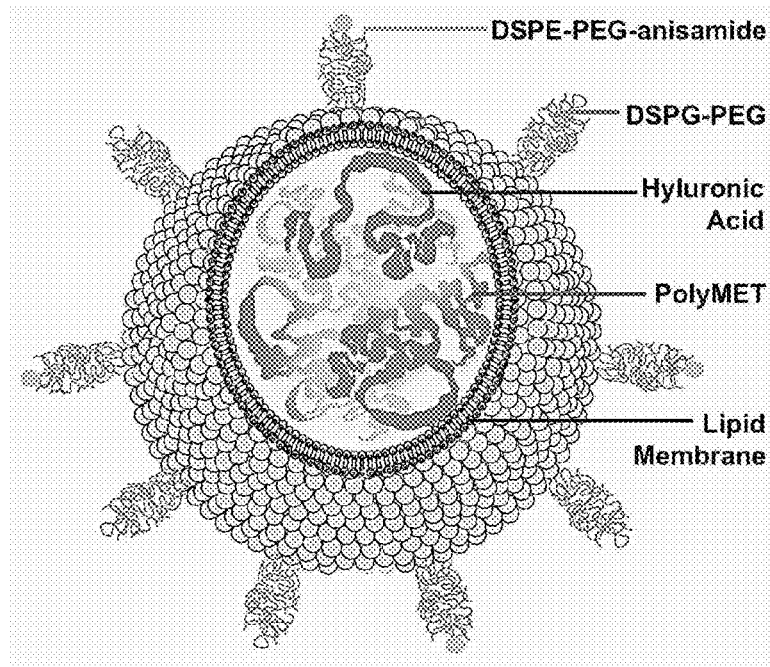
FIG. 4E depicts dynamic light scattering (DLS) measurement of nanoparticles.
Figures 4C, 4D:
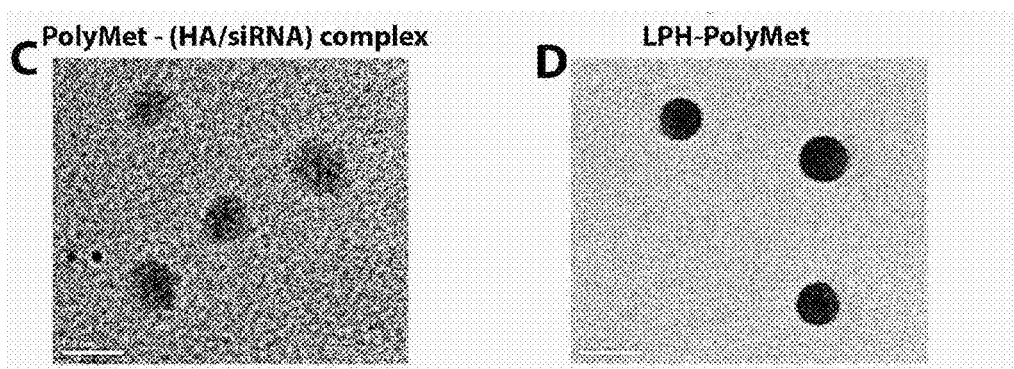

Next, DOTAP/Cholesterol (1:1 mol/mol) cationic liposomes were added to the complex to form the lipid coating through charge-charge interactions. DSPE-PEG and DSPE-PEG-anisamide were then added into the liposome by the post-insertion method. Due to the fact that the sigma receptor is over-expressed in H460 (Miao, L. G., S.; Zhang, J.; Kim, W.; Huang, L. Nanoparticles with Precise Ratiometric Co-Loading and Co-Delivery of Gemcitabine Monophosphate and Cisplatin for Treatment of Bladder Cancer. *Advanced Functional Materials* 24, 6601-6611(2014)), anisamide is applied as the targeting ligand to specifically deliver nanoparticles to the tumor. The final nanoparticles are 70-80 nm with a positive charge of around 20 mV (FIG. 4).

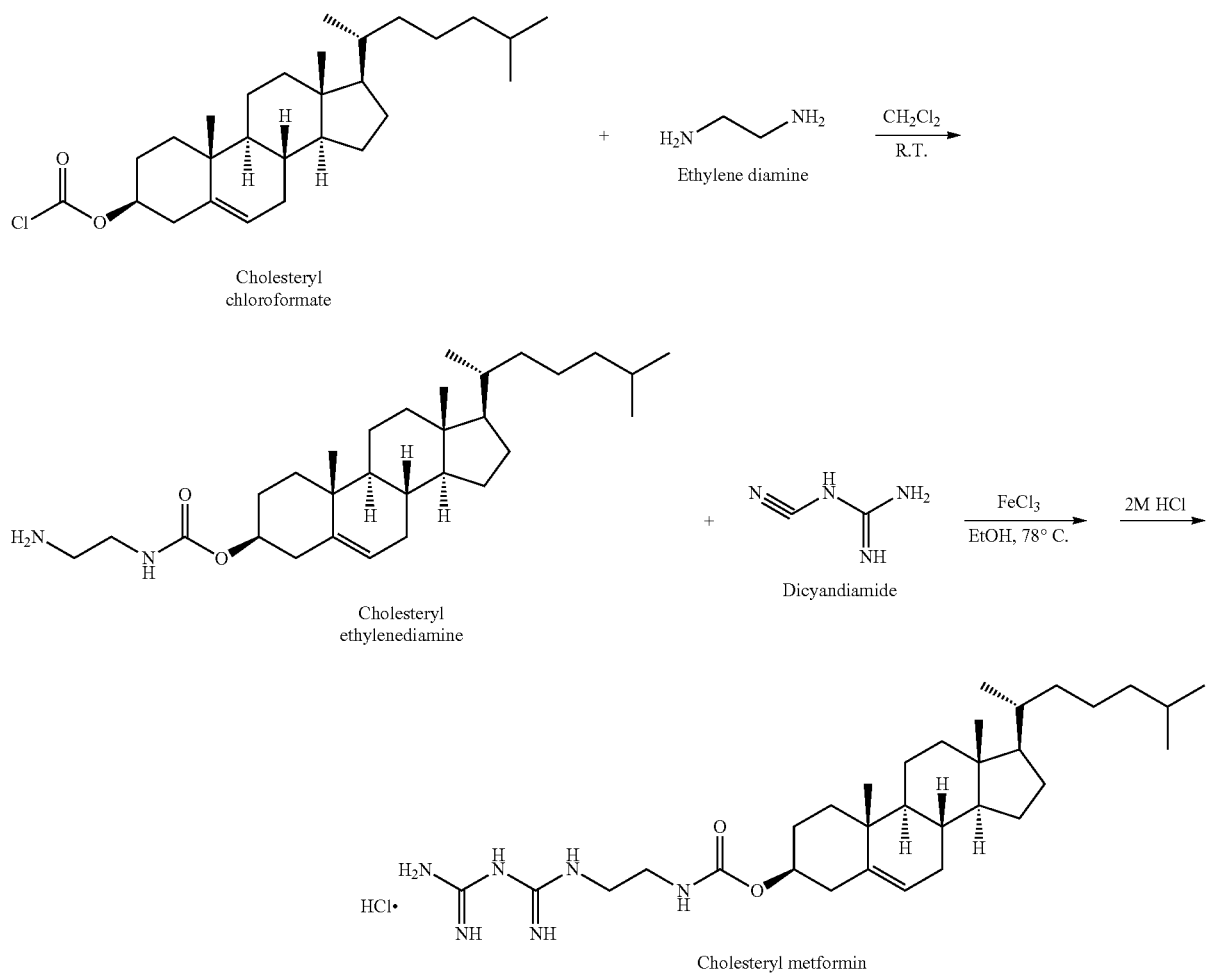
Scheme 2 depicts synthesis of cholesteryl-metformin.
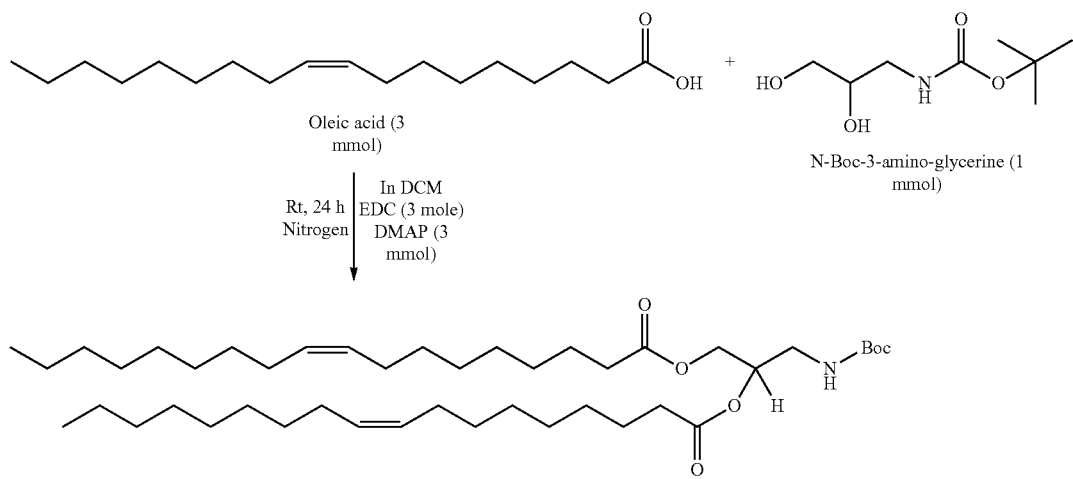

Step 2:

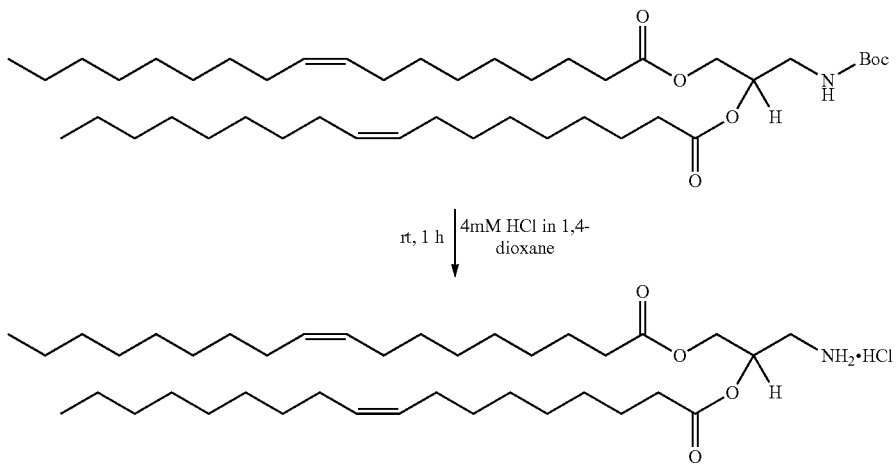

1,2-di-(9Z-octadecenoyl)-3-amino-propane (DOAP)

Step 3:

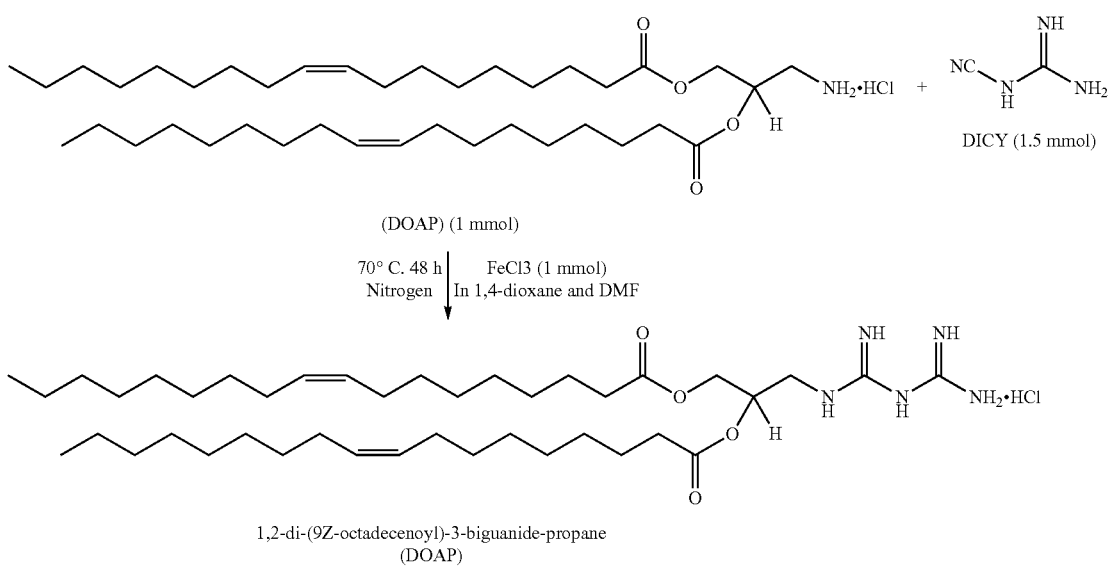

1,2-di-(9Z-octadecenoyl)-3-biguanide-propane
(DOAP)

Scheme 3 depicts the synthesis of metformin modified DOTAP (DOBP) cationic lipid.

Pharmaceutical Formulations

As used herein, the term "deliver" refers to the transfer of a substance or molecule (e.g., a polynucleotide, bioactive compound, or drug) to a physiological site, tissue, or cell. This encompasses delivery to the intracellular portion of a cell or to the extracellular space. As used herein, the term "intracellular" or "intracellularly" has its ordinary meaning as understood in the art. In general, the space inside of a cell, which is encircled by a membrane, is defined as "intracellular" space. Similarly, as used herein, the term "extracellular" or "extracellularly" has its ordinary meaning as understood in the art. In general, the space outside of the cell membrane is defined as "extracellular" space.

The methods disclosed herein provide for delivering a therapeutic agent or a derivative or analog of the agent. By the terms "derivative" or "analog," is meant a chemically modified therapeutic agent. For example, a therapeutic agent's solubility may be modified by increasing or decreasing its hydrophobic by methods known in the art.

The nanoparticles described herein are useful in mammalian tissue culture systems, in animal studies, and for therapeutic purposes. The nanoparticles comprising a bioactive compound having therapeutic activity when expressed or introduced into a cell can be used in therapeutic applications. The nanoparticles can be administered for therapeutic purposes or pharmaceutical compositions comprising the nanoparticles along with additional pharmaceutical carriers can be formulated for delivery, i.e., administering to the subject, by any available route including, but not limited, to parenteral (e.g., intravenous), intradermal, subcutaneous, oral, nasal, bronchial, opthalmic, transdermal (topical), transmucosal, rectal, and vaginal routes. In some embodiments, the route of delivery is intravenous, parenteral, transmucosal, nasal, bronchial, vaginal, and oral.

As used herein the term "pharmaceutically acceptable carrier" includes solvents, dispersion media, coatings, antibacterial and antifungal agents, isotonic and absorption delaying agents, and the like, compatible with pharmaceutical administration. Supplementary active compounds also can be incorporated into the compositions.

As one of ordinary skill in the art would appreciate, a presently disclosed pharmaceutical composition is formulated to be compatible with its intended route of administration. Solutions or suspensions used for parenteral (e.g., intravenous), intramuscular, intradermal, or subcutaneous application can include the following components: a sterile diluent such as water for injection, saline solution, fixed oils, polyethylene glycols, glycerine, propylene glycol or other synthetic solvents; antibacterial agents, such as benzyl alcohol or methyl parabens; antioxidants, such as ascorbic acid or sodium bisulfite; chelating agents, such as ethylenediaminetetraacetic acid; buffers, such as acetates, citrates or phosphates; and agents for the adjustment of tonicity, such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions or dispersions such as those described elsewhere herein and sterile powders for the extemporaneous preparation of sterile injectable solutions or dispersions. For intravenous administration, suitable carriers include physiological saline, bacteriostatic water, or phosphate buffered saline (PBS). The composition should be sterile and should be fluid to the extent that easy syringability exists. In some embodiments, the pharmaceutical compositions are stable under the conditions of manufacture and storage and should be preserved against the contaminating action of microorganisms, such as bacteria and fungi. In general, the relevant carrier can be a solvent or dispersion medium containing, for example, water, ethanol, polyol (for example, glycerol, propylene glycol, and liquid polyetheylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. In some embodiments, isotonic agents, for example, sugars, polyalcohols, such as mannitol or sorbitol, or sodium chloride are included in the formulation. Prolonged absorption of the injectable formulation can be brought about by including in the formulation an agent that delays absorption, for example, aluminum monostearate and gelatin.

Sterile injectable solutions can be prepared by filter sterilization as described elsewhere herein. In certain embodiments, solutions for injection are free of endotoxin. Generally, dispersions are prepared by incorporating the nanoparticles into a sterile vehicle which contains a basic dispersion medium and the required other ingredients from those enumerated above. In those embodiments in which sterile powders are used for the preparation of sterile injectable solutions, the solutions can be prepared by vacuum drying and freeze-drying which yields a powder of the active ingredient plus any additional desired ingredient from a previously sterile-filtered solution thereof.

Oral compositions generally include an inert diluent or an edible carrier. Oral compositions can be prepared using a fluid carrier for use as a mouthwash. Pharmaceutically compatible binding agents, and/or adjuvant materials can be included as part of the composition. The oral compositions can include a sweetening agent, such as sucrose or saccharin; or a flavoring agent, such as peppermint, methyl salicylate, or orange flavoring.

For administration by inhalation, the presently disclosed compositions can be delivered in the form of an aerosol spray from a pressured container or dispenser which contains a suitable propellant, e.g., a gas such as carbon dioxide, or a nebulizer. Liquid aerosols, dry powders, and the like, also can be used.

Systemic administration of the presently disclosed compositions also can be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical or cosmetic carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of individuals. Guidance regarding dosing is provided elsewhere herein.

In an embodiment, the present subject matter also includes an article of manufacture providing a nanoparticle described herein. The article of manufacture can include a vial or other container that contains a composition suitable for the present method together with any carrier, either dried or in liquid form. The article of manufacture further includes instructions in the form of a label on the container and/or in the form of an insert included in a box in which the container is packaged, for carrying out the method of the invention. The instructions can also be printed on the box in which the vial is packaged. The instructions contain information such as sufficient dosage and administration information so as to allow the subject or a worker in the field to administer the pharmaceutical composition. It is anticipated that a worker in the field encompasses any doctor, nurse, technician, spouse, or other caregiver that might administer the composition. The pharmaceutical composition can also be self-administered by the subject.

The delivery of a bioactive compound to a cell can comprise an in vitro approach, an ex vivo approach, in which the delivery of the bioactive compound into a cell occurs outside of a subject (the transfected cells can then be transplanted into the subject), and an in vivo approach, wherein the delivery occurs within the subject itself.

Delivery of a therapeutically effective amount of nanoparticles can be obtained via administration of a pharmaceutical composition comprising a therapeutically effective dose of the bioactive compound or the nanoparticles. By "therapeutically effective amount" or "dose" is meant the concentration of a delivery system or a bioactive compound comprised therein that is sufficient to elicit the desired therapeutic effect. An effective amount can be administered one or more times.

Methods to determine efficacy and dosage are known to those skilled in the art. See, for example, Isselbacher et al. (1996) *Harrison's Principles of Internal Medicine* 13 ed., 1814-1882, herein incorporated by reference. It is understood that appropriate doses of a compound depend upon its potency and can optionally be tailored to the particular recipient, for example, through administration of increasing doses until a preselected desired response is achieved. It is understood that the specific dose level for any particular animal subject can depend on a variety of factors including the activity of the specific compound employed, the age, body weight, general health, gender, and diet of the subject, the time of administration, the route of administration, the rate of excretion, any drug combination, and the degree of expression or activity to be modulated.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic (e.g., immunotoxic) and therapeutic effects is the therapeutic index and it can be expressed as the ratio $LD_{50}/ED_{50}$. Compounds which exhibit high therapeutic indices are preferred. While compounds that exhibit toxic side effects can be used, care should be taken to design a delivery system that targets such compounds to the site of affected tissue to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the presently disclosed methods, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

The pharmaceutical formulation can be administered at various intervals and over different periods of time as required, e.g., multiple times per day, daily, every other day, once a week for between about 1 to 10 weeks, between 2 to 8 weeks, between about 3 to 7 weeks, about 4, 5, or 6 weeks, and the like. The skilled artisan will appreciate that certain factors can influence the dosage and timing required to effectively treat a subject, including but not limited to the severity of the disease, disorder, or unwanted condition, previous treatments, the general health and/or age of the subject, and other diseases or unwanted conditions present. Generally, treatment of a subject can include a single treatment or, in many cases, can include a series of treatments. Further, treatment of a subject can include a single cosmetic application or, in some embodiments, can include a series of cosmetic applications.

The present invention also includes an article of manufacture providing a nanoparticle described herein. The article of manufacture can include a vial or other container that contains a composition suitable for the present method together with any carrier, either dried or in liquid form. The article of manufacture further includes instructions in the form of a label on the container and/or in the form of an insert included in a box in which the container is packaged, for carrying out the method of the invention. The instructions can also be printed on the box in which the vial is packaged. The instructions contain information such as sufficient dosage and administration information so as to allow the subject or a worker in the field to administer the pharmaceutical composition. It is anticipated that a worker in the field encompasses any doctor, nurse, technician, spouse, or other caregiver that might administer the composition. The pharmaceutical composition can also be self-administered by the subject.

One of ordinary skill in the art upon review of the presently disclosed subject matter would appreciate that the presently disclosed PolyMet compounds, nanoparticles and pharmaceutical compositions thereof, can be administered directly to a cell, a cell culture, a cell culture medium, a tissue, a tissue culture, a tissue culture medium, and the like. When referring to the delivery systems of the invention, the term "administering," and derivations thereof, comprises any method that allows for the compound to contact a cell. The presently disclosed compounds or pharmaceutical compositions thereof, can be administered to (or contacted with) a cell or a tissue in vitro or ex vivo. The presently disclosed PolyMet compounds, nanoparticles and pharmaceutical compositions thereof, also can be administered to (or contacted with) a cell or a tissue in vivo by administration to an individual subject, e.g., a patient, for example, by systemic administration (e.g., intravenous, intraperitoneal, intramuscular, subdermal, or intracranial administration) or topical application, as described elsewhere herein.

The following examples are offered by way of illustration and not by way of limitation.

EXAMPLES

Materials and Methods

Chemicals 1,2-Dioleoyl-3-trimethylammonium-propane chloride salt (DOTAP) and 1,2-distearoryl-sn-glycero-3-phosphoethanolamine-N-[methoxy(polyethyleneglycol-2000) ammonium salt (DSPE-PEG2000) were purchased from Avanti Polar Lipids, Inc. (Alabaster, Ala.). DSPE-PEG-anisamide (AA) was synthesized in our lab as described previously (Banerjee, R., Tyagi, P., Li, S. & Huang, L. Anisamide-targeted stealth liposomes: a potent carrier for targeting doxorubicin to human prostate cancer cells. *International journal of cancer. Journal international du cancer* 112, 693-700 (2004)). DeadEnd Fluorometric TUNEL assay kits and Luciferase Assay System assay substrates were obtained from Promega (Madison, Wis.). Other chemicals were obtained from Sigma-Aldrich (St. Louis, Mo.). BCL2 siRNA (target sequence: 5'-AAC AUC GCC CUG UGG AUG ACU-3'), VEGF siRNA (target sequence: 5'-ACC UCA CCA AGG CCA GCA C-3') and control siRNA (target sequence: 5'-AAU UCU CCG AAC GUG UCA CGU-3') were synthesized by Sigma-Aldrich (St Louis, Mo.).

Cell Culture

H460, H460/Luc human NSCLC cells, B16F10, and B16F10/Luc mouse melanoma cancer cells were originally obtained from American Type Culture Collection (ATCC) and were cultured in DMEM medium (Invitrogen, Carlsbad, Calif.) supplemented with 10% fetal bovine serum (Life Technologies, Carlsbad, Calif.), 100 U/mL penicillin, and 100 μg/mL streptomycin (Invitrogen). Cells were cultured in a humidified incubator at 37° C. and 5% CO2.

Experimental Mice

Female nude female mice and female CD1 mice that were 6-8 weeks old were used in the studies. Female nude mice were purchased from National Cancer Institute (Bethesda, Md.) and bred by the Division of Laboratory Animal Medicine (DLAM) at University of North Carolina at Chapel Hill. CD1 mice were purchased from Charles River Laboratories (Morrisville, N.C.). To establish the xenograft models, 5×106 cells in 100 μL of PBS were injected subcutaneously into the right flank of the mice.

Example 1: Preparation of PolyMet

To prepare PolyMet, 0.2 g of linear PEI and 2 g of dicyandiamide were mixed in 10 mL of water. Then 2 mL of HCl was added into the solution. The compounds then reacted at 100° C. for about 4 h. PolyMet was then purified through an ultrafiltration tube with a cutoff of 3000 Da and lyophilized. The solution of PolyMet was kept in 1 mg/mL, 1 mL aliquots for experiment.

Example 2: Preparation of LPH Nanoparticles

DOTAP (20 mM, 1 mL) and cholesterol (20 mM, 1 mL) were dissolved (1:1 mol/mol) in chloroform and the solvent was removed under reduced pressure. The lipid film was hydrated overnight with 2 mL of distilled water to form cationic liposomes (10 mM), which were sequentially extruded through polycarbonate membranes (200 nm×20 times, 100 nm×20 times and 50 nm×20 times) (Millipore, Billerica, Mass.).

Several different complexes having differing ratios were prepared. To prepare the PolyMet-HA or PEI-HA complexes, 200 μL of HA (25 μg HA, in DI water) and 200 μL of PEI solution (containing 2-3.9 μg PEI in DI water) or 200 μL of PolyMet solution (containing 5.8-11.6 μg PolyMet in DI water) was mixed in a 1.5 mL tube. The complexes were mixed by pipetting up and down 10 times and allowed to stand at room temperature for 10 min before analysis of size and zeta potential. The ratio of the complex was determined by the results from particle size and zeta potential determined by Dynamic light scattering (DLS) using a Malvern ZetaSizer Nano series (Westborough, Mass.).

After the desired ratio of the complex was chosen, the complex was mixed with 60 μL cationic DOTAP/cholesterol liposomes (10 mM) and incubated for another 10 min for lipid coating. The lipid-coated nanoparticles were PEGylated using a post-insertional approach by adding 45 μL DSPE-PEG and DSPE-PEG-AA (10 mg/mL 1:1 v/v) and incubating the nanoparticles at 50° C. for 15 min. The resulting LPH nanoparticles were used within 20 min for the following experiments.

For the siRNA study, instead of using 200 μL of HA (25 μg HA, in DI water) solution, 200 μL of HA/siRNA (12.5 μg HA, 12.5 μg siRNA, in DI water) solution was used and mixed with different amounts of PolyMet or PEI solutions in a 1.5 mL tube before selecting the formulation with the desired ratio.

Example 3: Characterization of LPH NPs

Transmission electron microscope (TEM) images of LPH were acquired through the use of JEOL 100CX II TEM (Tokyo, Japan). Briefly, freshly prepared LPH nanoparticles (5 μL) were carefully dropped onto a 300-mesh carbon-coated copper grid (Ted Pella, Inc., Redding, Calif.) and allowed to stand at room temperature for 5 min. Grids were then stained with 1% uranyl acetate (5 μL) and allowed to incubate briefly (10 seconds) and quickly dry. All images were acquired at an accelerating voltage of 100 kV.

Example 4: Animal Tumor Model and Antitumor Activity

Human NSCLC cells xenografts were used as previously described. H460 human lung cancer cells (5.0×106) were subcutaneously injected into the right flanks of female athymic nu/nu mice. When the tumors reached about 0.1 cm$^3$ in size (10-15 days after transplantation), H460 tumor-bearing mice were given intravenous tail vein (IV) injections with formulations every second day. Animal weight and tumor volumes were measured every other day. The tumor length (L) and width (W) were used to calculate volume (V) by the equation:

$$V = 1/2 \times L \times W^2.$$

Example 5: Western Blot Analysis

H460 tumor-bearing mice were given IV injections every second day and mice were sacrificed 24 hours after the third injection. Protein per lane was separated by 4%-12% SDS-PAGE electrophoresis (Invitrogen) before being transferred to polyvinylidene difluoride (PVDF) membranes (Bio-Rad). The membranes were blocked for 1 h with 5% non fat dry milk (Bio-Rad) at room temperature and then incubated with antibodies overnight at 4° C. The membranes were washed 3 times and then incubated with a secondary antibody (1:4,000 dilution; Cell signal Inc.) at room temperature for 1 h. Finally, the membranes were washed 4 times and developed using an enhanced chemiluminescence system according to the manufacturer's instructions (Thermo scientific).

Example 6: Immunostaining

In vivo tumor cell apoptosis after systemic administration was determined by the TdT-mediated dUTP Nick-End Labeling (TUNEL) assay. H460 tumor-bearing mice were given IV injections with the formulations every second day for a total of three times. Twenty-four hours after the final injection, mice were sacrificed and tumors were fixed in 10% formalin for 24 h before being embedded in paraffin and sectioned at a thickness of 5 μm.

The TUNEL staining was performed as recommended by the manufacturer (Promega). DAPI mounting medium (Vector Laboratories, Inc., Burlingame, Calif.) was dropped on the sections for nucleus staining. Images of TUNEL-stained tumor sections were captured with a fluorescence microscope (Nikon Corp., Tokyo, Japan). The percentage of apoptotic cells was obtained by dividing the number of apoptotic cells from the number of total cells (blue nuclei stained by DAPI, not shown) in each microscopic field. Ten representative microscopic fields were randomly selected in each treatment group (n=3) for this analysis.

Example 7: Serum Biochemical Value Analysis and Hematology Assay

After three injections, the whole blood was collected and centrifuged at 4,000 rpm for 5 min to obtain the serum. Blood urea nitrogen (BUN), creatinine (Crea), serum aspartate aminotransferase (AST) and alanine aminotransferase (ALT) levels were assayed as indicators of renal and hepatic function. Whole blood was collected from healthy nude mice after three repeated treatments. Red blood cells (RBC), white blood cells (WBC), platelets (PLT), hemoglobin (HGB) and hematocrits (HCT) were counted for the detection of myelosuppression. Organs (heart, liver, spleen, lung, and kidney) were fixed and sectioned for H&E staining to evaluate organ-specific toxicity.

Example 8: In Vitro Luciferase Gene Silencing Study

H460/Luc cells (1×104 cells/0.2 mL/well) were seeded in 96-well plates (Corning Inc., Corning, N.Y.) one day before experiments. Cells were treated with different formulations containing 6, 60, or 150 nM luciferase-siRNA in 100 µL serum-free opti-MEM media at 37° C. for 4 h. Cells were then washed three times with PBS followed by incubation with 100 µL complete DMEM media for another 24 h. Cells were then washed with PBS and incubated with 60 µL lysis buffer (0.05% Triton X-100 and 2 mM EDTA in 0.1 M Tris-HCl) for 30 min. Then 40 µL of lysate was transferred to a new white 96 plate and mixed with 100 µL substrate (Luciferase Assay System, Promega Co., Madison, Wis.), the luminescence intensity was measured by a plate reader (Plate Chameleon Multilabel Detection Platform, Bioscan Inc., Washington D.C.). The protein concentrations were determined by using a protein assay kit (BCA protein assay kit, Thermo Science). Luciferase activity of each sample was normalized with the protein level.

Example 9: Synthesis of Cholesteryl Metformin

Solid cholesteryl chloroformate (1.0 g, 2.2 mmol) was dissolved in 10 mL of dichloromethane (DCM). In a separate flask 0.22 mol ethylenediamine (13.2 g) was diluted with 10 mL of DCM. While stirring, the cholesteryl chloroformate solution was drop-wise added to the ethylenediamine solution over a 30 minute period at room temperature (R.T.). Following an overnight R.T. stir, the organic solvent was evaporated until a minimal sample volume remained. Approximately 20 mL of acetonitrile was added to precipitate the crude product. The solid was then collected, rinsed several times with acetonitrile and then air-dried. The yield was 92%. Equimolar cholesterol ethylenediamine (1.0 mmol), dicyandiamide (1.0 mmol) and ferric chloride (1.0 mmol) were dissolved in 10 mL of ethanol. The mixture was warmed to 78° C. and stirred for 3 hours. After evaporation of ethanol, 5 mL diluted hydrochloric acid (2 mol/L) was added to displace ferric ions. Then the product was isolated and rinsed several times with acetonitrile and then air-dried. The yield was 71%.

Statistics analysis: The differences between treatment groups were analyzed by using the Student's t-test for pairs of groups and one-way analysis of variance (ANOVA) for multiple groups. A p value less than 0.05 is considered statistically significant. All statistical analyses were carried out using GraphPad Prism Software (Version 5.0, GrapPad Software, San Diego, Calif.).

All technical and scientific terms used herein have the same meaning. Efforts have been made to ensure accuracy with respect to numbers used (e.g. amounts, temperature, etc.) but some experimental errors and deviations should be accounted for.

It is to be noted that the term "a" or "an" entity refers to one or more of that entity; for example, "a nanoparticle" is understood to represent one or more nanoparticles. As such, the terms "a" (or "an"), "one or more," and "at least one" can be used interchangeably herein.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments±20%, in some embodiments±10%, in some embodiments±5%, in some embodiments±1%, in some embodiments±0.5%, and in some embodiments±0.1% from the specified amount, as such variations are appropriate to perform the disclosed methods or employ the disclosed compositions.

Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the presently disclosed subject matter be limited to the specific values recited when defining a range.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the foregoing list of embodiments and appended claims. Although specific terms are employed herein, they are used in a generic and descriptive sense only and not for purposes of limitation.

That which is claimed:
1. A nanoparticle comprising:
   i. a lipid outer membrane; and
   ii. a polymer encapsulated by the lipid outer membrane, said polymer having the following chemical formula I

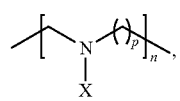

wherein, p is 1 or 2, n is an integer from two (2) to 10,000; and wherein, X is hydrogen or a residue of Metformin having the formula:

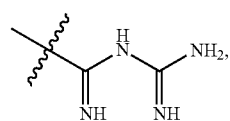 [SMILES: *C(=N)NC(=N)N]

wherein at least 5% of X in the polymer is a residue of Metformin.

2. The nanoparticle of claim 1 further comprising a cargo complexed with
the polymer, wherein the cargo is a therapeutic agent.

3. A method of delaying, inhibiting, decreasing, slowing or ameliorating type 2 diabetes or cancer by administering the nanoparticle of claim 1 to a subject.

* * * * *